US012082813B2

(12) United States Patent
Nguyen et al.

(10) Patent No.: US 12,082,813 B2
(45) Date of Patent: *Sep. 10, 2024

(54) MULTI-WINDOW GUIDE TUNNEL

(71) Applicant: Ancora Heart, Inc., Santa Clara, CA (US)

(72) Inventors: Huu Nguyen, San Jose, CA (US); Son Nguyen, San Jose, CA (US); Eugene Serina, Fremont, CA (US); Tammy Y. Tam, San Francisco, CA (US)

(73) Assignee: ANCORA HEART, INC., Santa Clara, CA (US)

( * ) Notice: Subject to any disclaimer, the term of this patent is extended or adjusted under 35 U.S.C. 154(b) by 847 days.

This patent is subject to a terminal disclaimer.

(21) Appl. No.: 16/749,647

(22) Filed: Jan. 22, 2020

(65) Prior Publication Data

US 2020/0229820 A1 Jul. 23, 2020

Related U.S. Application Data

(63) Continuation of application No. 15/652,068, filed on Jul. 17, 2017, now Pat. No. 10,542,987, which is a
(Continued)

(51) Int. Cl.
*A61B 17/10* (2006.01)
*A61B 17/00* (2006.01)
(Continued)

(52) U.S. Cl.
CPC ........ *A61B 17/10* (2013.01); *A61B 17/00234* (2013.01); *A61B 17/0401* (2013.01);
(Continued)

(58) Field of Classification Search
CPC .......... A61F 2/2466; A61B 2017/0409; A61B 2017/0464; A61B 2017/00243
See application file for complete search history.

(56) References Cited

U.S. PATENT DOCUMENTS 2,108,206 A  2/1938  Meeker
3,656,185 A  4/1972  Carpentier
(Continued)

FOREIGN PATENT DOCUMENTS

CN  103690202 A  4/2014
EP  0 363 661 A1  4/1990
(Continued)

OTHER PUBLICATIONS

De Simone, R. et al. (Apr. 15, 1993). "Adjustable Tricuspid Valve Annuloplasty Assisted by Intraoperative Transesophageal Color Doppler Echocardiography," *Am. J. Cardiol.* 71(11):926-931.
(Continued)

*Primary Examiner* — Alexander J Orkin
(74) *Attorney, Agent, or Firm* — COOLEY LLP

(57) ABSTRACT

Described herein are devices and methods for delivering implants that include multiple coupled anchors. The anchors are secured to tissue using a multi-opening guide tunnel that is configured to releasably retain one or more portions of the implant located between two of the anchors. The releasable retention of one or more intervening portions of the implant maintains the position of the implant and the guide tunnel until the implant is secured to the tissue. The multi-opening guide tunnel permits securement of the multiple anchors without requiring repositioning of the guide tunnel for each anchor.

20 Claims, 39 Drawing Sheets

Related U.S. Application Data continuation of application No. 14/309,837, filed on Jun. 19, 2014, now Pat. No. 9,706,996, which is a continuation of application No. 12/366,553, filed on Feb. 5, 2009, now Pat. No. 8,790,367.

(60) Provisional application No. 61/026,697, filed on Feb. 6, 2008.

(51) Int. Cl.
  *A61B 17/04* (2006.01)
  *A61B 17/064* (2006.01)
  *A61B 17/068* (2006.01)
  *A61F 2/24* (2006.01)

(52) U.S. Cl.
  CPC .......... *A61B 17/064* (2013.01); *A61B 17/068* (2013.01); *A61B 17/0682* (2013.01); *A61B 17/0684* (2013.01); *A61F 2/2451* (2013.01); *A61F 2/2466* (2013.01); *A61B 2017/00243* (2013.01); *A61B 2017/00783* (2013.01); *A61B 2017/00867* (2013.01); *A61B 2017/0409* (2013.01); *A61B 2017/0414* (2013.01); *A61B 2017/0464* (2013.01); *A61F 2/2445* (2013.01)

(56) References Cited

U.S. PATENT DOCUMENTS

| | | | |
|---|---|---|---|
| 3,727,614 | A | 4/1973 | Kniazuk |
| 3,773,034 | A | 11/1973 | Burns et al. |
| 3,598,576 | A | 5/1976 | Komiya |
| 3,961,419 | A | 6/1976 | Schwartz |
| 3,976,079 | A | 8/1976 | Samuels et al. |
| 4,014,492 | A | 3/1977 | Rothfuss |
| 4,034,473 | A | 7/1977 | May |
| 4,042,979 | A | 8/1977 | Angell |
| 4,043,504 | A | 8/1977 | Hueil et al. |
| 4,053,979 | A | 10/1977 | Tuthill et al. |
| 4,055,861 | A | 11/1977 | Carpentier et al. |
| 4,069,825 | A | 1/1978 | Akiyama |
| 4,290,151 | A | 9/1981 | Massana |
| 4,384,406 | A | 5/1983 | Tischlinger |
| 4,445,892 | A | 5/1984 | Hussein et al. |
| 4,489,446 | A | 12/1984 | Reed |
| 4,494,542 | A | 1/1985 | Lee |
| 4,619,247 | A | 10/1986 | Inoue et al. |
| 4,700,250 | A | 10/1987 | Kuriyama |
| 4,726,371 | A | 2/1988 | Gibbens |
| 4,758,221 | A | 7/1988 | Jureidini |
| 4,784,133 | A | 11/1988 | Mackin |
| 4,798,594 | A | 1/1989 | Hillstead |
| 4,845,851 | A | 7/1989 | Warthen |
| 4,848,341 | A | 7/1989 | Ahmad |
| 4,850,354 | A | 7/1989 | McGurk-Burleson et al. |
| 4,961,738 | A | 10/1990 | Mackin |
| 4,969,893 | A | 11/1990 | Swor |
| 4,976,710 | A | 12/1990 | Mackin |
| 5,053,047 | A | 10/1991 | Yoon |
| 5,064,431 | A | 11/1991 | Gilbertson et al. |
| 5,078,731 | A | 1/1992 | Hayhurst |
| 5,084,058 | A | 1/1992 | Li |
| 5,103,804 | A | 4/1992 | Abele et al. |
| 5,108,368 | A | 4/1992 | Hammerslag et al. |
| 5,133,723 | A | 7/1992 | Li et al. |
| 5,221,255 | A | 6/1993 | Mahurkar et al. |
| 5,221,269 | A | 6/1993 | Miller et al. |
| 5,242,456 | A | 9/1993 | Nash et al. |
| 5,242,457 | A | 9/1993 | Akopov et al. |
| 5,257,975 | A | 11/1993 | Foshee |
| 5,306,296 | A | 4/1994 | Wright et al. |
| 5,312,341 | A | 5/1994 | Turi |
| 5,324,298 | A | 6/1994 | Phillips et al. |
| 5,346,500 | A | 9/1994 | Suchart |
| 5,358,479 | A | 10/1994 | Wilson |
| 5,358,514 | A | 10/1994 | Schulman et al. |
| 5,364,407 | A | 11/1994 | Poll |
| 5,366,479 | A | 11/1994 | McGarry et al. |
| 5,368,591 | A | 11/1994 | Lennox et al. |
| 5,383,905 | A | 1/1995 | Golds et al. |
| 5,395,316 | A | 3/1995 | Martin |
| 5,409,483 | A | 4/1995 | Campbell et al. |
| 5,409,499 | A | 4/1995 | Yi |
| 5,417,700 | A | 5/1995 | Egan |
| 5,423,837 | A | 6/1995 | Mericle et al. |
| 5,437,680 | A | 8/1995 | Yoon |
| 5,439,470 | A | 8/1995 | Li |
| 5,450,860 | A | 9/1995 | O'Connor |
| 5,452,513 | A | 9/1995 | Zinnbauer et al. |
| 5,474,572 | A | 12/1995 | Hayhurst |
| 5,507,760 | A | 4/1996 | Wynne et al. |
| 5,520,702 | A | 5/1996 | Sauer et al. |
| 5,522,873 | A | 6/1996 | Jackman et al. |
| 5,524,630 | A | 6/1996 | Crowley |
| 5,527,323 | A | 6/1996 | Jervis et al. |
| 5,531,686 | A | 7/1996 | Lundquist et al. |
| 5,545,134 | A | 8/1996 | Hilaire et al. |
| 5,545,168 | A | 8/1996 | Burke |
| 5,565,122 | A | 10/1996 | Zinnbauer et al. |
| 5,571,215 | A | 11/1996 | Sterman et al. |
| 5,591,194 | A | 1/1997 | Berthiaume |
| 5,626,590 | A | 5/1997 | Wilk |
| 5,626,614 | A | 5/1997 | Hart |
| 5,630,824 | A | 5/1997 | Hart |
| 5,643,289 | A | 7/1997 | Sauer et al. |
| 5,669,917 | A | 9/1997 | Sauer et al. |
| 5,674,279 | A | 10/1997 | Wright et al. |
| 5,690,655 | A | 11/1997 | Hart et al. |
| 5,709,695 | A | 1/1998 | Northrup, III |
| 5,713,950 | A | 2/1998 | Cox |
| 5,716,370 | A | 2/1998 | Williamson, IV et al. |
| 5,718,725 | A | 2/1998 | Sterman et al. |
| 5,725,542 | A | 3/1998 | Yoon |
| 5,735,290 | A | 4/1998 | Sterman et al. |
| 5,741,260 | A | 4/1998 | Songer et al. |
| 5,741,301 | A | 4/1998 | Pagedas |
| 5,752,518 | A | 5/1998 | McGee et al. |
| 5,752,964 | A | 5/1998 | Mericle |
| 5,752,966 | A | 5/1998 | Chang |
| 5,755,730 | A | 5/1998 | Swain et al. |
| 5,766,240 | A | 6/1998 | Johnson |
| 5,769,812 | A | 6/1998 | Stevens et al. |
| 5,782,861 | A | 7/1998 | Cragg et al. |
| 5,810,848 | A | 9/1998 | Hayhurst |
| 5,810,853 | A | 9/1998 | Yoon |
| 5,817,107 | A | 10/1998 | Schaller |
| 5,827,171 | A | 10/1998 | Dobak, III et al. |
| 5,843,169 | A | 12/1998 | Taheri |
| 5,848,969 | A | 12/1998 | Panescu et al. |
| 5,860,992 | A | 1/1999 | Daniel et al. |
| 5,860,993 | A | 1/1999 | Thompson et al. |
| 5,868,733 | A | 2/1999 | Ockuly et al. |
| 5,879,371 | A | 3/1999 | Gardiner et al. |
| 5,885,238 | A | 3/1999 | Stevens et al. |
| 5,888,240 | A | 3/1999 | Carpentier et al. |
| 5,902,321 | A | 5/1999 | Caspari et al. |
| 5,904,651 | A | 5/1999 | Swanson et al. |
| 5,906,579 | A | 5/1999 | Vander Salm et al. |
| 5,911,717 | A | 6/1999 | Jacobsen et al. |
| 5,919,207 | A | 7/1999 | Taheri |
| 5,919,208 | A | 7/1999 | Valenti |
| 5,935,149 | A | 8/1999 | Ek |
| 5,947,983 | A | 9/1999 | Solar et al. |
| 5,961,440 | A | 10/1999 | Schweich, Jr. et al. |
| 5,961,539 | A | 10/1999 | Northrup, III et al. |
| 5,972,004 | A | 10/1999 | Williamson, IV et al. |
| 5,984,933 | A | 11/1999 | Yoon |
| 5,989,284 | A | 11/1999 | Laufer |
| 5,991,650 | A | 11/1999 | Swanson et al. |
| 6,010,531 | A | 1/2000 | Donlon et al. |
| 6,015,428 | A | 1/2000 | Pagedas |
| 6,045,497 | A | 4/2000 | Schweich, Jr. et al. |
| 6,050,936 | A | 4/2000 | Schweich, Jr. et al. |
| 6,056,743 | A | 5/2000 | Ellis et al. |

(56) References Cited

U.S. PATENT DOCUMENTS

| | | |
|---|---|---|
| 6,059,715 A | 5/2000 | Schweich, Jr. et al. |
| 6,066,160 A | 5/2000 | Colvin et al. |
| 6,074,401 A | 6/2000 | Gardiner et al. |
| 6,077,214 A | 6/2000 | Mortier et al. |
| 6,077,989 A | 6/2000 | Kandel et al. |
| 6,099,553 A | 8/2000 | Hart et al. |
| 6,102,945 A | 8/2000 | Campbell |
| 6,125,852 A | 10/2000 | Stevens et al. |
| 6,149,658 A | 11/2000 | Gardiner et al. |
| 6,162,168 A | 12/2000 | Schweich, Jr. et al. |
| 6,165,183 A | 12/2000 | Kuehn et al. |
| 6,171,329 B1 | 1/2001 | Shaw et al. |
| 6,183,469 B1 | 2/2001 | Thapliyal et al. |
| 6,197,017 B1 | 3/2001 | Brock et al. |
| 6,203,531 B1 | 3/2001 | Ockuly et al. |
| 6,221,084 B1 | 4/2001 | Fleenor |
| 6,228,055 B1 | 5/2001 | Foerster et al. |
| 6,228,096 B1 | 5/2001 | Marchand |
| 6,250,308 B1 | 6/2001 | Cox |
| 6,254,620 B1 | 7/2001 | Koh et al. |
| 6,258,118 B1 | 7/2001 | Baum et al. |
| 6,260,552 B1 | 7/2001 | Mortier et al. |
| 6,269,819 B1 | 8/2001 | Oz et al. |
| 6,283,993 B1 | 9/2001 | Cosgrove et al. |
| 6,306,149 B1 | 10/2001 | Meade |
| 6,312,447 B1 | 11/2001 | Grimes |
| 6,328,727 B1 | 12/2001 | Frazier et al. |
| 6,332,893 B1 | 12/2001 | Mortier et al. |
| 6,355,030 B1 | 3/2002 | Aldrich et al. |
| 6,378,289 B1 | 4/2002 | Trudeau et al. |
| 6,391,048 B1 | 5/2002 | Ginn et al. |
| 6,406,420 B1 | 6/2002 | McCarthy et al. |
| 6,409,743 B1 | 6/2002 | Fenton, Jr. |
| 6,423,088 B1 | 7/2002 | Fenton, Jr. |
| 6,432,123 B2 | 8/2002 | Schwartz et al. |
| 6,461,327 B1 | 10/2002 | Addis et al. |
| 6,491,689 B1 | 12/2002 | Ellis et al. |
| 6,514,265 B2 | 2/2003 | Ho et al. |
| 6,524,328 B2 | 2/2003 | Levinson |
| 6,524,338 B1 | 2/2003 | Gundry |
| 6,533,753 B1 | 3/2003 | Haarstad et al. |
| 6,551,332 B1 | 4/2003 | Nguyen et al. |
| 6,575,971 B2 | 6/2003 | Hauck et al. |
| 6,575,987 B2 | 6/2003 | Gellman et al. |
| 6,589,160 B2 | 7/2003 | Schweich, Jr. et al. |
| 6,602,288 B1 | 8/2003 | Cosgrove et al. |
| 6,602,289 B1 | 8/2003 | Colvin et al. |
| 6,607,541 B1 | 8/2003 | Gardiner et al. |
| 6,613,059 B2 | 9/2003 | Schaller et al. |
| 6,619,291 B1 | 9/2003 | Hlavka et al. |
| 6,626,899 B2 | 9/2003 | Houser et al. |
| 6,629,534 B1 | 10/2003 | St. Goar et al. |
| 6,641,593 B1 | 11/2003 | Schaller et al. |
| 6,648,903 B1 | 11/2003 | Pierson, III |
| 6,651,671 B1 | 11/2003 | Donlon et al. |
| 6,655,386 B1 | 12/2003 | Makower et al. |
| 6,669,687 B1 | 12/2003 | Saadat |
| 6,676,702 B2 | 1/2004 | Mathis |
| 6,689,164 B1 | 2/2004 | Seguin |
| 6,699,263 B2 | 3/2004 | Cope |
| 6,702,826 B2 | 3/2004 | Liddicoat et al. |
| 6,716,243 B1 | 4/2004 | Colvin et al. |
| 6,718,985 B2 | 4/2004 | Hlavka et al. |
| 6,723,038 B1 | 4/2004 | Schoeder et al. |
| 6,723,107 B1 | 4/2004 | Skiba et al. |
| 6,733,509 B2 | 5/2004 | Nobles et al. |
| 6,746,457 B2 | 6/2004 | Dana et al. |
| 6,749,622 B2 | 6/2004 | McGuckin et al. |
| 6,752,813 B2 | 6/2004 | Goldfarb et al. |
| 6,790,231 B2 | 9/2004 | Liddicoat et al. |
| 6,793,618 B2 | 9/2004 | Schweich, Jr. et al. |
| 6,802,851 B2 | 10/2004 | Jones et al. |
| 6,811,560 B2 | 11/2004 | Jones et al. |
| 6,818,001 B2 | 11/2004 | Wulfman et al. |
| 6,875,224 B2 | 4/2005 | Grimes |
| 6,908,424 B2 | 6/2005 | Mortier et al. |
| 6,923,818 B2 | 8/2005 | Muramatsu et al. |
| 6,932,792 B1 | 8/2005 | St. Goar et al. |
| 6,951,557 B2 | 10/2005 | Ellis et al. |
| 6,986,775 B2 | 1/2006 | Morales et al. |
| 6,991,643 B2 | 1/2006 | Saadat |
| 6,997,931 B2 | 2/2006 | Sauer et al. |
| 7,004,958 B2 | 2/2006 | Adams et al. |
| 7,037,334 B1 | 5/2006 | Hlavka et al. |
| 7,044,957 B2 | 5/2006 | Foerster et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,166,127 B2 | 1/2007 | Spence et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,235,086 B2 | 6/2007 | Sauer et al. |
| 7,241,310 B2 | 7/2007 | Taylor et al. |
| 7,326,231 B2 | 2/2008 | Phillips et al. |
| 7,335,213 B1 | 2/2008 | Hyde et al. |
| 7,344,544 B2 | 3/2008 | Bender et al. |
| 7,452,325 B2 | 11/2008 | Schaller |
| 7,534,204 B2 | 5/2009 | Starksen et al. |
| 7,588,582 B2 | 9/2009 | Starksen et al. |
| 7,618,449 B2 | 11/2009 | Tremulis et al. |
| 7,655,040 B2 | 2/2010 | Douk et al. |
| 7,666,193 B2 | 2/2010 | Starksen et al. |
| 7,727,247 B2 | 6/2010 | Kimura et al. |
| 7,753,858 B2 | 7/2010 | Starksen et al. |
| 7,753,922 B2 | 7/2010 | Starksen |
| 7,753,924 B2 | 7/2010 | Starksen et al. |
| 7,758,637 B2 | 7/2010 | Starksen et al. |
| 7,766,812 B2 | 8/2010 | Schroeder et al. |
| 7,832,406 B2 | 11/2010 | Ellis et al. |
| 7,850,600 B1 | 12/2010 | Piskun |
| 7,883,538 B2 | 2/2011 | To et al. |
| 7,918,787 B2 | 4/2011 | Saadat |
| 7,922,762 B2 | 4/2011 | Starksen |
| 7,993,368 B2 | 8/2011 | Gambale et al. |
| 8,066,766 B2 | 11/2011 | To et al. |
| 8,287,555 B2 | 10/2012 | Starksen et al. |
| 8,287,557 B2 | 10/2012 | To et al. |
| 8,343,173 B2 | 1/2013 | Starksen et al. |
| 8,641,727 B2 | 2/2014 | Starksen et al. |
| 8,790,367 B2 | 7/2014 | Nguyen et al. |
| 9,072,513 B2 | 7/2015 | To et al. |
| 9,226,825 B2 | 1/2016 | Starksen et al. |
| 9,468,528 B2 | 10/2016 | Starksen et al. |
| 9,706,996 B2 * | 7/2017 | Nguyen .......... A61B 17/068 |
| 9,949,829 B2 | 4/2018 | Starksen et al. |
| 10,092,402 B2 | 10/2018 | Starksen et al. |
| 10,542,987 B2 * | 1/2020 | Nguyen .......... A61B 17/064 |
| 10,624,741 B2 | 4/2020 | Starksen et al. |
| 2001/0005787 A1 | 6/2001 | Oz et al. |
| 2001/0014800 A1 | 8/2001 | Frazier et al. |
| 2001/0023332 A1 | 9/2001 | Hahnen |
| 2001/0031979 A1 | 10/2001 | Ricci |
| 2001/0034528 A1 | 10/2001 | Foerster et al. |
| 2001/0041821 A1 | 11/2001 | Wilk |
| 2002/0013571 A1 | 1/2002 | Goldfarb et al. |
| 2002/0013621 A1 | 1/2002 | Stobie et al. |
| 2002/0026201 A1 | 2/2002 | Foerster et al. |
| 2002/0029080 A1 | 3/2002 | Mortier et al. |
| 2002/0035361 A1 | 3/2002 | Houser et al. |
| 2002/0042621 A1 | 4/2002 | Liddicoat et al. |
| 2002/0065536 A1 | 5/2002 | Hart et al. |
| 2002/0072757 A1 | 6/2002 | Ahmed et al. |
| 2002/0077524 A1 | 6/2002 | Schweich, Jr. et al. |
| 2002/0087048 A1 | 7/2002 | Brock et al. |
| 2002/0087049 A1 | 7/2002 | Brock et al. |
| 2002/0087148 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 | 7/2002 | Brock et al. |
| 2002/0138044 A1 | 9/2002 | Streeter et al. |
| 2002/0156526 A1 | 10/2002 | Hlavka et al. |
| 2002/0161378 A1 | 10/2002 | Downing |
| 2002/0165486 A1 | 11/2002 | Bertolero et al. |

(56) References Cited

U.S. PATENT DOCUMENTS

| | | |
|---|---|---|
| 2002/0165561 A1 | 11/2002 | Ainsworth et al. |
| 2002/0173841 A1 | 11/2002 | Ortiz et al. |
| 2002/0183787 A1 | 12/2002 | Wahr et al. |
| 2002/0183835 A1 | 12/2002 | Taylor et al. |
| 2002/0193815 A1 | 12/2002 | Foerster et al. |
| 2003/0009196 A1 | 1/2003 | Peterson |
| 2003/0014060 A1 | 1/2003 | Wilson |
| 2003/0018358 A1 | 1/2003 | Saadat |
| 2003/0032979 A1 | 2/2003 | Mortier et al. |
| 2003/0033006 A1 | 2/2003 | Phillips et al. |
| 2003/0060813 A1 | 3/2003 | Loeb et al. |
| 2003/0069593 A1 | 4/2003 | Tremulis et al. |
| 2003/0074012 A1 | 4/2003 | Nguyen et al. |
| 2003/0078465 A1 | 4/2003 | Pai et al. |
| 2003/0078601 A1 | 4/2003 | Shikhman et al. |
| 2003/0078603 A1 | 4/2003 | Schaller et al. |
| 2003/0093118 A1 | 5/2003 | Ho et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0130731 A1 | 7/2003 | Vidlund et al. |
| 2003/0144697 A1 | 7/2003 | Mathis et al. |
| 2003/0158464 A1 | 8/2003 | Bertolero |
| 2003/0158581 A1 | 8/2003 | Levinson |
| 2003/0167062 A1 | 9/2003 | Gambale et al. |
| 2003/0167071 A1 | 9/2003 | Martin et al. |
| 2003/0199974 A1 | 10/2003 | Lee et al. |
| 2003/0220685 A1 | 11/2003 | Hlvaka et al. |
| 2003/0225420 A1 | 12/2003 | Wardle |
| 2003/0233105 A1 | 12/2003 | Gayton |
| 2003/0233142 A1 | 12/2003 | Morales et al. |
| 2003/0236535 A1 | 12/2003 | Onuki et al. |
| 2004/0003819 A1 | 1/2004 | St. Goar et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0092962 A1 | 5/2004 | Thornton et al. |
| 2004/0093024 A1 | 5/2004 | Lousararian et al. |
| 2004/0097788 A1 | 5/2004 | Mourlas et al. |
| 2004/0122450 A1 | 6/2004 | Oren et al. |
| 2004/0152947 A1 | 8/2004 | Schroeder et al. |
| 2004/0162465 A1 | 8/2004 | Carrillo |
| 2004/0172046 A1 | 9/2004 | Hlavka et al. |
| 2004/0181238 A1 | 9/2004 | Zarbatany et al. |
| 2004/0186378 A1 | 9/2004 | Gesswein |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0236372 A1 | 11/2004 | Anspach et al. |
| 2004/0236419 A1 | 11/2004 | Milo |
| 2004/0243227 A1 | 12/2004 | Starksen et al. |
| 2005/0021054 A1 | 1/2005 | Ainsworth et al. |
| 2005/0055052 A1 | 3/2005 | Lombardo et al. |
| 2005/0055087 A1 | 3/2005 | Starksen |
| 2005/0065550 A1 | 3/2005 | Starksen et al. |
| 2005/0065589 A1 | 3/2005 | Schneider et al. |
| 2005/0075723 A1 | 4/2005 | Schroeder et al. |
| 2005/0080454 A1 | 4/2005 | Drews et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119673 A1 | 6/2005 | Gordon et al. |
| 2005/0137689 A1 | 6/2005 | Salahieh et al. |
| 2005/0177180 A1 | 8/2005 | Kaganov et al. |
| 2005/0184122 A1 | 8/2005 | Hlavka et al. |
| 2005/0192599 A1 | 9/2005 | Demarais |
| 2005/0192629 A1 | 9/2005 | Saadat et al. |
| 2005/0197694 A1 | 9/2005 | Pai et al. |
| 2005/0209690 A1 | 9/2005 | Mathis et al. |
| 2005/0216078 A1 | 9/2005 | Starksen et al. |
| 2005/0228452 A1 | 10/2005 | Mourlas et al. |
| 2005/0251157 A1 | 11/2005 | Saadat et al. |
| 2005/0251159 A1 | 11/2005 | Ewers et al. |
| 2005/0251166 A1 | 11/2005 | Vaughan et al. |
| 2005/0251177 A1 | 11/2005 | Saadat et al. |
| 2005/0251205 A1 | 11/2005 | Ewers et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267495 A1 | 12/2005 | Ginn et al. |
| 2005/0273138 A1 | 12/2005 | To et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0015144 A1 | 1/2006 | Burbank et al. |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0122633 A1 | 6/2006 | To et al. |
| 2006/0129188 A1 | 6/2006 | Starksen et al. |
| 2006/0161040 A1 | 7/2006 | McCarthy et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0241656 A1 | 10/2006 | Starksen et al. |
| 2006/0264975 A1 | 11/2006 | Pipenhagen et al. |
| 2006/0271101 A1 | 11/2006 | Saadat et al. |
| 2006/0282161 A1 | 12/2006 | Huynh et al. |
| 2006/0287661 A1 | 12/2006 | Bolduc et al. |
| 2007/0005081 A1 | 1/2007 | Findlay et al. |
| 2007/0005394 A1 | 1/2007 | Bleyendaal et al. |
| 2007/0010857 A1 | 1/2007 | Sugimoto et al. |
| 2007/0032820 A1 | 2/2007 | Chin-Chen et al. |
| 2007/0038293 A1 | 2/2007 | Goar et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0112244 A1 | 5/2007 | McCarthy et al. |
| 2007/0112422 A1 | 5/2007 | Dehdashtian |
| 2007/0112424 A1 | 5/2007 | Spence et al. |
| 2007/0112425 A1 | 5/2007 | Schaller et al. |
| 2008/0045977 A1 | 2/2008 | To et al. |
| 2008/0045982 A1 | 2/2008 | To et al. |
| 2008/0045983 A1 | 2/2008 | To et al. |
| 2008/0051810 A1 | 2/2008 | To et al. |
| 2008/0051832 A1 | 2/2008 | To et al. |
| 2008/0051837 A1 | 2/2008 | To et al. |
| 2008/0058765 A1 | 3/2008 | Jais et al. |
| 2008/0058868 A1 | 3/2008 | To et al. |
| 2008/0172035 A1 | 7/2008 | Starksen et al. |
| 2008/0177380 A1 | 7/2008 | Starksen et al. |
| 2008/0228032 A1 | 9/2008 | Starksen et al. |
| 2008/0234701 A1 | 9/2008 | Morales et al. |
| 2008/0234702 A1 | 9/2008 | Morales et al. |
| 2008/0234704 A1 | 9/2008 | Starksen et al. |
| 2008/0234728 A1 | 9/2008 | Starksen et al. |
| 2008/0234815 A1 | 9/2008 | Starksen |
| 2008/0243150 A1 | 10/2008 | Starksen et al. |
| 2008/0294177 A1 | 11/2008 | To et al. |
| 2008/0312712 A1 | 12/2008 | Penner |
| 2009/0054824 A1 | 2/2009 | Melsheimer et al. |
| 2009/0182417 A1 | 7/2009 | Tremulis et al. |
| 2009/0222083 A1 | 9/2009 | Nguyen et al. |
| 2009/0234318 A1* | 9/2009 | Loulmet .......... A61B 17/00234 604/500 |
| 2009/0276038 A1 | 11/2009 | Tremulis et al. |
| 2010/0049213 A1 | 2/2010 | Serina et al. |
| 2010/0076548 A1 | 3/2010 | Konno |
| 2010/0082098 A1 | 4/2010 | Starksen et al. |
| 2010/0094248 A1 | 4/2010 | Nguyen et al. |
| 2010/0094314 A1 | 4/2010 | Hernlund et al. |
| 2010/0121349 A1 | 5/2010 | Meier et al. |
| 2010/0198192 A1 | 8/2010 | Serina et al. |
| 2011/0160528 A1 | 6/2011 | Starksen |
| 2012/0101442 A1 | 4/2012 | Legaspi et al. |
| 2012/0271331 A1 | 10/2012 | To et al. |
| 2013/0304093 A1 | 11/2013 | Serina et al. |
| 2014/0135799 A1 | 5/2014 | Henderson |

(56) References Cited

U.S. PATENT DOCUMENTS

| | | |
|---|---|---|
| 2014/0148849 A1 | 5/2014 | Eugene et al. |
| 2014/0155783 A1 | 6/2014 | Starksen et al. |
| 2014/0188140 A1 | 7/2014 | Meier et al. |
| 2014/0303649 A1 | 10/2014 | Nguyen et al. |
| 2015/0164639 A1 | 6/2015 | Starksen et al. |
| 2015/0182216 A1 | 7/2015 | Morales et al. |
| 2018/0154111 A1 | 6/2018 | Nguyen et al. |
| 2019/0091023 A1 | 3/2019 | Starksen et al. |

FOREIGN PATENT DOCUMENTS

| | | |
|---|---|---|
| EP | 0 669 101 A1 | 8/1995 |
| GB | 1370546 A | 10/1974 |
| JP | 6-510460 A | 11/1994 |
| JP | 11-506628 A | 6/1999 |
| JP | 2004-601 A | 1/2004 |
| JP | 2007-514455 A | 6/2007 |
| JP | 48-23295 B2 | 11/2011 |
| WO | WO-93/08740 A1 | 5/1993 |
| WO | WO-94/03227 A1 | 2/1994 |
| WO | WO-95/15715 A1 | 6/1995 |
| WO | WO-96/08208 A1 | 3/1996 |
| WO | WO-96/39081 A1 | 6/1996 |
| WO | WO-96/39942 A1 | 12/1996 |
| WO | WO-97/27799 A1 | 8/1997 |
| WO | WO-97/27807 A1 | 8/1997 |
| WO | WO-97/30639 A1 | 8/1997 |
| WO | WO-98/07375 A1 | 2/1998 |
| WO | WO-00/60995 A2 | 10/2000 |
| WO | WO-00/60995 A3 | 10/2000 |
| WO | WO-00/67640 A2 | 11/2000 |
| WO | WO-00/67640 A3 | 11/2000 |
| WO | WO-01/26586 A1 | 4/2001 |
| WO | WO-01/54618 A1 | 8/2001 |
| WO | WO-02/03892 A1 | 1/2002 |
| WO | WO-02/034167 A2 | 5/2002 |
| WO | WO-02/034167 A3 | 5/2002 |
| WO | WO-02/051329 A1 | 7/2002 |
| WO | WO-02/053011 A2 | 7/2002 |
| WO | WO-02/053011 A3 | 7/2002 |
| WO | WO-02/085251 A1 | 10/2002 |
| WO | WO-02/085252 A1 | 10/2002 |
| WO | WO-03/053289 A1 | 7/2003 |
| WO | WO-03/088875 A1 | 10/2003 |
| WO | WO-03/105667 A2 | 12/2003 |
| WO | WO-03/105667 A3 | 12/2003 |
| WO | WO-03/105670 A2 | 12/2003 |
| WO | WO-03/105670 A3 | 12/2003 |
| WO | WO-2004/037317 A2 | 5/2004 |
| WO | WO-2004/037317 A3 | 5/2004 |
| WO | WO-2004/082523 A2 | 9/2004 |
| WO | WO-2004/082523 A3 | 9/2004 |
| WO | WO-2004/082538 A2 | 9/2004 |
| WO | WO-2004/082538 A3 | 9/2004 |
| WO | WO-2005/025644 A2 | 3/2005 |
| WO | WO-2005/025644 A3 | 3/2005 |
| WO | WO-2005/062931 A2 | 7/2005 |
| WO | WO-2005/062931 A3 | 7/2005 |
| WO | WO-2005/102181 A1 | 11/2005 |
| WO | WO-2006/037073 A2 | 4/2006 |
| WO | WO-2006/037073 A3 | 4/2006 |
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2007/001936 A2 | 1/2007 |
| WO | WO-2007/001936 A3 | 1/2007 |
| WO | WO-2007/005495 A1 | 1/2007 |
| WO | WO-2007/021564 A1 | 2/2007 |
| WO | WO-2007/021834 A1 | 2/2007 |
| WO | WO-2007/035449 A2 | 3/2007 |
| WO | WO-2007/035449 A3 | 3/2007 |
| WO | WO-2007/056502 A1 | 5/2007 |
| WO | WO-2007/100409 A2 | 9/2007 |
| WO | WO-2007/100409 A3 | 9/2007 |
| WO | WO-2008/028135 A2 | 3/2008 |
| WO | WO-2008/028135 A3 | 3/2008 |
| WO | WO-2009/100242 A2 | 8/2009 |
| WO | WO-2009/100242 A3 | 8/2009 |
| WO | WO-2012/031204 A2 | 3/2012 |
| WO | WO-2012/031204 A3 | 3/2012 |
| WO | WO-2013112944 A1 | 8/2013 |
| WO | WO-2014183178 A1 | 11/2014 |

OTHER PUBLICATIONS

De Simone, R. et al. (Apr. 1, 1994). "Adjustable Annuloplasty for Tricuspid Insufficiency with External Control," *Reader's Comments and Reply, Am. J. Cardiol.* 73(9):721-722.

Downing, S.W. et al. (2002). "Feasibility of Off-Pump ASD Closure Using Real-Time 3-D Echocardiography," *The Heart Surgery Forum* 5(2):96-99, Abstract 7025.

European Examination Communication mailed on Dec. 8, 2009, for EP Application No. 06 837 222.6 filed on Nov. 8, 2006, 3 pages.

Extended European Search Report mailed on Sep. 9, 2011, for EP Patent Application No. 11158896.8, filed on Sep. 1, 2004, 7 pages.

Extended European Search Report mailed on Sep. 16, 2011, for EP Patent Application No. 11158898.4, filed on Sep. 1, 2004, 8 pages.

Extended European Search Report mailed on Jan. 21, 2019, for EP Patent Application No. 16793570.9, filed on May 12, 2016, 9 Pages.

Extended European Search Report mailed on Dec. 12, 2018, for EP Patent Application No. 18170269.7, filed on Sep. 1, 2004, 7 Pages.

Final Office Action mailed on Feb. 6, 2007, for U.S. Appl. No. 10/656,797, filed Sep. 4, 2003, 8 pages.

Final Office Action mailed on Jul. 12, 2007, for U.S. Appl. No. 11/202,474, filed Aug. 11, 2005, 10 pages.

Final Office Action mailed on Jul. 24, 2007, for U.S. Appl. No. 10/741,130, filed Dec. 19, 2003, 10 pages.

Final Office Action mailed on Aug. 6, 2007, for U.S. Appl. No. 10/901,019, filed Jul. 27, 2004, 12 pages.

Final Office Action mailed on Aug. 6, 2007, for U.S. Appl. No. 11/137,833, filed May 24, 2005, 8 pages.

Final Office Action mailed on Aug. 13, 2007, for U.S. Appl. No. 10/900,980, filed Jul. 27, 2004, 9 pages.

Final Office Action mailed on Aug. 14, 2007, for U.S. Appl. No. 11/255,400, filed Oct. 20, 2005, 8 pages.

Final Office Action mailed on Aug. 30, 2007, for U.S. Appl. No. 11/232,190, filed Sep. 20, 2005, 9 pages.

Final Office Action mailed on Oct. 30, 2007, for U.S. Appl. No. 10/656,797, filed Sep. 4, 2003, 6 pages.

Final Office Action mailed on Apr. 2, 2008, for U.S. Appl. No. 10/792,681, filed Mar. 2, 2004, 15 pages.

Final Office Action mailed on Apr. 14, 2008, for U.S. Appl. No. 10/901,019, filed Jul. 27, 2004, 11 pages.

Final Office Action mailed on May 28, 2008, for U.S. Appl. No. 11/270,034, filed Nov. 8, 2005, 10 pages.

Final Office Action mailed on Jun. 4, 2008, for U.S. Appl. No. 11/202,474, filed Aug. 11, 2005, 10 pages.

Final Office Action mailed on Aug. 1, 2008, for U.S. Appl. No. 11/232,190, filed Sep. 20, 2005, 8 pages.

Final Office Action mailed on Sep. 30, 2008, for U.S. Appl. No. 10/900,980, filed Jul. 27, 2004, 7 pages.

Final Office Action mailed on Oct. 14, 2008, for U.S. Appl. No. 10/741,130, filed Dec. 19, 2003, 9 pages.

Final Office Action mailed on Jan. 22, 2009, for U.S. Appl. No. 11/255,400, filed Oct. 20, 2005, 9 pages.

Final Office Action mailed on Mar. 11, 2009, for U.S. Appl. No. 10/656,797, filed Sep. 4, 2003, 10 pages.

Final Office Action mailed on Apr. 10, 2009, for U.S. Appl. No. 11/414,657, filed Apr. 27, 2006, 8 pages.

Final Office Action mailed on Apr. 10, 2009, for U.S. Appl. No. 11/255,400, filed Oct. 20, 2005, 8 pages.

Final Office Action mailed on Apr. 29, 2009, for U.S. Appl. No. 10/901,019, filed Jul. 27, 2004, 9 pages.

Final Office Action mailed on Jul. 21, 2009, for U.S. Appl. No. 11/270,034, filed Nov. 8, 2005, 8 pages.

Final Office Action mailed on Sep. 2, 2009, for U.S. Appl. No. 11/232,190, filed Sep. 20, 2005, 8 pages.

(56) References Cited

OTHER PUBLICATIONS

Final Office Action mailed on Sep. 28, 2009, for U.S. Appl. No. 11/202,474, filed Aug. 11, 2005, 10 pages.
Final Office Action mailed on Oct. 13, 2009, for U.S. Appl. No. 10/901,554, filed Jul. 27, 2004, 11 pages.
Final Office Action mailed on Nov. 10, 2009, for U.S. Appl. No. 10/741,130, filed Dec. 19, 2003, 9 pages.
Final Office Action mailed on Mar. 3, 2010, for U.S. Appl. No. 11/414,657, filed Apr. 27, 2006, 7 pages.
Final Office Action mailed on Mar. 25, 2010, for U.S. Appl. No. 10/900,980, filed Jul. 27, 2004, 8 pages.
Final Office Action mailed on Jun. 8, 2010, for U.S. Appl. No. 10/792,681, filed Mar. 2, 2004, 17 pages.
Final Office Action mailed on Jul. 26, 2010, for U.S. Appl. No. 11/270,034, filed Nov. 8, 2005, 8 pages.
Final Office Action mailed on Sep. 15, 2010, for U.S. Appl. No. 11/894,401, filed Aug. 20, 2007, 6 pages.
Final Office Action mailed on Oct. 6, 2010, for U.S. Appl. No. 12/132,375, filed Jun. 3, 2008, 9 pages.
Final Office Action mailed on Nov. 26, 2010, for U.S. Appl. No. 11/894,340, filed Aug. 20, 2007, 12 pages.
Final Office Action mailed on Nov. 29, 2010, for U.S. Appl. No. 11/894,463, filed Aug. 20, 2007, 12 pages.
Final Office Action mailed on Feb. 24, 2011, for U.S. Appl. No. 11/894,397, filed Aug. 20, 2007, 12 pages.
Final Office Action mailed on Feb. 24, 2011, for U.S. Appl. No. 11/894,468, filed Aug. 20, 2007, 12 pages.
Final Office Action mailed on Mar. 17, 2011, for U.S. Appl. No. 10/901,554, filed Jul. 27, 2004, 13 pages.
Final Office Action mailed on Mar. 17, 2011, for U.S. Appl. No. 11/202,474, filed Aug. 11, 2005, 9 pages.
Final Office Action mailed on Apr. 20, 2011, for U.S. Appl. No. 11/414,657, filed Apr. 27, 2006, 8 pages.
Final Office Action mailed on Nov. 10, 2011, for U.S. Appl. No. 10/792,681, filed Mar. 2, 2004, 20 pages.
Final Office Action mailed on Aug. 4, 2011, for U.S. Appl. No. 10/900,980, filed Jul. 27, 2004, 9 pages.
Final Office Action mailed on Dec. 6, 2011, for U.S. Appl. No. 12/366,553, filed Feb. 5, 2009, 7 pages.
Final Office Action mailed on Mar. 19, 2012, for U.S. Appl. No. 12/574,563, filed Oct. 6, 2009, 6 pages.
Final Office Action mailed on Apr. 15, 2016, for U.S. Appl. No. 14/309,837, filed Jun. 19, 2014, 5 pages.
Final Office Action mailed on Jun. 11, 2012, for U.S. Appl. No. 12/132,161, filed Jun. 3, 2008, 13 pages.
Final Office Action mailed on Feb. 2, 2015, for U.S. Appl. No. 13/540,499, filed Jul. 2, 2012, 10 pages.
Final Office Action mailed on Jun. 11, 2012, for U.S. Appl. No. 12/187,331, filed Jun. 6, 2008, 7 pages.
Final Office Action mailed on Feb. 4, 2016, for U.S. Appl. No. 14/626,826, filed Feb. 19, 2015, 9 pages.
Final Office Action mailed on Sep. 14, 2017, for U.S. Appl. No. 14/626,826, filed Feb. 19, 2015, 8 pages.
Final Office Action mailed on Nov. 3, 2017, for U.S. Appl. No. 13/540,499, filed Jul. 2, 2012, 10 pages.
International Search Report mailed Dec. 19, 2006, for PCT Application No. PCT/US2006/031190, filed Aug. 10, 2006, 4 pages.
International Search Report mailed on Apr. 2, 2007, for PCT Application No. PCT/US2006/043597, filed Nov. 8, 2006, 7 pages.
International Search Report mailed on Sep. 15, 2009, for PCT Patent Application No. PCT/US2009/033252, filed on Feb. 5, 2009, 1 page.
International Search Report mailed on Mar. 7, 2007, for PCT Patent Application No. PCT/US2004/028431, filed on Sep. 1, 2004, 1 page.
International Search Report and Written Opinion mailed on Aug. 18, 2016, for PCT Patent Application No. PCT/US2016/032220, filed on May 12, 2016, 6 pages.
Nagy, Z.L et al. (Dec. 2000). "Mitral Annuloplasty with a Suture Technique," *European Journal of Cardio-thoracic Surgery* 18(6):739-740.
Non-Final Office Action mailed on Aug. 9, 2006, for U.S. Appl. No. 10/900,980, filed Jul. 27, 2004, 17 pages.
Non-Final Office Action mailed on Aug. 22, 2006, for U.S. Appl. No. 10/656,797, filed Sep. 4, 2003, 6 pages.
Non-Final Office Action mailed on Nov. 15, 2006, for U.S. Appl. No. 11/137,833, filed May 24, 2005, 12 pages.
Non-Final Office Action mailed on Nov. 28, 2006, for U.S. Appl. No. 10/901,019, filed Jul. 27, 2004, 20 pages.
Non-Final Office Action mailed on Dec. 27, 2006, for U.S. Appl. No. 10/741,130, filed Dec. 19, 2003, 9 pages.
Non-Final Office Action mailed on Dec. 27, 2006, for U.S. Appl. No. 11/270,034, filed Nov. 8, 2005, 8 pages.
Non-Final Office Action mailed on Jan. 4, 2007, for U.S. Appl. No. 11/255,400, filed Oct. 20, 2005, 7 pages.
Non-Final Office Action mailed on Feb. 27, 2007, for U.S. Appl. No. 11/202,474, filed Aug. 11, 2005, 8 pages.
Non-Final Office Action mailed on Mar. 12, 2007, for U.S. Appl. No. 11/232,190, filed Sep. 20, 2005, 11 pages.
Non-Final Office Action mailed on Jul. 24, 2007, for U.S. Appl. No. 10/656,797, filed Sep. 4, 2003, 6 pages.
Non-Final Office Action mailed on Aug. 1, 2007, for U.S. Appl. No. 10/792,681, filed Mar. 2, 2004, 16 pages.
Non-Final Office Action mailed on Aug. 30, 2007, for U.S. Appl. No. 11/270,034, filed Nov. 8, 2005, 10 pages.
Non-Final Office Action mailed on Oct. 19, 2007, for U.S. Appl. No. 11/202,474, filed Aug. 11, 2005, 7 pages.
Non-Final Office Action mailed on Oct. 29, 2007, for U.S. Appl. No. 10/901,019, filed Jul. 27, 2004, 10 pages.
Non-Final Office Action mailed on Nov. 14, 2007, for U.S. Appl. No. 10/741,130, filed Dec. 19, 2003, 8 pages.
Non-Final Office Action mailed on Nov. 14, 2007, for U.S. Appl. No. 11/137,833, filed May 24, 2005, 8 pages.
Non-Final Office Action mailed on Jan. 9, 2008, for U.S. Appl. No. 11/232,190, filed Sep. 20, 2005, 8 pages.
Non-Final Office Action mailed on Jan. 31, 2008, for U.S. Appl. No. 11/255,400, filed Oct. 20, 2005, 7 pages.
Non-Final Office Action (Supplementary) mailed on May 9, 2008, for U.S. Appl. No. 11/255,400, filed Oct. 20, 2005, 7 pages.
Non-Final Office Action mailed on Mar. 27, 2008, for U.S. Appl. No. 10/900,980, filed Jul. 27, 2004, 7 pages.
Non-Final Office Action mailed on Jun. 6, 2008, for U.S. Appl. No. 10/656,797, filed Sep. 4, 2003, 5 pages.
Non-Final Office Action mailed on Aug. 29, 2008, for U.S. Appl. No. 10/792,681, filed Mar. 2, 2004, 15 pages.
Non-Final Office Action mailed on Sep. 26, 2008, for U.S. Appl. No. 11/414,657, filed Apr. 27, 2006, 11 pages.
Non-Final Office Action mailed on Oct. 24, 2008, for U.S. Appl. No. 10/901,019, filed Jul. 27, 2004, 11 pages.
Non-Final Office Action mailed on Jan. 13, 2009, for U.S. Appl. No. 10/901,555, filed Jul. 27, 2004, 11 pages.
Non-Final Office Action mailed on Jan. 23, 2009, for U.S. Appl. No. 11/232,190, filed Sep. 20, 2005, 8 pages.
Non-Final Office Action mailed on Jan. 23, 2009, for U.S. Appl. No. 11/270,034, filed Nov. 8, 2005, 8 pages.
Non-Final Office Action mailed on Jan. 29, 2009, for U.S. Appl. No. 10/900,980, filed Jul. 27, 2004, 6 pages.
Non-Final Office Action mailed on Mar. 5, 2009, for U.S. Appl. No. 11/202,474, filed Aug. 11, 2005, 10 pages.
Non-Final Office Action mailed on Mar. 18, 2009, for U.S. Appl. No. 10/901,554, filed Jul. 27, 2004, 12 pages.
Non-Final Office Action mailed on Mar. 27, 2009, for U.S. Appl. No. 10/741,130, filed Dec. 19, 2003, 9 pages.
Non-Final Office Action mailed on Mar. 31, 2009, for U.S. Appl. No. 10/792,681, filed Mar. 2, 2004, 15 pages.
Non-Final Office Action mailed on Aug. 25, 2009, for U.S. Appl. No. 10/900,980, filed Jul. 27, 2004, 7 pages.
Non-Final Office Action mailed on Aug. 26, 2009, for U.S. Appl. No. 11/414,657, filed Apr. 27, 2006, 6 pages.
Non-Final Office Action mailed on Sep. 17, 2009, for U.S. Appl. No. 10/656,797, filed Sep. 4, 2003, 13 pages.

(56) References Cited

OTHER PUBLICATIONS

Non-Final Office Action mailed on Oct. 19, 2009, for U.S. Appl. No. 10/901,019, filed Jul. 27, 2004, 21 pages.
Non-Final Office Action mailed on Jan. 19, 2010, for U.S. Appl. No. 11/270,034, filed Nov. 8, 2005, 10 pages.
Non-Final Office Action mailed on Feb. 18, 2010, for U.S. Appl. No. 11/894,401, filed Aug. 20, 2007, 6 pages.
Non-Final Office Action mailed on Mar. 16, 2010, for U.S. Appl. No. 11/894,340, filed Aug. 20, 2007, 14 pages.
Non-Final Office Action mailed on Mar. 29, 2010, for U.S. Appl. No. 11/894,463, filed Aug. 20, 2007, 14 pages.
Non-Final Office Action mailed on Apr. 2, 2010, for U.S. Appl. No. 12/132,375, filed Jun. 3, 2008, 9 pages.
Non-Final Office Action mailed on Jun. 9, 2010, for U.S. Appl. No. 11/894,468, filed Aug. 20, 2007, 14 pages.
Non-Final Office Action mailed on Jun. 21, 2010, for U.S. Appl. No. 11/894,397, filed Aug. 20, 2007, 13 pages.
Non-Final Office Action mailed on Aug. 17, 2010, for U.S. Appl. No. 11/414,657, filed Apr. 27, 2006, 7 pages.
Non-Final Office Action mailed on Aug. 20, 2010, for U.S. Appl. No. 10/901,554, filed Jul. 27, 2004, 13 pages.
Non-Final Office Action mailed on Oct. 25, 2010, for U.S. Appl. No. 11/202,474, filed Aug. 11, 2005, 8 pages.
Non-Final Office Action mailed on Oct. 29, 2010, for U.S. Appl. No. 11/894,530, filed Aug. 20, 2007, 11 pages.
Non-Final Office Action mailed on Nov. 24, 2010, for U.S. Appl. No. 10/900,980, filed Jul. 27, 2004, 8 pages.
Non-Final Office Action mailed on Feb. 2, 2011, for U.S. Appl. No. 12/581,040, filed Oct. 16, 2009, 5 pages.
Non-Final Office Action mailed on Apr. 27, 2011, for U.S. Appl. No. 12/366,533, filed Feb. 5, 2009, 9 pages.
Non-Final Office Action mailed on Jul. 29, 2011, for U.S. Appl. No. 12/574,563, filed Oct. 6, 2009, 5 pages.
Non-Final Office Action mailed on Oct. 13, 2011, for U.S. Appl. No. 12/187,331, filed Aug. 6, 2008, 5 pages.
Non-Final Office Action mailed on Dec. 22, 2011, for U.S. Appl. No. 11/270,034, filed Nov. 8, 2005, 9 pages.
Non-Final Office Action mailed on Feb. 10, 2014, for U.S. Appl. No. 12/366,553, filed Feb. 5, 2009, 7 pages.
Non-Final Office Action mailed on Apr. 8, 2013, for U.S. Appl. No. 11/414,657, filed Apr. 27, 2006, 9 pages.
Non-Final Office Action mailed on Oct. 19, 2015, for U.S. Appl. No. 14/309,837, filed Jun. 19, 2014, 6 pages.
Non-Final Office Action mailed on Nov. 24, 2015, for U.S. Appl. No. 14/156,347, filed Jan. 15, 2014, 5 pages.
Non-Final Office Action mailed on Apr. 21, 2016, for U.S. Appl. No. 13/540,499, filed Jul. 2, 2012, 13 pages.
Non-Final Office Action mailed on Feb. 17, 2017, for U.S. Appl. No. 14/626,826, filed Feb. 19, 2015, 11 pages.
Non-Final Office Action mailed on Jan. 26, 2017, for U.S. Appl. No. 13/540,499, filed Jul. 2, 2012, 10 pages.
Non-Final Office Action mailed on Mar. 28, 2019, for U.S. Appl. No. 15/652,068, filed Jul. 17, 2017, 11 pages.
Non-Final Office Action mailed on Feb. 24, 2020, for U.S. Appl. No. 15/572,757, filed Nov. 8, 2017, 6 pages.
Notice of Allowance mailed on Aug. 4, 2009, for U.S. Appl. No. 10/901,555, filed Jul. 27, 2004, 7 pages.
Notice of Allowance mailed on Feb. 24, 2010, for U.S. Appl. No. 10/656,797, filed Sep. 4, 2003, 8 pages.
Notice of Allowance mailed on Apr. 28, 2010, for U.S. Appl. No. 10/901,019, filed Jul. 27, 2004, 7 pages.
Notice of Allowance mailed on Nov. 17, 2010, for U.S. Appl. No. 11/232,190, filed Sep. 20, 2005, 11 pages.
Notice of Allowance mailed on Dec. 6, 2010, for U.S. Appl. No. 12/132,375, filed Jun. 3, 2008, 9 pages.
Notice of Allowance mailed on Jul. 26, 2011, for U.S. Appl. No. 11/894,530, filed Aug. 20, 2007, 10 pages.
Notice of Allowance mailed on Sep. 25, 2013, for U.S. Appl. No. 12/132,161, filed Jun. 3, 2008, 12 pages.
Notice of Allowance mailed on Jun. 11, 2012, for U.S. Appl. No. 10/741,130, filed Dec. 19, 2003, 9 pages.
Notice of Allowance mailed on Mar. 17, 2014, for U.S. Appl. No. 12/366,553, filed Feb. 5, 2009, 8 pages.
Notice of Allowance mailed on Oct. 29, 2015, for U.S. Appl. No. 10/901,554, filed Jul. 27, 2004, 8 pages.
Notice of Allowance mailed on Jun. 15, 2016, for U.S. Appl. No. 14/156,347, filed Jan. 15, 2014, 7 pages.
Notice of Allowance mailed on Nov. 8, 2017, for U.S. Appl. No. 13/820,447, filed Oct. 18, 2013, 8 pages.
Notice of Allowance mailed on Dec. 19, 2017, for U.S. Appl. No. 14/626,826, filed Feb. 19, 2015, 8 pages.
Notice of Allowance mailed on Mar. 2, 2015, for U.S. Appl. No. 12/187,331, filed Aug. 6, 2008, 5 pages.
Notice of Allowance mailed on Jun. 22, 2018, for U.S. Appl. No. 15/265,781, filed Sep. 14, 2016, 8 pages.
Notice of Allowance mailed on Aug. 16, 2018, for U.S. Appl. No. 15/265,781, filed Sep. 14, 2016, 7 pages.
Notice of Allowance mailed on Sep. 16, 2019, for U.S. Appl. No. 15/652,068, filed Jul. 17, 2017, 8 pages.
Notice of Allowance mailed on Feb. 24, 2020, for U.S. Appl. No. 15/955,564, filed Apr. 17, 2018, 9 pages.
Shumay, S.J. et al. (Dec. 1988). "A 'Designer' Annuloplasty Ring for Patients with Massive Mitral Annular Dilatation," *Ann. Thorac. Surg.* 46(6):695-696.
Written Opinion of the International Searching Authority mailed on Dec. 19, 2006, for PCT Application No. PCT/US2006/031190, filed Aug. 10, 2006, 6 pages.
Written Opinion of the International Searching Authority mailed on Apr. 2, 2007, for PCT Application No. PCT/US2006/043597, filed Nov. 8, 2006, 7 pages.
Supplementary European Search Report mailed on Nov. 10, 2008, for EP Application No. 04 78 2847, filed on Sep. 1, 2004, 2 pages.
Written Opinion of the International Searching Authority mailed on Sep. 19, 2009, for PCT Patent Application No. PCT/US2009/033252, filed on Feb. 5, 2009, 7 pages.
Written Opinion of the International Searching Authority mailed on Mar. 7, 2007, for PCT Patent Application No. PCT/US2004/028431, filed on Sep. 1, 2004, 4 pages.
U.S. Appl. No. 11/875,774, filed Oct. 19, 2007, by Serina et al. (Copy not attached).
Extended European Search Report in European Application No. EP22155112.0, dated Sep. 19, 2022, 12 Pages.
Final Office Action in U.S. Appl. No. 15/572,757, mailed Sep. 3, 2020, 6 pages.
Non-Final Office Action in U.S. Appl. No. 17/157,635, mailed Feb. 16, 2023, 8 pages.
Notice of Allowance in U.S. Appl. No. 15/572,757, mailed on Dec. 23, 2020, 8 pages.

* cited by examiner

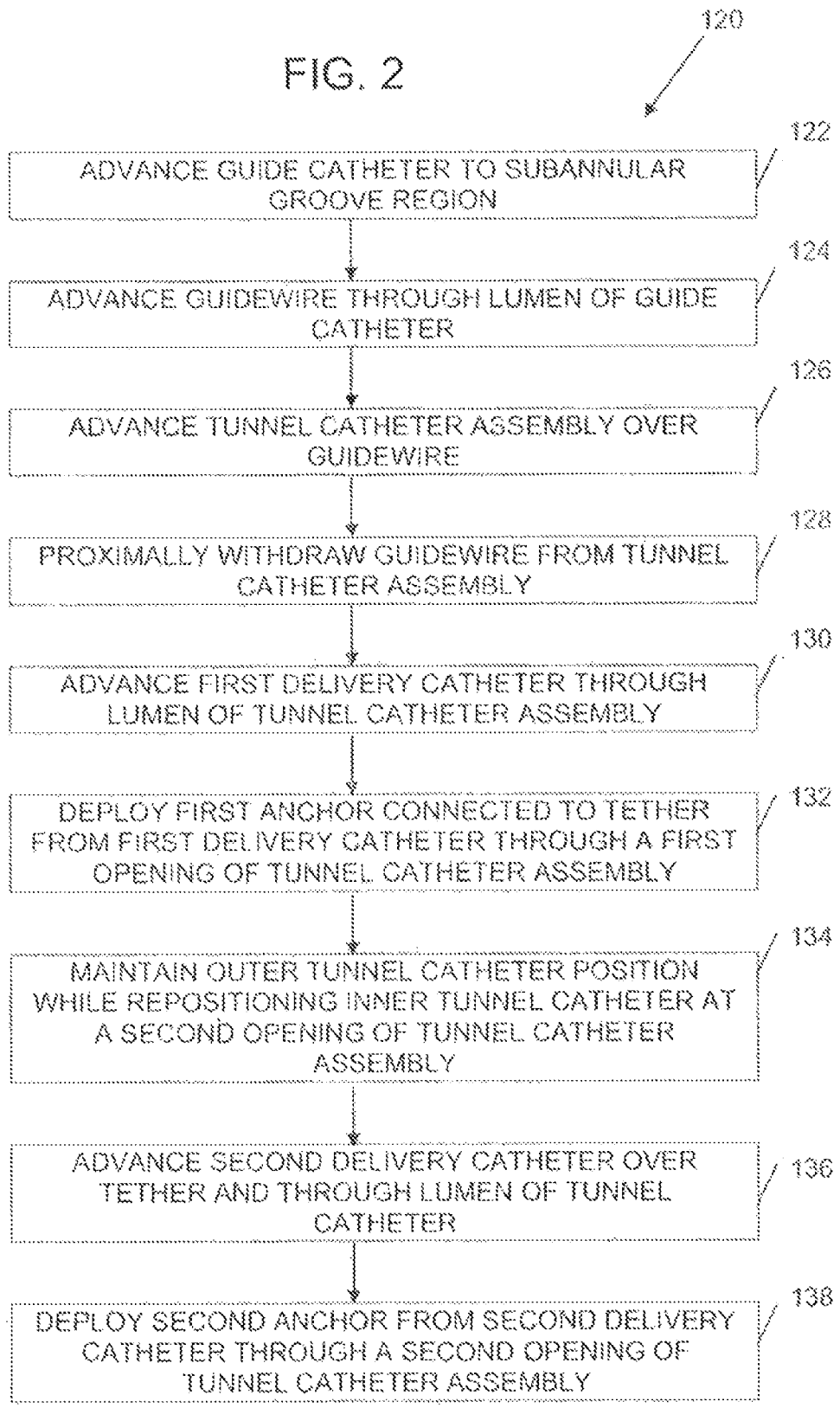

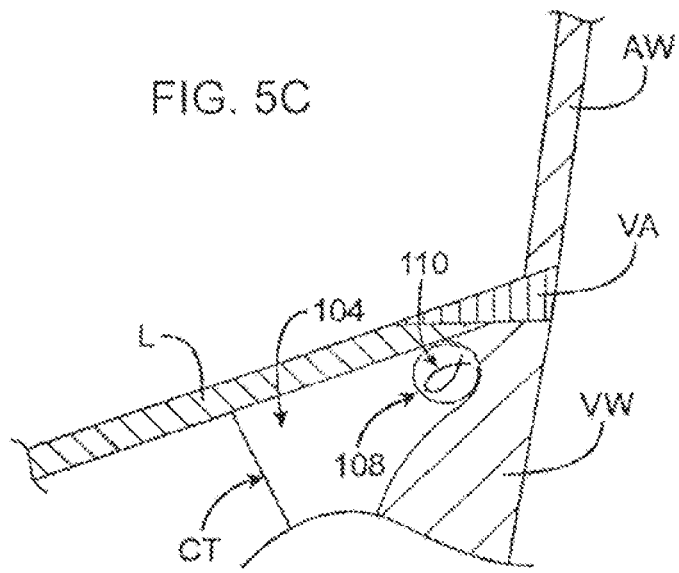
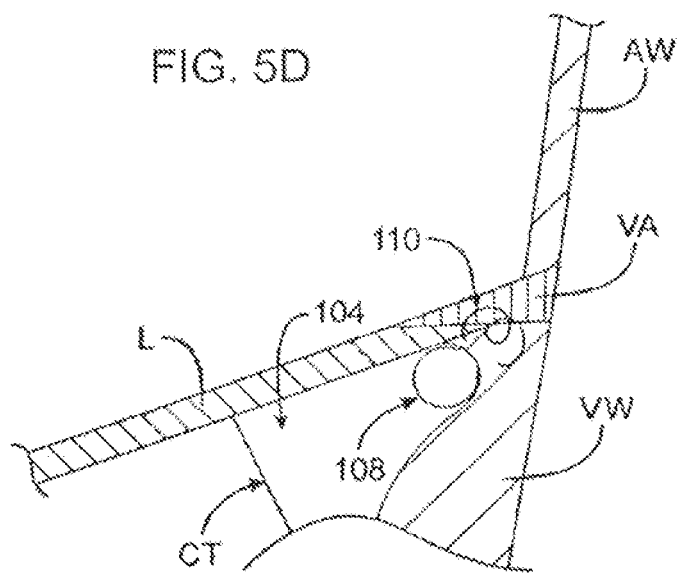

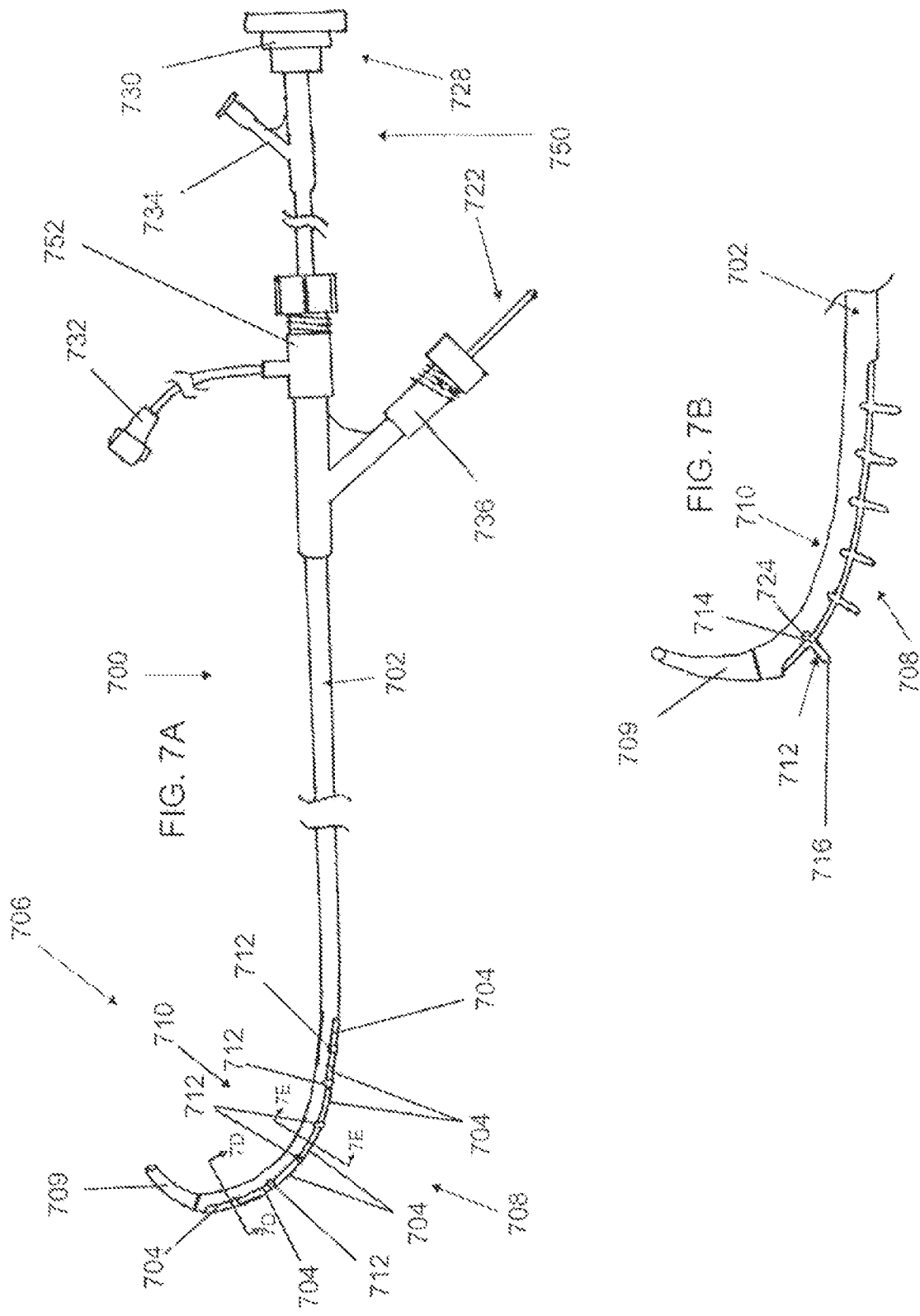

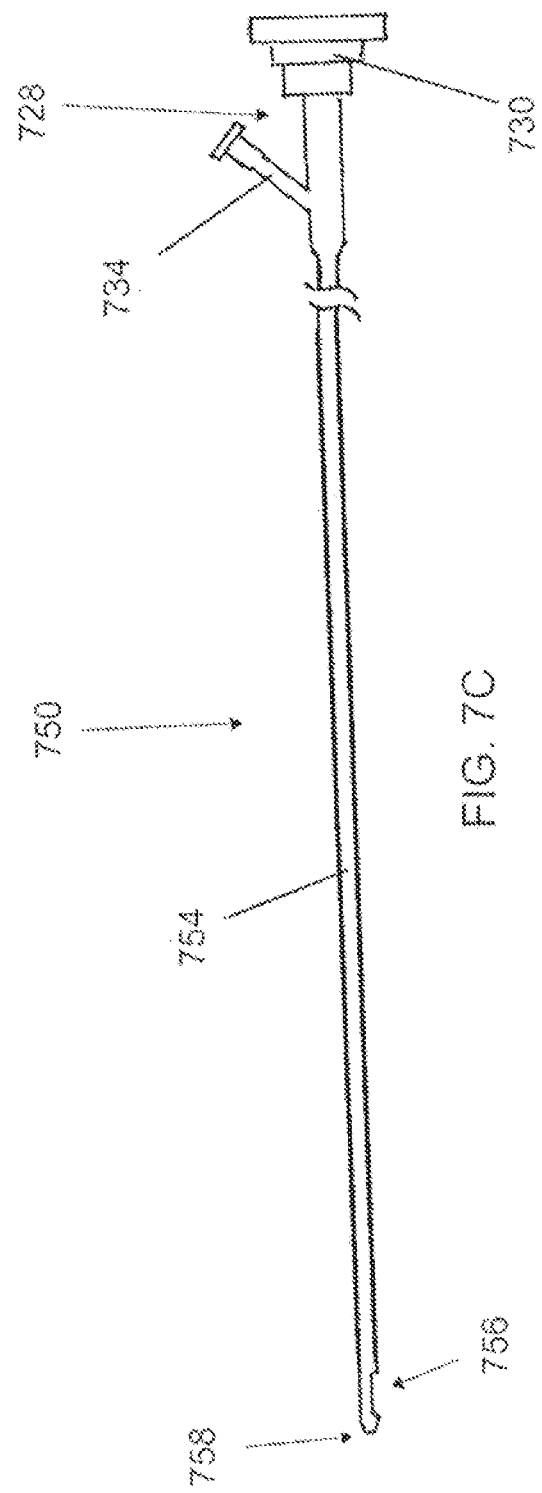

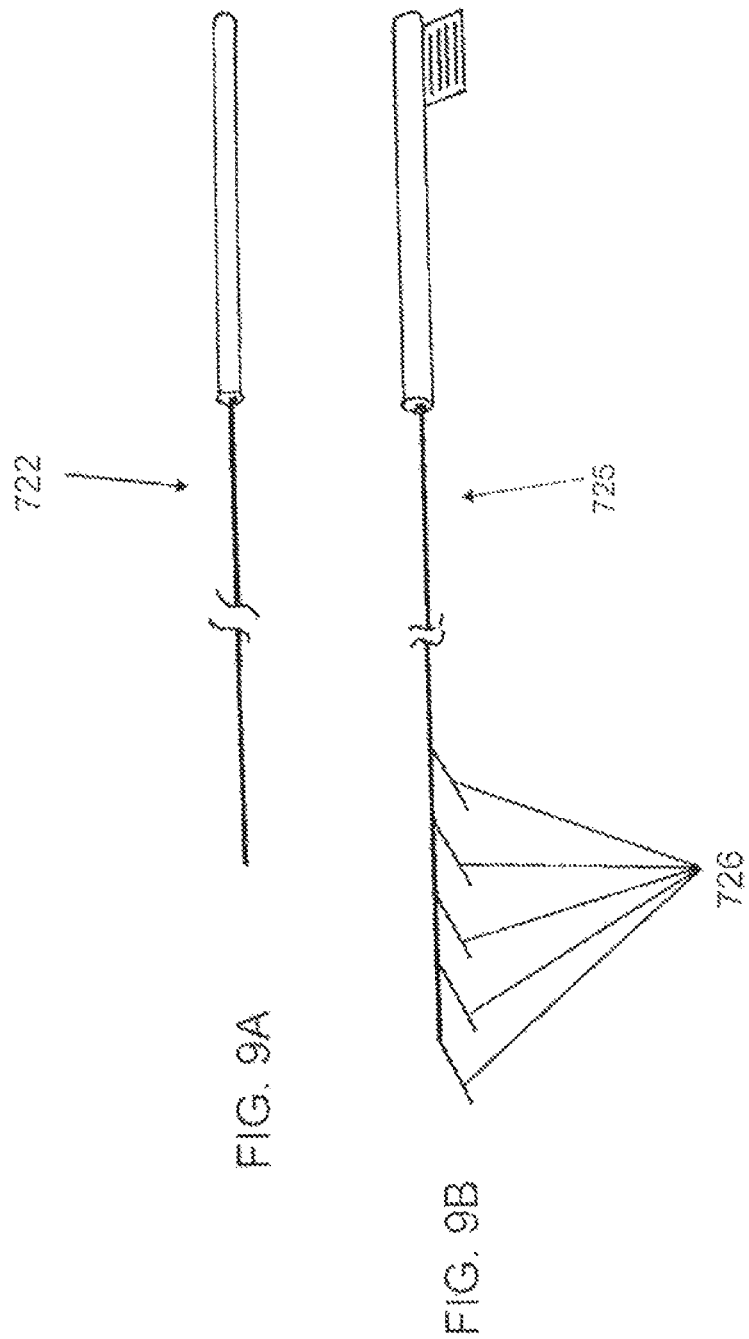

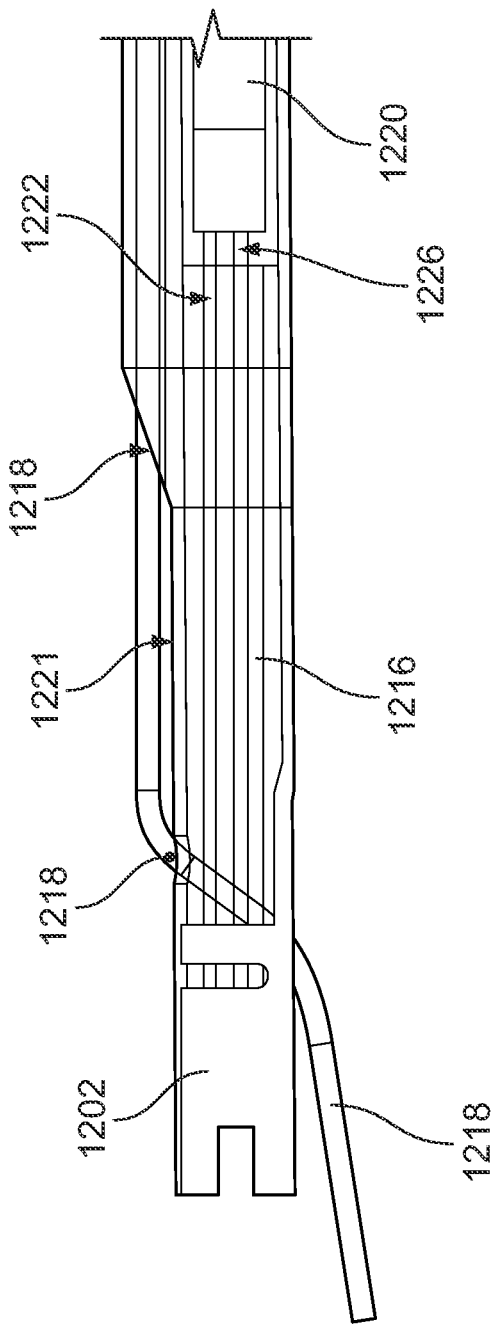
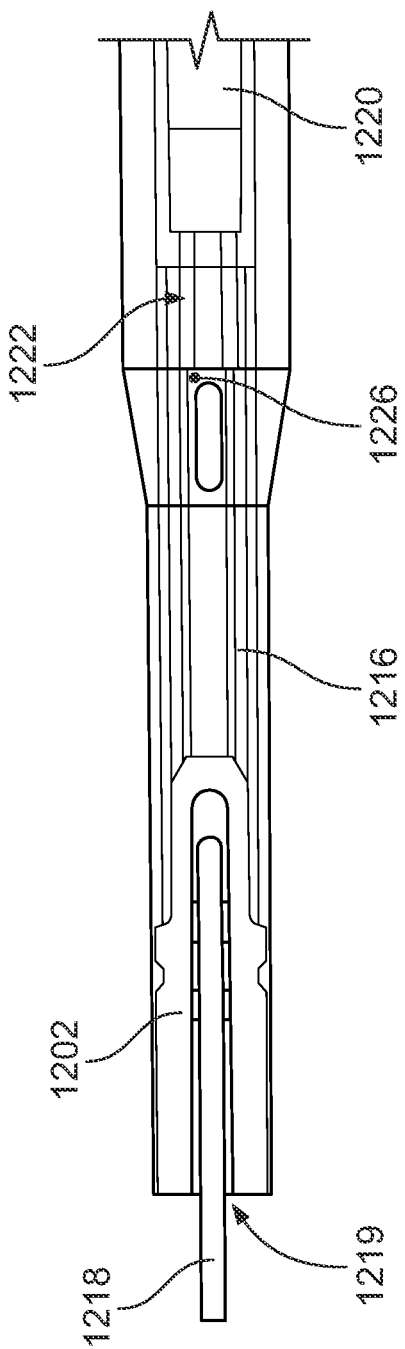
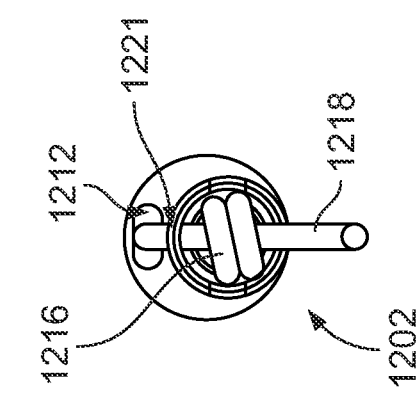

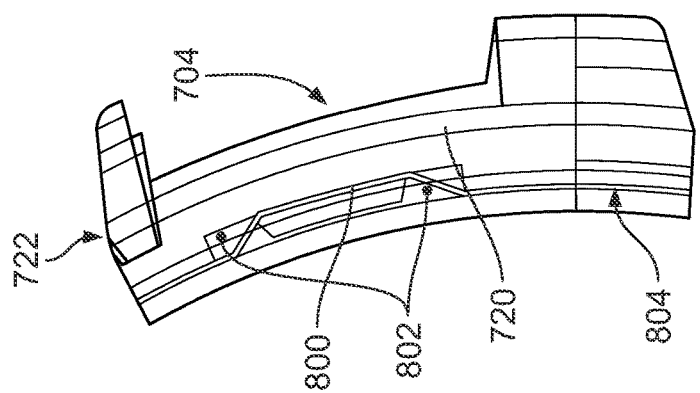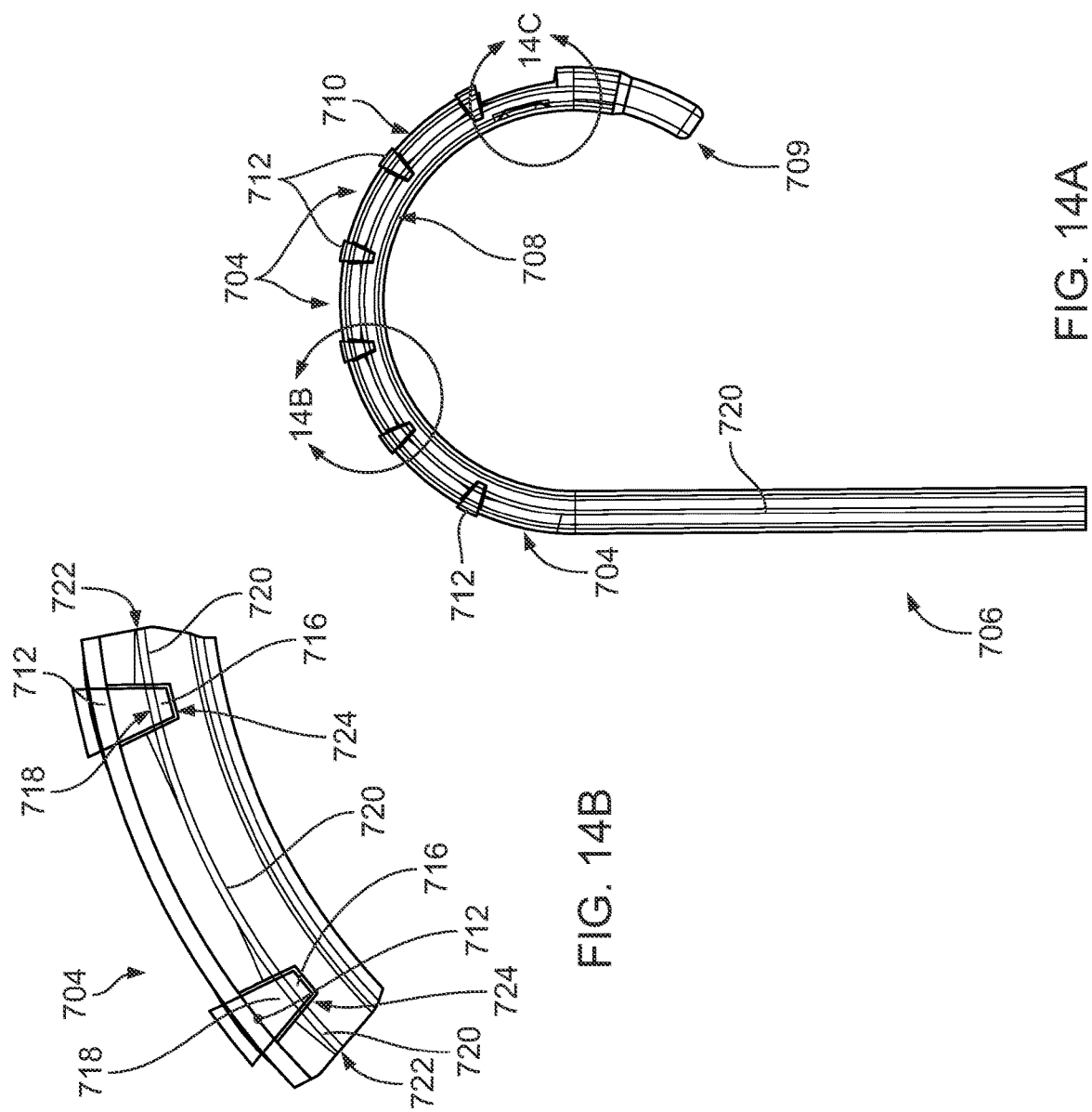

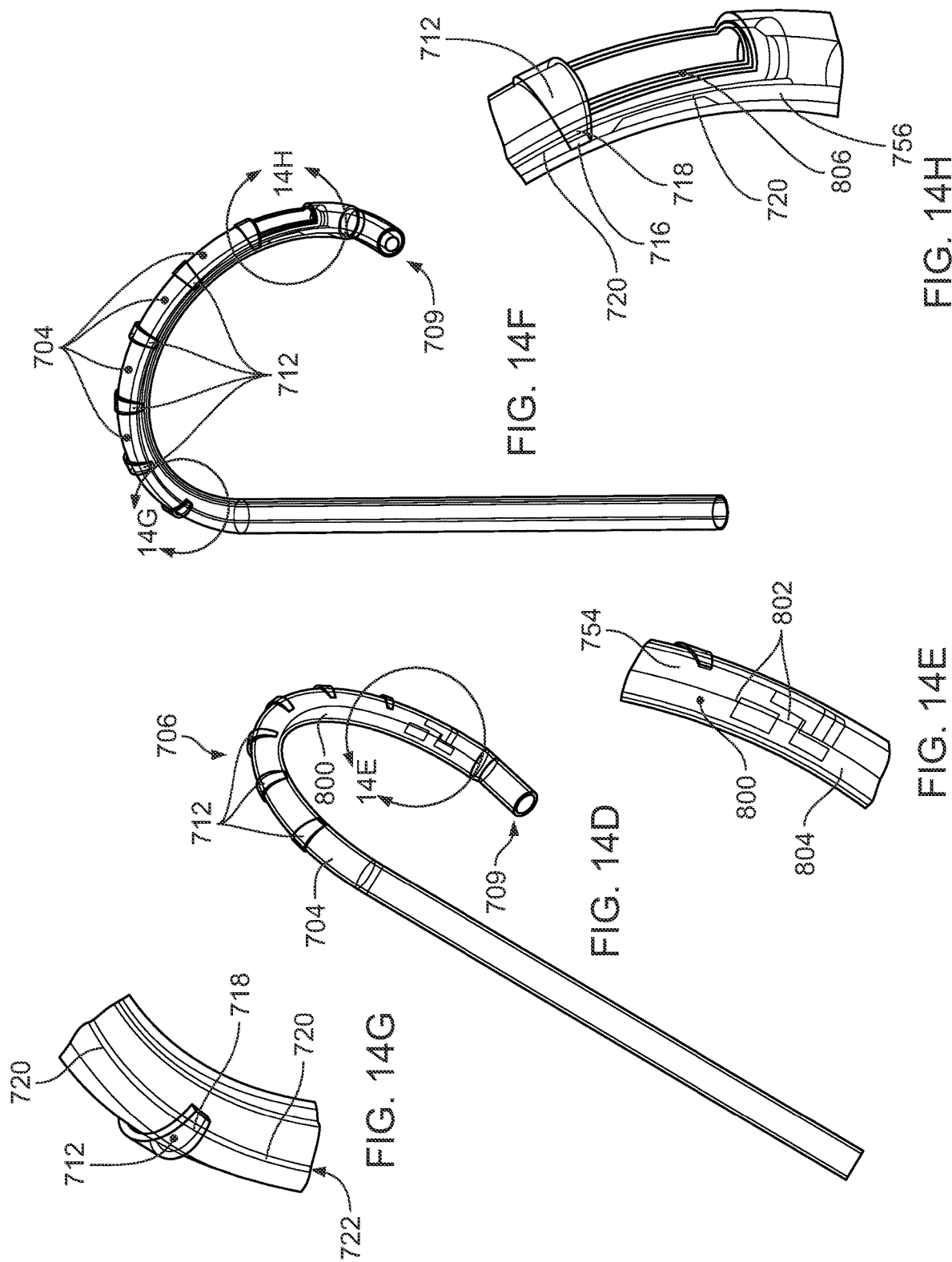

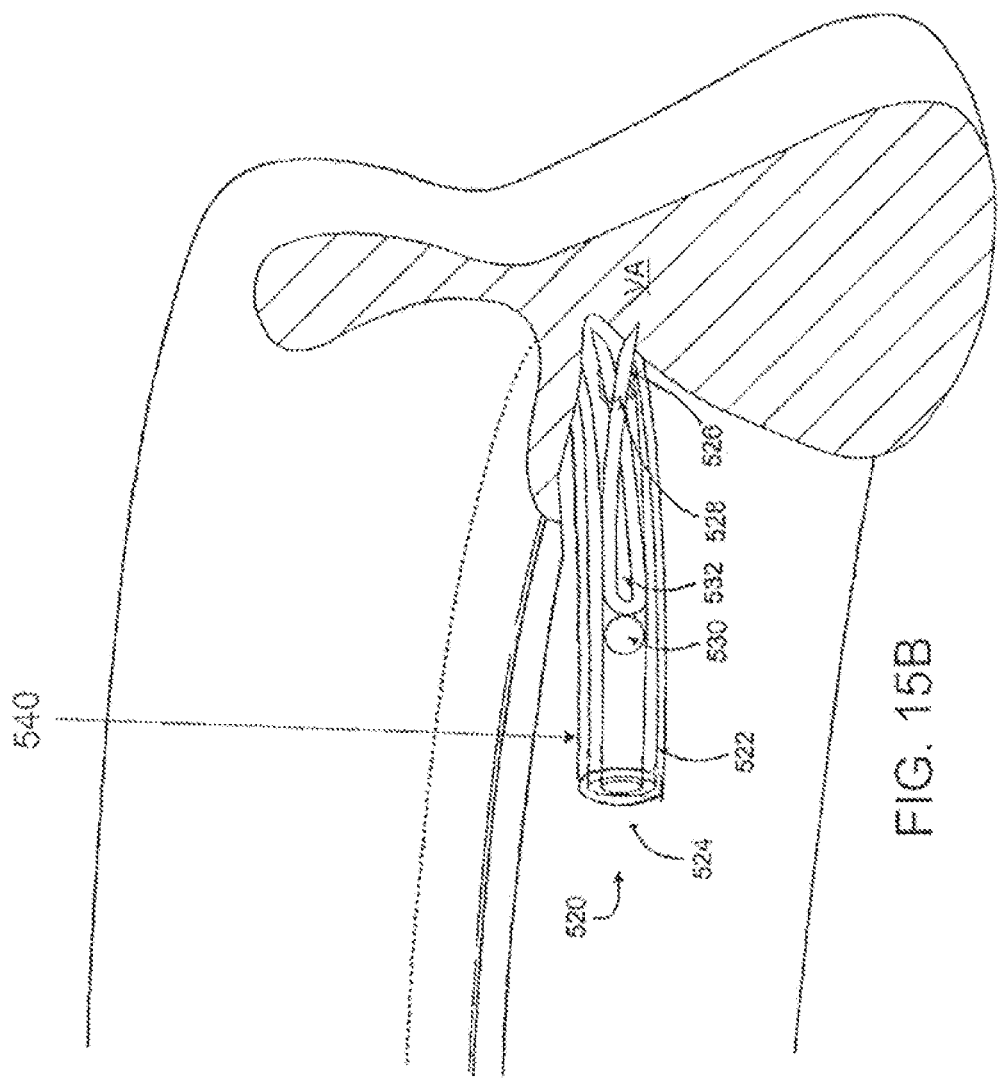

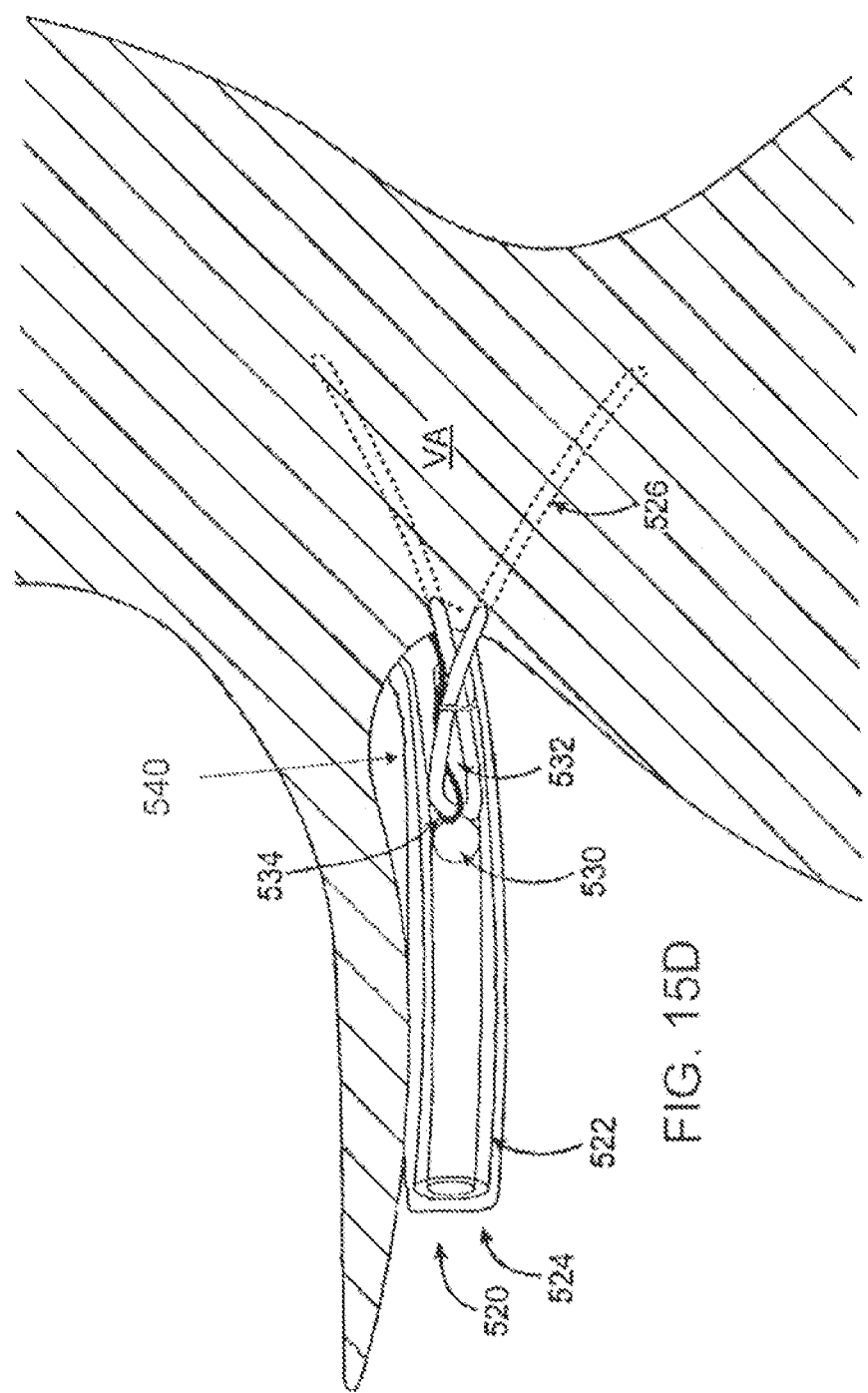

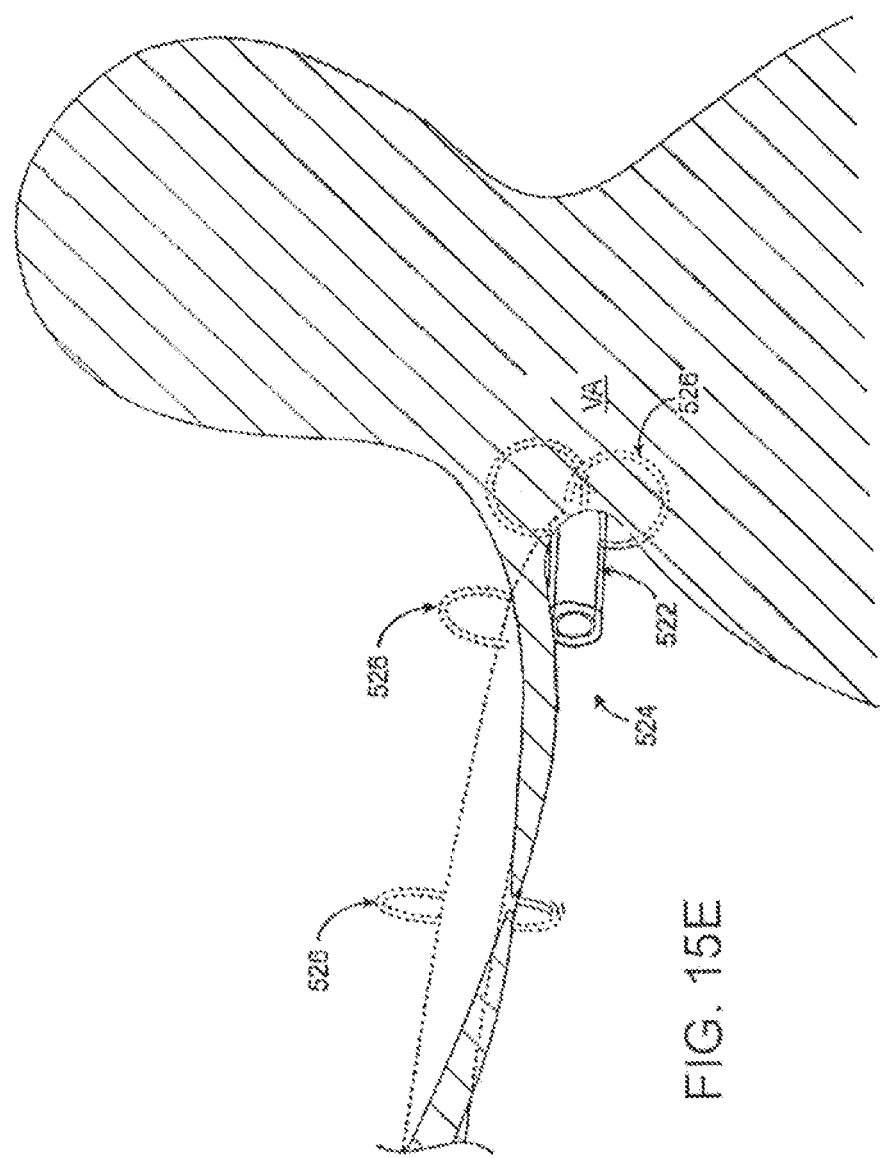

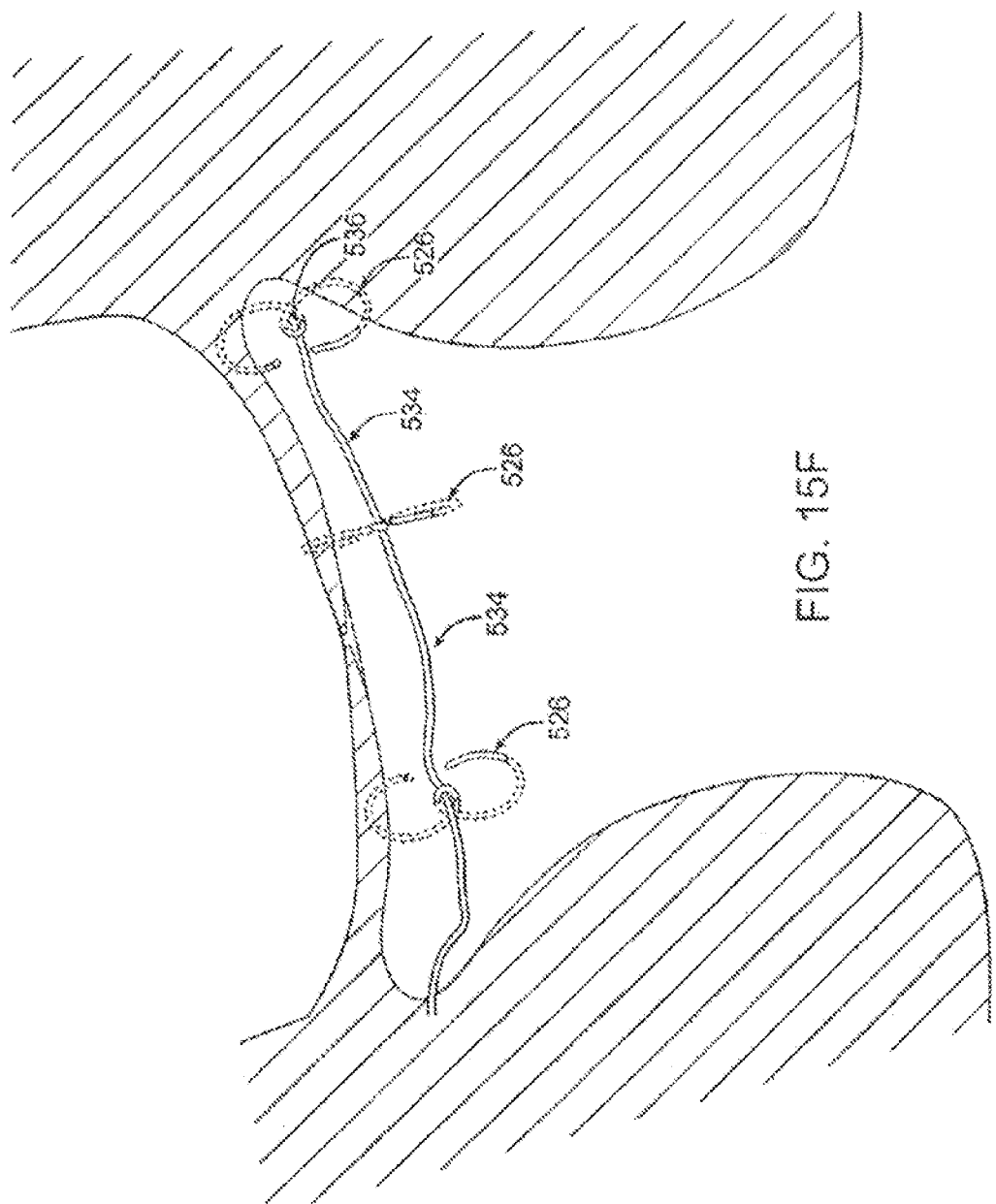

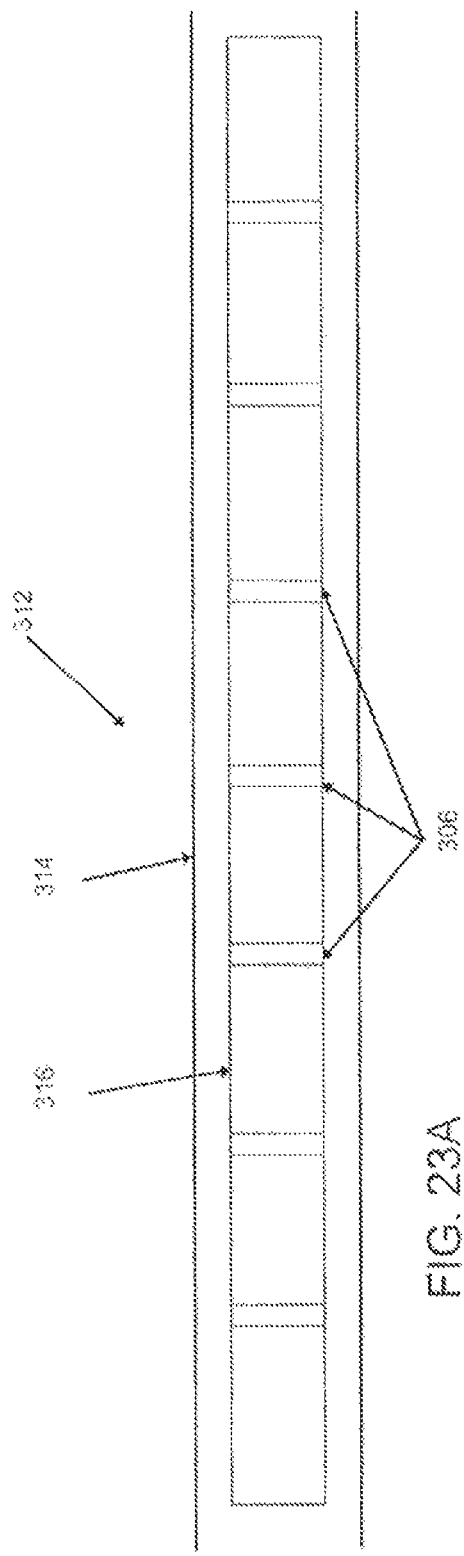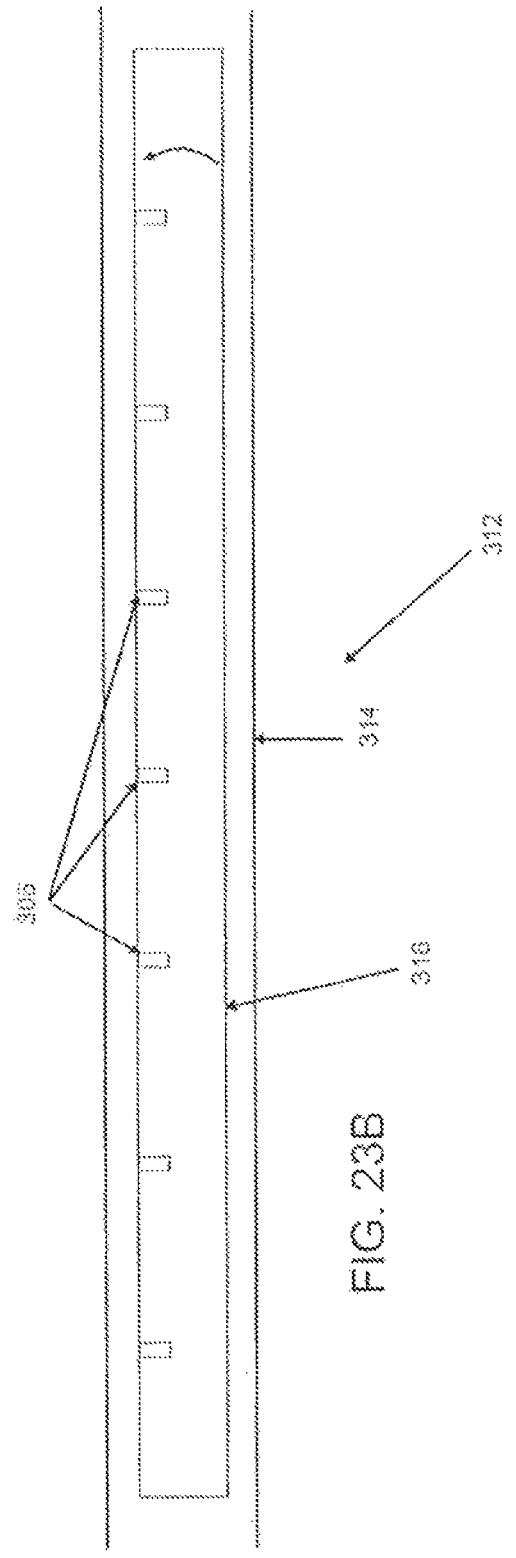
FIG. 23A
FIG. 23B

MULTI-WINDOW GUIDE TUNNEL

CROSS-REFERENCE TO RELATED APPLICATIONS

The present application is a continuation of Ser. No. 15/652,068, filed Jul. 17, 2017, now issued U.S. Pat. No. 10,542,987, which is a continuation application of U.S. application Ser. No. 14/309,837, filed Jun. 19, 2014, now issued U.S. Pat. No. 9,706,996, which is a continuation application of U.S. application Ser. No. 12/366,553, filed Feb. 5, 2009, now issued U.S. Pat. No. 8,790,367, which claims priority under 35 U.S.C. § 119(e) to U.S. Provisional Application No. 61/026,697, filed Feb. 6, 2008, the contents of each of which are hereby incorporated by reference in their entirety.

BACKGROUND OF THE INVENTION

Blood returning to the heart from the peripheral circulation and the lungs generally flows into the atrial chambers of the heart and then to the ventricular chambers, which pump the blood back out of the heart. During ventricular contraction, the atrio-ventricular valves between the atria and ventricles, i.e. the tricuspid and mitral valves, close to prevent backflow or regurgitation of blood from the ventricles back to the atria. The closure of these valves, along with the aortic and pulmonary valves, maintains the uni-directional flow of blood through the cardiovascular system. Disease of the valvular apparatus can result in valve dysfunction, where some fraction of the ventricular blood regurgitates back into the atrial chambers.

Traditional treatment of heart valve stenosis or regurgitation, such as mitral or tricuspid regurgitation, involves an open-heart surgical procedure to replace or repair the valve. Current accepted treatments of the mitral and tricuspid valves include: valvuloplasty, in which the affected leaflets are remodeled to perform normally; repair of the chordae tendineae and/or papillary muscle attachments; and surgical insertion of an "annuloplasty" ring, which requires suturing a flexible support ring over the annulus to constrict the radial dimension. Other surgical techniques to treat heart valve dysfunction involve fastening (or stapling) the valve leaflets to each other or to other regions of the valve annulus to improve valve function (see, e.g., U.S. Pat. No. 6,575,971).

BRIEF SUMMARY OF THE INVENTION

Described herein are devices and methods that involve attachment sites, including implants with multiple coupled anchors. The anchors may be secured to tissue using a multi-opening guide tunnel that is configured to releasably retain one or more portions of the implant located between two anchors, such as a tether component that attach the anchors. The releasable retention of one or more interconnecting portions of the implant provides additional stabilization for the delivery tool until the implant is secured to the tissue. The multi-opening guide tunnel permits securement of the multiple anchors without requiring repositioning of the guide tunnel for each anchor. In some embodiments, the multi-opening guide tunnel comprises disengageable wall segments between the openings of the guide tunnel, which provide structural support and column strength in a region of the guide tunnel that would buckle or collapse due to the number of openings and their configuration.

In some embodiments, a system for use in a patient is provided, comprising an outer catheter, which comprises a passageway with a proximal end, a distal end, a longitudinal axis and two or more outer openings, and at least one releasable retaining structure located between the two or more outer openings. At least one releasable retaining structure may be adapted to open a release channel between two or more outer openings. In some instances, at least two of the two or more outer openings are two adjacent outer openings with a separation distance less than a maximum dimension of one of the two adjacent outer openings, and at least one releasable retaining structure is located between the two adjacent outer openings. In some variations, two or more outer openings are longitudinally spaced along a longitudinal length of the outer catheter, and may be configured for passage of a tissue anchor. At least one releasable retaining structure may be configured to retain a tether attached to the tissue anchor, and is optionally an outer wall structure of the outer catheter. The outer catheter may comprise at least three outer openings, and optionally at least two releasable retaining structures. The system may further comprise an inner catheter slidably located in the passageway of the outer catheter, and sometimes may further comprise an alignment interface between the outer catheter and the inner catheter. The alignment interface may comprise a rail, which may be a metallic material and/or may be secured to the outer catheter at two or more securing sites. The outer catheter may also further comprise a curved configuration having a lesser curvature and a greater curvature, and in some embodiments, two or more openings may be generally located along the greater curvature of the outer catheter. The outer catheter may also comprise an atraumatic tip. The catheter may further comprise at least one radio-opaque structure located between the two or more outer openings. The inner catheter may comprise an inner opening and wherein the inner guide and outer guide are configured to permit positioning of the inner opening at two or more outer openings. In some embodiments, at least one releasable retaining structure comprises a locking passage. The at least one locking element may be configured for removable positioning in the locking passage of at least one releasable retaining structure, and at least two releasable retaining structures with locking passages are both optionally configured for removable positioning by one of the at least one locking elements.

In other embodiments, an implant delivery system is provided, comprising a catheter body which comprises a proximal end, a distal end, a longitudinal lumen therebetween, a lumenal surface, an ablumenal surface, and at least one implant delivery opening in communication with the longitudinal lumen and located between the luminal surface and the ablumenal surface, and at least two longitudinally-spaced retention members located distal to the proximal end of the catheter body. In some instances, at least two longitudinally-spaced retention members are located within the longitudinal lumen, or within the at least one implant delivery opening. At least two longitudinally-spaced retention members may have a transverse orientation with respect to the longitudinal lumen. In some embodiments, at least two longitudinally-spaced retention members are movable retention members, which may be rotatable or flexible retention members. The movable retention members may each comprise a through lumen. The implant delivery system may further comprise a first anchor coupled to a tether, and in some instances at least two longitudinally-spaced retention members are configured to retain the tether.

In another embodiment, a method for securing anchors to a body structure is provided, comprising providing an implant comprising a first anchor, a second anchor, and a first coupling portion therebetween, passing the first anchor and the second anchor into a common lumen of a catheter, deploying the first anchor through a first opening of the catheter, deploying the second anchor through a second opening of the catheter, retaining the first coupling portion of the implant in the catheter, wherein the first coupling portion is located between two anchors secured to the body structure, and releasing the first coupling portion of the implant from the catheter after securing the first anchor and the second anchor to body tissue. The method may further comprise positioning the catheter in a subvalvular space of a ventricle. In some instances, releasing the first coupling portion of the implant from the catheter may comprise disengaging a wall section of the catheter.

BRIEF DESCRIPTION OF THE DRAWINGS

The structure and method of using the invention will be better understood with the following detailed description of embodiments of the invention, along with the accompanying illustrations, in which:

FIG. 2 is a flowchart representation of a method for delivering at least two anchors into a subvalvular region;

FIGS. 5A to 5D are cross-sectional views of a portion of a heart, schematically illustrating the positioning and deployment of a flexible device for treatment of a mitral valve annulus;

FIG. 7A depicts one embodiment of a multi-opening guide tunnel; FIG. 7B depicts the multi-opening guide tunnel of FIG. 7A with its latches unlocked and separated from the body of the guide tunnel; FIG. 7C illustrates one embodiment of an inner guide tunnel usable with the multi-opening guide tunnel of FIG. 7A.

FIGS. 9A and 9B are schematic illustrations of various locking wire embodiments;

FIG. 13B is a frontal view of the delivery catheter of FIG. 13A, and FIGS. 13C and 13D are side and bottom views, respectively, of a portion of the delivery catheter of FIG. 13A;

FIGS. 14A to 14H are various perspective views of one embodiment of a multi-opening guide tunnel;

FIGS. 15A to 15F schematically demonstrate a method for applying anchors from the subvalvular space;

FIGS. 23A and 23B represent still another embodiment of a guide tunnel;

DETAILED DESCRIPTION OF THE INVENTION

Although a number of surgically implanted ventricular devices and procedures, such as the implantation of an annuloplasty ring or edge-to-edge leaflet repair, are available for treating valvular dysfunction, each procedure presents its own set of risks to the patient or technical challenges to the physician. For example, the ability to accurately and reliably position a cardiac implant during a beating heart procedure, whether by open chest or minimally invasive access, remains elusive to the average practitioner. In particular, the percutaneous or transvascular implantation of a ventricular device described herein poses a significant challenge due to the instability from the wall motion of a beating heart.

Devices, systems and methods of the instant invention are generally used to reshape atrio-ventricular valves or myocardium to improve hemodynamic performance. The implantation procedures are preferably transvascular, minimally invasive or other "less invasive" surgical procedures, but can also be performed with open or limited access surgical procedures. When used for treatment of a cardiac valve dysfunction, the methods generally involve positioning one or more anchor delivery devices at a target site using a guide tunnel, delivering a plurality of slidably coupled anchors from the delivery device(s), and drawing the anchors together to tighten the annulus. The devices include an elongate catheter with a housing at or near the distal end for releasably housing one or more anchors, as well as guide devices for facilitating advancement and/or positioning of an anchor delivery device. The devices may be positioned such that the housing abuts or is close to valve annular tissue, such as the region within the upper left ventricle bound by the left ventricular wall, a mitral valve leaflet and chordae tendineae. Self-securing anchors having any of a number of different configurations may be used in some embodiments.

Figure 1:
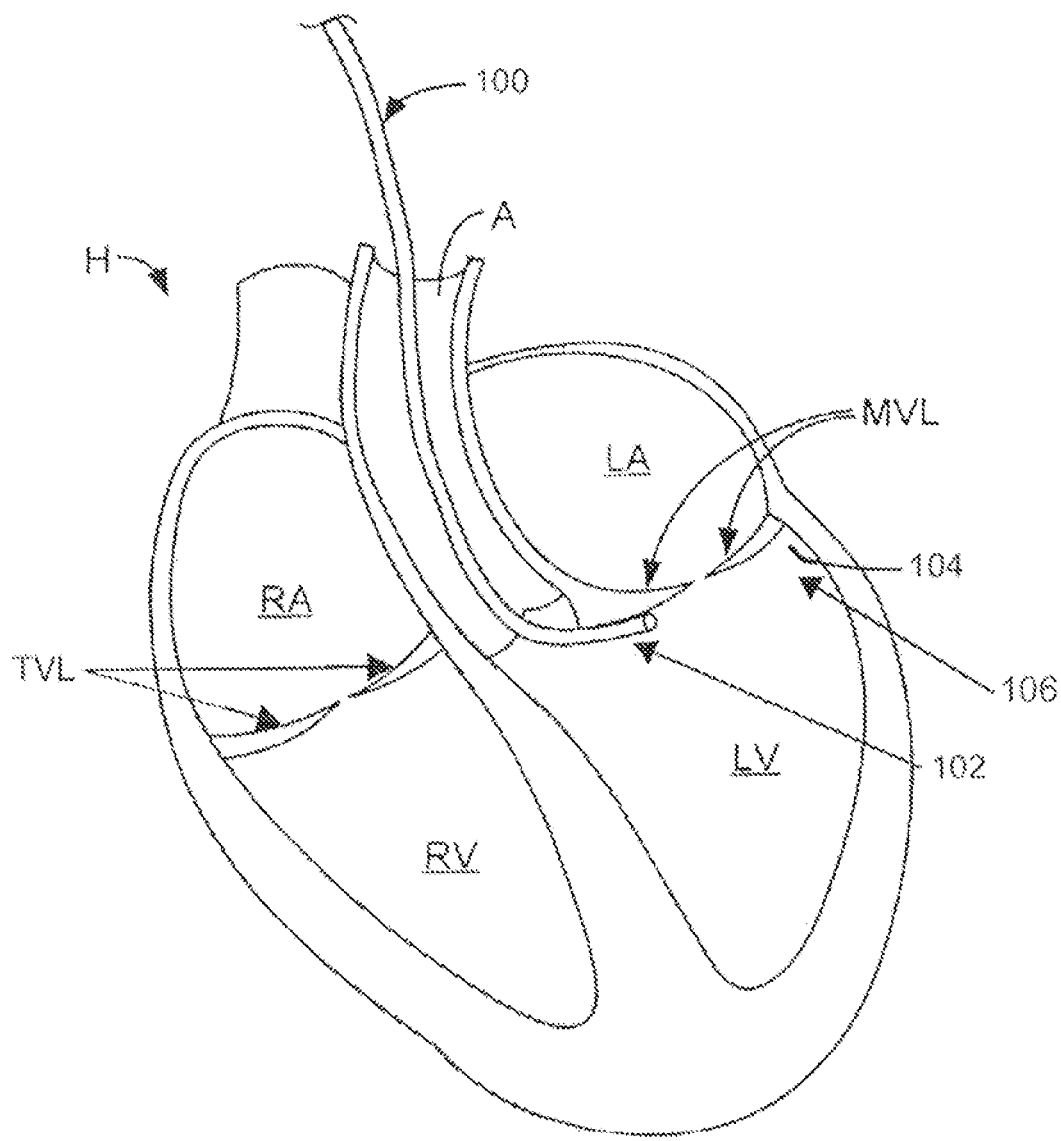
FIG. 1 is a cross-sectional view of a heart with a guide catheter device advanced through the aorta into the left ventricle.

In FIG. 1, a cross-sectional depiction of a heart H is shown with one embodiment of a guide catheter 100 advanced in a retrograde direction through the aorta A and into the left ventricle LV. Retrograde, as used herein, generally refers to a direction opposite the expected flow of blood. This access route is used to reach the subvalvular space 106. Guide catheter 100 is generally a flexible elongate catheter which may have one or more curves or bends toward its distal end to facilitate placement of the distal end 102 of the catheter 100 at the desired location. The subvalvular space, as used herein, generally includes the portion of the ventricular chamber that is bound peripherally by the ventricular wall, superiorly by the atrio-ventricular valve leaflets, and centrally by the primary chordae tendineae, and is located along the circumference of the valve annulus. The subannular groove region, as used herein, includes the space bordered by the inner surface of the ventricular wall, the inferior surface of valve leaflets L, and the third order chordae tendineae CT connected directly to the ventricular wall VW and the leaflet L. The distal end 102 of guide catheter 100 may be configured to be positioned at an opening into the subvalvular space 106 or within the subvalvular space 106, such that subsequent delivery devices may be passed through guide catheter 100 into the subvalvular space 106. Although the retrograde aortic access route preferably starts from a percutaneous or peripheral access site, in some embodiments, aortic access may be achieved by an incision in the ascending aorta, descending aorta, aortic arch or iliac arteries, following surgical, thoracoscopic or laparoscopic access to a body cavity.

Figure 19:
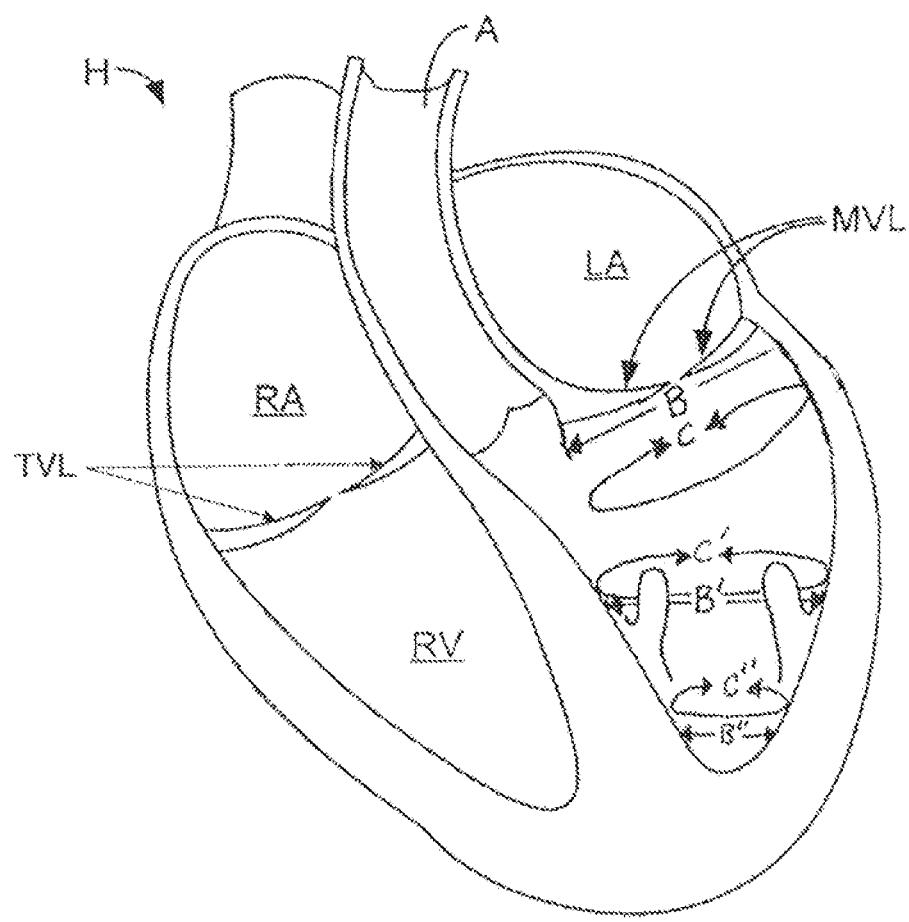
FIG. 19 is a schematic view of the heart illustrating various dimensions of a heart chamber.
Figure 20:
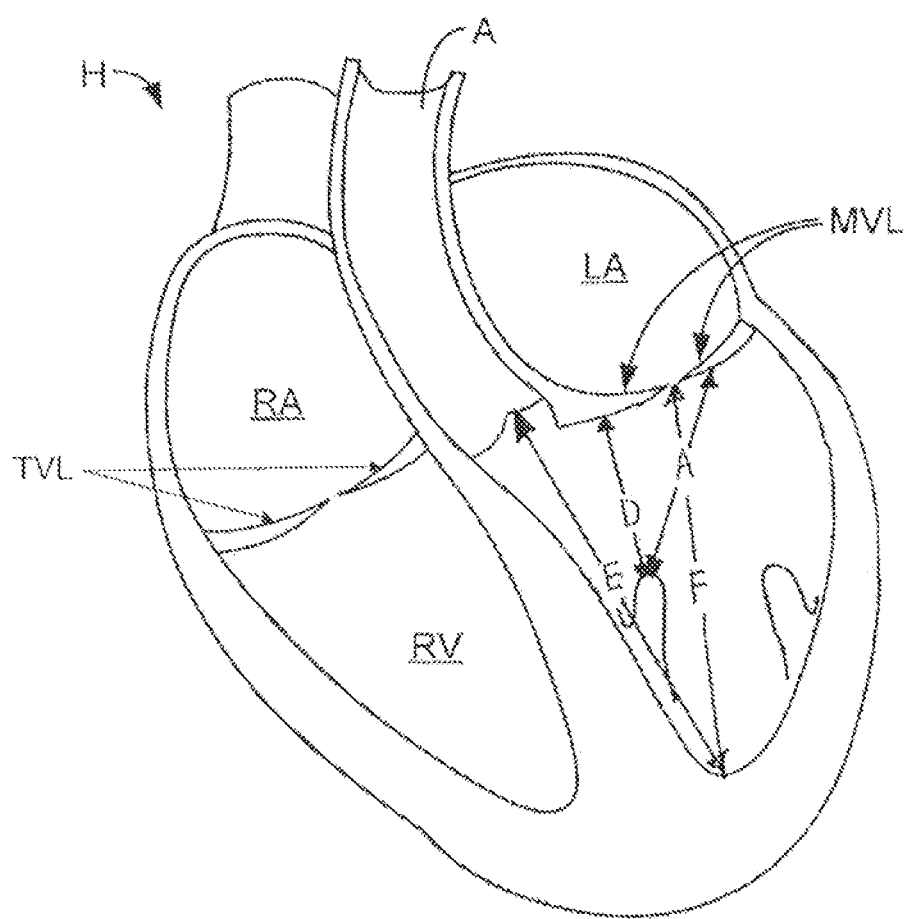
FIG. 20 is schematic view of the heart illustrating various dimensions of a heart chamber.

In other embodiments of the invention, other spaces bound by or relating to one or more cardiac structures may be used as a target region of the heart. These structures include but are not limited to the base of the ventricle, the mitral valve, the tricuspid valve, the primary chordae tendineae, the secondary chordae tendineae, the tertiary chordae tendineae, the anterior mitral valve leaflet chordae tendineae, the posterior mitral valve leaflet chordae tendineae, the interleaflet chordae tendineae, the papillary muscle, the anterior-lateral papillary muscle, the posterior-medial papillary muscle, the ventricular apical region, and the ventricular apex. For example, in some embodiments, a supra-apical space from about the base of the mitral valve leaflets to the just above the ventricular apex or apical region may be the target region. In another example, the target region may be the peri-papillary muscle region, which includes the space about 1 cm above and about 1 cm below the level of the papillary muscle region, as well as the spaces between the papillary muscles. In some examples, the target region may be the endocardial surface abutting or accessible from the given space or cardiac structures. In still other embodiments, the target region may be a region between the base and apex of a ventricle and between longitudinal borders drawn through the papillary muscles, e.g. either a posterior-lateral or an anterior-medial ventricular endocardial surface. In other embodiments, the target region may exclude the space along the longitudinal axis from the base of a ventricle to the apex of the ventricle, e.g. the target region may be tubular or toroidal in configuration, with an internal border relating to a chordae tendineae. Other examples of target regions are depicted in FIGS. 19 and 20, and are discussed in greater detail below.

FIG. 2 provides a flowchart depiction of one method 120 for deploying at least two anchors of the implant in the region of a heart valve annulus. As shown there, this illustrative method comprises advancing a guide catheter to the subannular groove region 122, advancing a guidewire through a lumen of the guide catheter 124, advancing a guide tunnel or tunnel catheter over the guidewire 126, and proximally withdrawing the guidewire from the tunnel catheter 128. In this particular embodiment, the tunnel catheter comprises an outer catheter with a passageway in which an inner catheter slidably resides. After the guidewire has been proximally withdrawn, a first delivery catheter may be advanced through the lumen of the tunnel catheter 130 and a first anchor may be deployed into a first region of the heart valve annular tissue 132. The first anchor is typically coupled or secured to a guide element, such as a tether. In this way, after the first anchor is secured to heart tissue, the guide element will remain coupled to the first anchor. While the guide element may be used as a track or monorail for the advancement of additional delivery catheters thereover, the guide element is also a component of the implant that interconnects the multiple anchors. A portion of the guide element facilitates the tightening of the implant and remains in the body with the anchors after the delivery system is removed from the body.

The guide element may be made from any suitable or desirable biocompatible material. The guide element may be braided or not braided, woven or not woven, reinforced or impregnated with additional materials, or may be made of a single material or a combination of materials. For example, the guide element may be made from (1) a suture material (e.g., absorbable suture materials such as polyglycolic acid and polydioxanone, natural fibers such as silk, and artificial fibers such as polypropylene, polyester, polyester impregnated with polytetrafluoroethylene, nylon, polyetheretherketone, etc.), (2) a metal (absorbable or non-absorbable), (3) a metal alloy (e.g., stainless steel), (4) a shape memory material, such as a shape memory alloy (e.g., a nickel titanium alloy), (5) other biocompatible material, or (6) any combination thereof. In some variations, when pulled proximally while restraining the position of the proximal anchor, the guide element may be used to cinch or reduce the circumference of the atrio-ventricular valve annulus or the annular tissue. In certain variations, the guide element may be in the form of a wire. The guide element may include multiple layers, and/or may include one or more coatings. For example, the guide element may be in the form of a polymer-coated wire. In certain variations, the guide element may consist of a combination of one or more sutures and one or more wires. As an example, the guide element may be formed of a suture that is braided with a wire. In some variations, the guide element may be formed of one or more electrode materials. In certain variations, the guide element may be formed of one or more materials that provide for the telemetry of information (e.g., regarding the condition of the target site).

In some embodiments, the guide element may include one or more therapeutic agents (e.g., drugs, such as time-release drugs). As an example, the guide element may be partially or entirely coated with one or more therapeutic agents. In certain variations, the guide element may be used to deliver one or more growth factors and/or genetic regenerative factors. In some variations, the guide element may be coated with a material (e.g., a polymer) that encapsulates or controls the release rate one or more therapeutic agents, or in which one or more therapeutic agents are embedded. The therapeutic agents may be used, for example, to treat the target site to which the guide element is fixedly attached or otherwise secured. In certain variations, the guide element may include one or more lumens through which a therapeutic agent can be delivered.

After the first anchor has been deployed in the region of the heart valve annular tissue, the first delivery catheter is withdrawn proximally from the tunnel catheter. While maintaining the existing position of the outer catheter of the tunnel catheter about the subannular groove region, the inner catheter of the tunnel catheter is repositioned at a second opening of the outer catheter 134. A second delivery catheter is then advanced over the guide element through the lumen of the tunnel catheter 136. In some embodiments, subsequent delivery of anchors can be achieved by removing and reloading the first delivery catheter. In other embodiments, the delivery catheter is loaded with a plurality of anchors and does not need to be withdrawn from the tunnel catheter to deliver subsequent anchors.

During advancement of the second delivery catheter over the guide element, the guide element may enter the second delivery catheter through an opening at its distal end, and exit the second delivery catheter through an opening in its side wall that is proximal to its distal end. Alternatively, the guide element may enter the second delivery catheter through an opening at its distal end, and exit the second delivery catheter through an opening at its proximal end, or at any other location proximal to the distal end. After the second delivery catheter has been advanced over the guide element through the lumen of the tunnel catheter, a second anchor is deployed into a second region of the heart valve annular tissue using a second opening of the tunnel catheter 138.

The procedure described above represents one embodiment of the invention that may be used to treat the annular tissue of the mitral valve. In other embodiments of the invention, other tissues or structures of the heart and vasculature can also be treated, including but not limited to the subvalvular apparatus, septal structures and the myocardium. In still other embodiments, one or more cinchable implants may be deployed in non-cardiac tissues or structures, for example, to treat gastrointestinal disorders such as obesity, genitourinary conditions such as incontinence, or to perform cosmetic and reconstructive procedures.

Figure 3A:
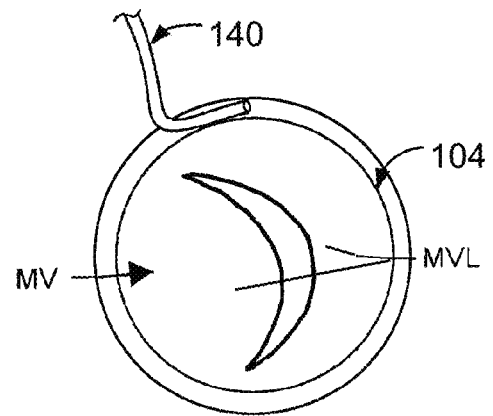
FIGS. 3A to 3I schematically depict a method for delivering multiple tissue anchors using a guide tunnel having multiple tissue openings.
Figure 3B:
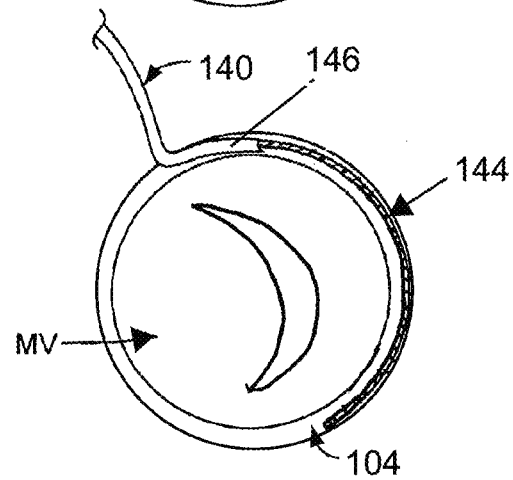

FIGS. 3A to 3I provide a more detailed depiction of the method shown in flowchart form in FIG. 2. In FIGS. 3A to 3I, the mitral valve MV of FIG. 1 is depicted schematically from an inferior perspective looking in a superior direction, but in other embodiments of the invention the tricuspid valve, pulmonary valve or aortic valve may be accessed. Referring to FIG. 3A, a guide catheter 140 is advanced to subannular groove region 104 using any of the access routes (or any other suitable access routes) described herein. In FIG. 3B, after guide catheter 140 has been positioned at the desired location in subannular groove region 104, a guidewire 144 is advanced through the lumen of guide catheter 140. Guidewire 144 may be advanced beyond the distal end 146 of guide catheter 140, so that guidewire 144 extends further along subannular groove region 104 than guide catheter 140, as shown in FIG. 3B.

Figure 3C:
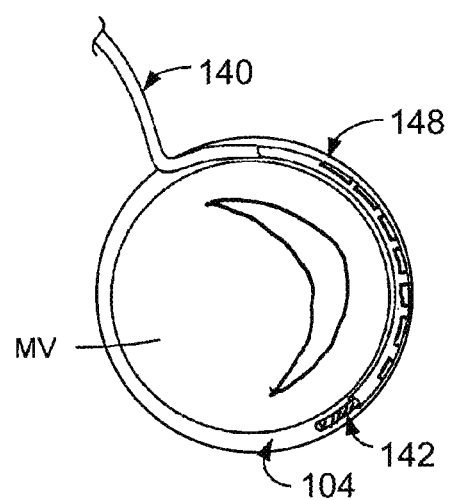

After guidewire 144 has been positioned in the subannular groove region 104, a guide tunnel or tunnel catheter 148 is advanced through guide catheter 140, over guidewire 144, as shown in FIG. 3C. Tunnel catheter 148 may be any suitable catheter, and in some instances, it is desirable that the tunnel catheter be pre-shaped or pre-formed at its distal end, such as the tunnel catheter illustrated in FIG. 3C. In some embodiments, tunnel catheter 148 may have a pre-shaped distal portion that is curved. In this way, the tunnel catheter may more easily conform to the geometry of the atrioventricular valve. It should also be understood that any of the catheters or guidewires described here may be pre-shaped or pre-formed to include any number of suitable curves, angles or configurations. Of course, the guidewires and/or catheters described here may also be steerable.

Figure 3D:
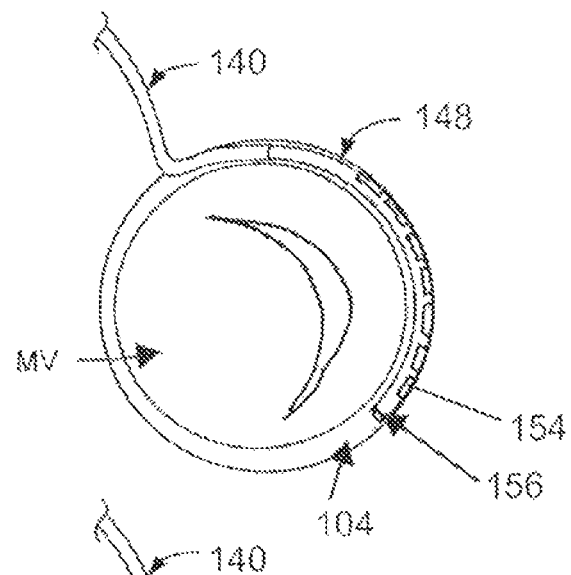

After tunnel catheter 148 has been positioned in the subannular groove region 104, guidewire 144 is withdrawn proximally as shown in FIG. 3D. A delivery catheter (not shown) may then be advanced through the lumen of tunnel catheter 148 and toward opening 154 at or adjacent to the distal tip 156 of tunnel catheter 148. In the embodiment depicted in FIG. 3E, the delivery catheter remains within tunnel catheter 148, and anchor 158 is deployed through opening 154 to attach to the body tissue. In other embodiments, however, the delivery catheter may be extended through opening 154 of tunnel catheter 148. Exemplary embodiments of a delivery catheter are depicted and described in greater detail below.

In some embodiments of the invention, opening 154 is the distalmost anchor delivery opening of tunnel catheter 148, but in some embodiments, one or more openings may have a separate lumen in tunnel catheter 148, so that any anchors deployed from such openings would not interfere or restrict the deployment of subsequent tissue anchors distal to those openings. Furthermore, although FIG. 3E depicts opening 154 as a side opening of tunnel catheter 148, in some embodiments, opening 154 may be located at the distal tip 156 and may be the same opening shown with a distally protruding guidewire 144 in FIG. 3C.

Figure 3E:
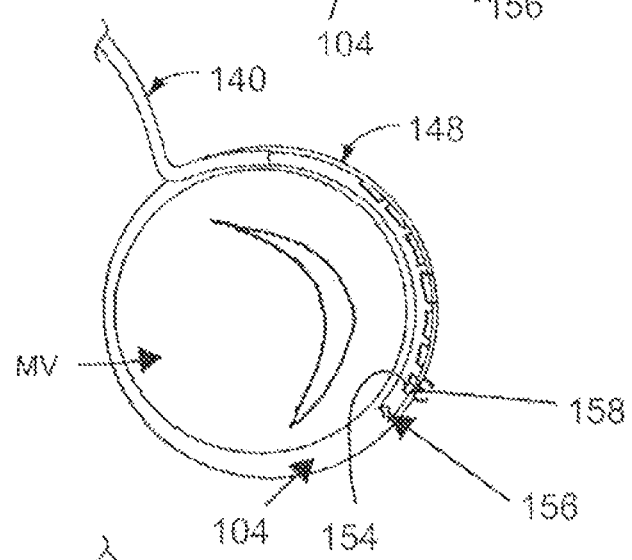

Anchor 158, shown in FIG. 3E, is preferably a self-expanding design as it exits the delivery catheter and tunnel catheter 148 to self-secure into the annular tissue accessible from the subannular groove region 104. It should be understood that one or more anchors of an implant may be deployed into the annulus directly, while other anchors may be secured to other tissue in the vicinity of the subannular groove region 104. For example, one or more anchors may be secured to the tissue below the annulus. After anchor 158 has been deployed, the delivery catheter may be proximally withdrawn. A tether 160, attached to anchor 158 and seen best in FIGS. 3G and 3H, may be used to facilitate the insertion of additional delivery catheters toward the implantation site.

Figure 3F:
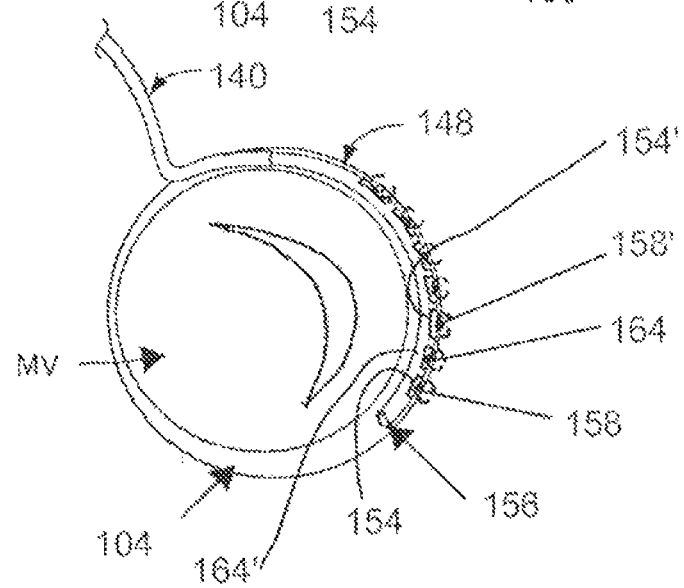

In this particular embodiment, as demonstrated in FIG. 3F, tunnel catheter 148 is maintained in the same position while additional anchors 164 and 158' are deployed from additional openings 164' and 154' along tunnel catheter 148. In some embodiments, one or more delivery catheters are serially inserted into tunnel catheter 148 using tether 160 to serially guide anchors 164 and 158' through openings 164' and 154'. In some embodiments, the delivery catheters may be loaded with one or more anchors at the point-of-use, while in other embodiments the delivery catheters may be pre-loaded at the point-of-manufacture. In other embodiments, the delivery catheters may be reloaded at the point-of-use, while in other embodiments, the delivery catheters are single-use devices that are discarded after anchor deployment. In other embodiments, the delivery catheters are configured to hold two or more anchors 158, 158' and 164 and can deliver multiple anchors without requiring withdrawal of the delivery catheter between anchor deployments. Still other multi-anchor delivery catheters are configured to deliver multiple anchors simultaneously through multiple openings of tunnel catheter 148. Anchors 158, 158' and 164 may be deployed from the delivery catheter and tunnel catheter 148 in any suitable fashion, including but not limited to a push-pull wire, using a plunger, or other suitable actuation technique. Similarly, anchors 158, 158' and 164 may be coupled to tether 160 by any suitable attachment method. For example, one or more knots, welded regions, and/or adhesives may be used. Alternate embodiments for anchor deployment and anchor attachments are described in U.S. patent application Ser. No. 11/583,627, which is hereby incorporated by reference in its entirety.

"Anchors," for the purposes of this application, are defined to mean any fasteners. Thus, the anchors may comprise C-shaped or semicircular hooks, curved hooks of other shapes, straight hooks, barbed hooks, clips of any kind, T-tags, or any other suitable fastener(s). In one embodiment, anchors may comprise two tips that curve in opposite directions upon deployment, forming two intersecting semicircles, circles, ovals, helices or the like. In some embodiments, the tips may be sharpened or beveled. In some embodiments, the anchors are self-deforming. By "self-deforming" it is meant that the anchors are biased to change from a first undeployed shape to a second deployed shape upon release of the anchors 210 from a restraint. Such self-deforming anchors may change shape as they are released from a housing or deployed from a lumen or opening to enter annular tissue, and secure themselves to the tissue. Self-deforming anchors may be made of any suitable material such as spring stainless steel, or super-elastic or shape-memory material like nickel-titanium alloy (e.g., Nitinol).

In other embodiments, the anchors may be made of a elastic material and may be loaded into a delivery catheter in such a way that they change shape upon release. For example, anchors that are not self-deforming may be secured to tissue via crimping, firing or other application of mechanical force to facilitate tissue penetration and/or securement. Even self-securing anchors may be crimped in some embodiments of the invention, to provide enhanced attachment to tissue. In some embodiments, anchors may comprise one or more bioactive agents, including biodegradable metals and, polymers. In another embodiment, the anchors may comprise electrode components. Such electrodes, for example, may sense various parameters including but not limited to impedance, temperature and electrical signals. In other embodiments, such electrodes may be used to supply energy to tissue at ablation or sub-ablation amounts.

Figure 4A:
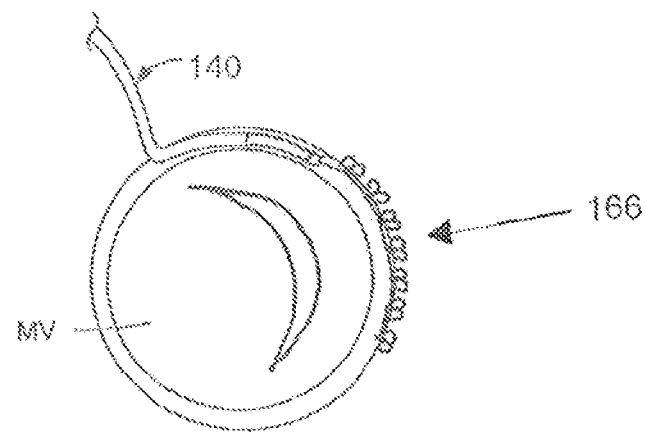
FIGS. 4A and 4B illustrate the use of various tissue anchors with a guide tunnel having multiple tissue openings.
Figure 4B:
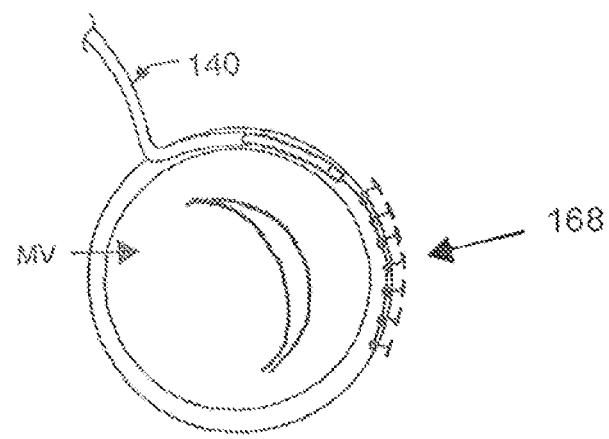
Figure 4C:
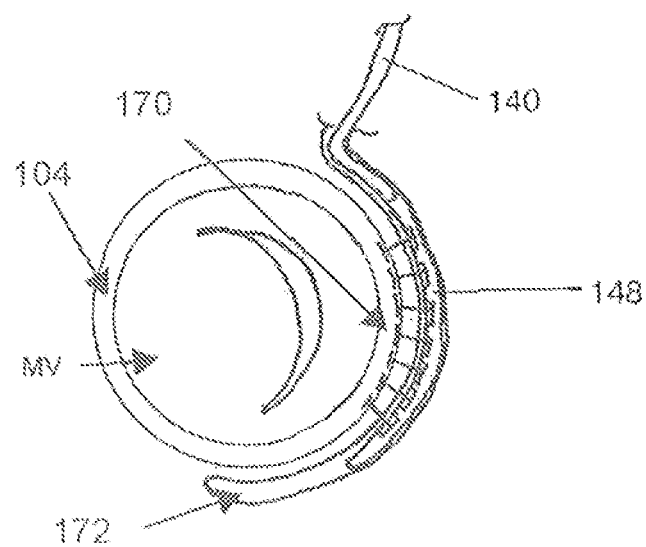
FIG. 4C shows the use of the guide tunnel in the coronary sinus.

FIG. 4A, for example, depicts an implant comprising multiple self-expanding, non-plicating anchors 166 deployed in the subannular groove region 104. FIG. 4B depicts an implant comprising multiple T-tag anchors 168 deployed in the subannular groove region 104, and FIG. 4C depicts transmural anchors 170 inserted from the coronary sinus 172 and into the subannular groove region 104. Other anchors may comprise fibrous or porous materials in the shape of bars, rods or pledgets. In some instances, the fibrous or porous materials may expand in volume. Additionally, while the delivery and deployment of multiple anchors of the same shape over a single guide element have been described, in some variations, a single guide element can be used to deliver and deploy multiple anchors having different shapes or non-uniform implantation sites. Similarly, in certain embodiments, a single guide element can be used in the delivery and deployment of multiple anchors having different sizes. Illustrative examples of suitable anchors are described in more detail, for example, in U.S. patent application Ser. No. 11/202,474, which is hereby incorporated by reference in its entirety.

In the embodiments depicted in FIGS. 3A to 3I, before a second delivery catheter is advanced through tunnel catheter 148, tether 160 is threaded into the delivery catheter, and is slidably engaged with a second anchor 164. In some embodiments, second anchor 164 is preloaded into the second delivery catheter before threading to tether 160, while in other embodiments, the second anchor is pre-threaded before being loaded into the second delivery catheter. Any of a number of different methods can be used to thread a guide element, such as tether 160, into a delivery catheter, and to engage the guide element with an anchor. Other methods are disclosed in U.S. patent application Ser. No. 11/202,474, which was previously incorporated by reference, and threading devices are described, for example, in U.S. patent application Ser. No. 11/232,190, which is hereby incorporated by reference in its entirety.

Figure 3G:
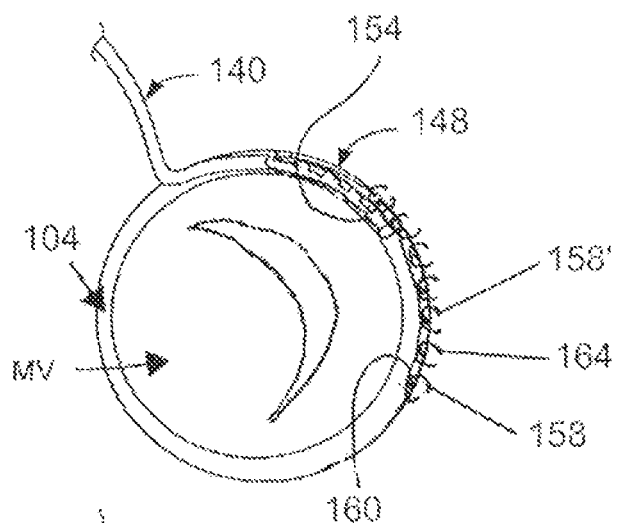
Figure 3H:
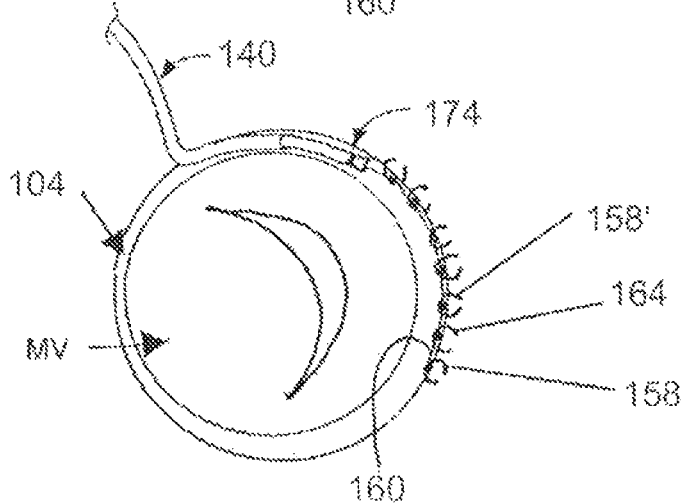
Figure 3I:
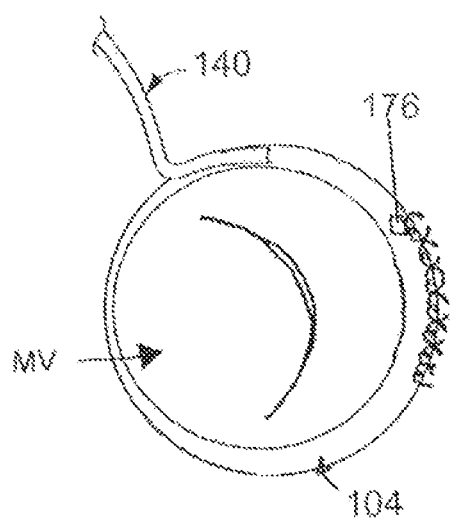

With reference to FIG. 3G, after all of anchors 158, 158' and 164 have been deployed into body tissue, tunnel catheter 148 is withdrawn from guide catheter 140. The separation of the tunnel catheter 148 from the anchors 158, 158' and 164 may occur by any of a variety of mechanisms, examples of which are described in greater detail below. In FIG. 3H, a termination catheter 174 is inserted through guide catheter 140 over tether 160. Termination catheter 174 is used to facilitate tensioning of tether 160, thereby cinching anchors 158, 158' and 164 together to remodel the annular tissue and to secure the cinched anchors 158, 158' and 164 with a termination member 176 that resists tether loosening or slippage, as illustrated in FIG. 3I. In other embodiments, termination catheter 174 can secure tether 160 to an anchor or to body tissue without the use of termination member 176. Devices and methods for performing termination of cinchable implants are described in U.S. patent Ser. No. 11/232, 190, which was previously incorporated by reference.

The catheters described herein, including tunnel catheter 148, may be formed of any of a number of different materials. Examples of suitable materials include polymers, such as polyether-block co-polyamide polymers, copolyester elastomers, thermoset polymers, polyolefins (e.g., polypropylene or polyethylene, including high-density polyethylene and low-density polyethylene), polytetrafluoroethylene, ethylene vinyl acetate, polyamides, polyimides, polyurethanes, polyvinyl chloride (PVC, fluoropolymers (e.g., fluorinated ethylene propylene, perfluoroalkoxy (PFA) polymer, polyvinylidenefluoride, etc.), polyetheretherketones (PEEKs), and silicones. Examples of polyamides include Nylon 6 (e.g., Zytel® HTN high performance polyamides from DuPont™), Nylon 11 (e.g., Rilsan® B polyamides from Arkema Inc.), and Nylon 12 (e.g., Grilamid® polyamides from EMS-Grivory, Rilsan® A polyamides from Arkema Inc., and Vestamid® polyamides from Degussa Corp.). In some variations, tunnel catheter 148 may be formed of multiple polymers. For example, a catheter may be formed of a blend of different polymers, such as a blend of high-density polyethylene and low-density polyethylene. While the wall of a catheter may be formed of a single layer, some variations of catheters may include walls having multiple layers (e.g., two layers, three layers). Furthermore, some variations of catheters may include at least two sections that are formed of different materials and/or that include different numbers of layers. Additionally, certain variations of catheters may include multiple (e.g., two, three) lumens. The lumens or walls may, for example, be lined and/or reinforced (e.g., with braiding or winding). The reinforcing structures, if any, may be metallic or comprise a non-metal or polymer having a higher durometer.

Figure 5A:
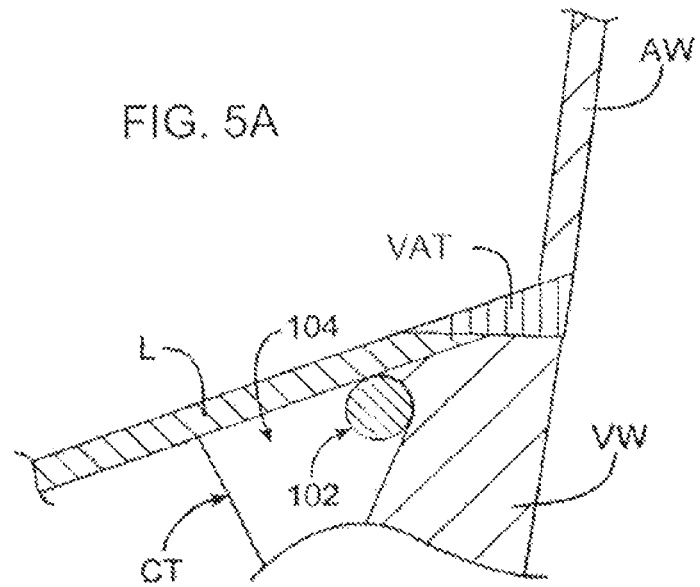

As illustrated in FIG. 5A, in one embodiment of the invention, distal portion 102 of delivery device 100 is positioned in a desired location under a valve leaflet L and adjacent a ventricular wall VW. The valve annulus VA generally comprises an area of heart wall tissue at the junction of the ventricular wall VW and the atrial wall AW that is relatively fibrous and, thus, significantly stronger than leaflet tissue and other heart wall tissue. It is noted, however, that considerable structural variations of the annulus exist within patient populations and that attempted delivery of an implant to the valve annulus VA may instead contact or attach to the tissue adjacent to the valve annulus. The term "annular tissue" as used herein shall include the valve annulus and the tissue adjacent or surrounding the valve annulus.

Distal portion 102 of guide catheter 100 may be advanced into position generally under the valve annulus VA by any suitable technique, some of which are described below. Distal portion 102 of guide catheter 100 may be used to deliver anchors to the valve annular tissue, to stabilize and/or expose the annulus, or both. In one embodiment of the invention, using guide catheter 100 having a flexible elongate body as shown in FIG. 1, flexible distal portion 102 may be positioned in the left ventricle LV at the level of the mitral valve leaflets MVL using any of a variety of access routes described herein. Distal portion 102 may be advanced under the posterior valve leaflet into a space such as the subannular groove region 104 or in the subvalvular space 106. Referring back to FIG. 5A, It has been found that when guide catheter 100 is passed, for example, under the mitral valve via an intravascular approach, guide catheter 100 may be inserted into the subannular groove region 104 or the subvalvular space 106 and advanced either partially or completely around the circumference of the valve. Once in subannular groove region 104 or the subvalvular space 106, distal portion 102 of guide catheter 100 may be positioned proximate to the intersection of the valve leaflet(s) and the ventricular wall VW, which is near the valve annulus VA. These are but examples of possible access routes of an anchor delivery device to a valve annulus, and any other access routes may be used. In other embodiments, guide catheters such as those described in U.S. Pat. No. 6,203,531, may be used. U.S. Pat. No. 6,203,531 is herein incorporated by reference in its entirety.

In some embodiments, it may be advantageous to provide guide catheter 100 with a curvable portion with a radius in an expanded/curved state that is greater than a radius of the valve annulus, the subannular groove region or ventricular chamber. The relative size of this portion of guide catheter 100, when positioned within the smaller sized ventricle, may exert a radially outward force that can improve the surface contact between guide catheter 100 and the left ventricle LV. For example, in one embodiment, guide catheter 100 in the expanded state has a radius about 25% to about 50% larger that the valve annulus.

Figure 5B:
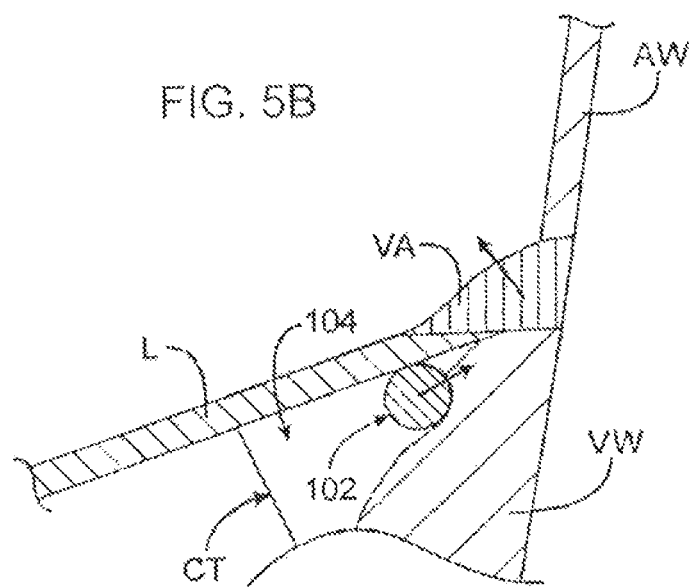

In addition to delivering anchors to the annular tissue, the guide catheter 100 (and specifically distal portion 102) may be used to stabilize and/or expose the valve annulus or annular tissue. Such stabilization and exposure are described fully in U.S. patent application Ser. No. 10/656,797, which is incorporated by reference in its entirety. For example, once the distal portion 102 is positioned generally under the annular tissue, force may be applied to the distal portion 102 to stabilize the valve annulus VA or annular tissue, as shown in FIG. 5B. Such force may be directed in any suitable direction to expose, position and/or stabilize the annulus or annular tissue. In another example, an upward and lateral force is shown in FIG. 5B by the solid-headed arrow drawn from the center of the distal portion 102. In other examples, only upward, only lateral, or any other suitable force(s) may be applied. With application of force to the distal portion 102, the annular tissue may rise or project outwardly, thus exposing the annulus for easier viewing or access. The applied force may also stabilize the valve annulus VA or valve annular tissue, also facilitating surgical procedures and visualization.

In some embodiments, additional force may be exerted by the delivery device after the first anchor is engaged to body tissue. The first anchor may provide additional leverage and stability for manipulating the delivery device(s). Referring to FIGS. 5C and 5D, a delivery device 108 is schematically shown delivering an anchor 110 to a valve annulus VA or annular tissue. Embodiments of anchor delivery device 108 are described in greater detail below. Anchor 110 is shown first housed within delivery device 108 in FIG. 5C and then delivered to the annulus VA or annular tissue, as depicted in FIG. 5D. Of course, although the delivery and position of the anchor 110 is described with respect to the valve annulus VA, one or more anchors 110 may miss the valve annulus VA and attach to other structures or tissues accessible from the subannular groove region 104 (or subvalvular space 106).

As is shown, in some embodiments, anchors 110 may have a relatively straight configuration when housed in delivery device 108, with two penetrating tips and a loop in between the tips. Upon deployment from delivery device 108, the tips of anchor 110 may curve in opposite directions to form two semi-circles, circles, ovals, overlapping helices or the like. This is but one example of a type of self-securing anchor which may be delivered to an annular tissue. Additional anchor embodiments are described below, and may also be found in U.S. patent application Ser. No. 11/202,474, which was previously incorporated by reference. Multiple coupled anchors 110 may be delivered, and the anchors 110 are drawn together to tighten the valve annulus.

Although delivery device 108 is shown having a circular cross-sectional shape in FIGS. 5C and 5D, it may alternatively have any other suitable shape. In one embodiment, for example, it may be advantageous to provide a delivery device having an ovoid or elliptical cross-sectional shape. Such a shape may help ensure that the device is aligned, when positioned between a corner formed by a ventricular wall and a valve leaflet, such that one or more openings in the delivery device is oriented to deliver the anchors in their desired orientation into valve annulus tissue. To further enhance contacting of the annular tissue and/or orientation of the delivery device, some embodiments may further include an expandable member, coupled with the delivery device, which expands to urge or press or wedge the delivery device into the corner formed by the ventricle wall and the leaflet to contact the valve annulus. Such enhancements are described further below.

Figure 6A:
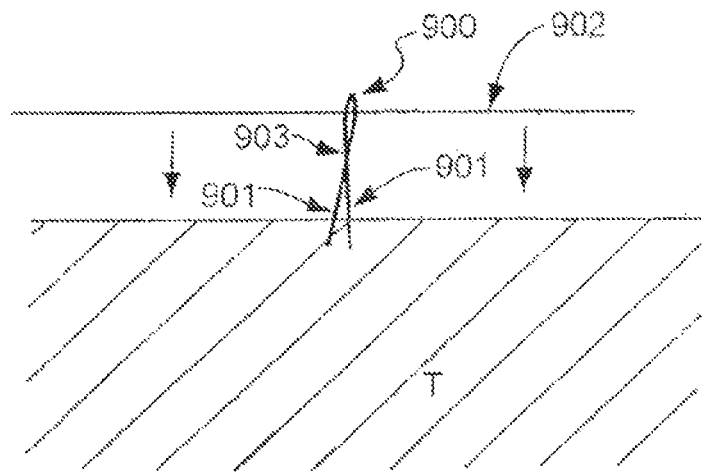
FIGS. 6A to 6C are schematic cross-sectional views of one embodiment of the invention comprising a self-forming anchor attaching to tissue.
Figure 6B:
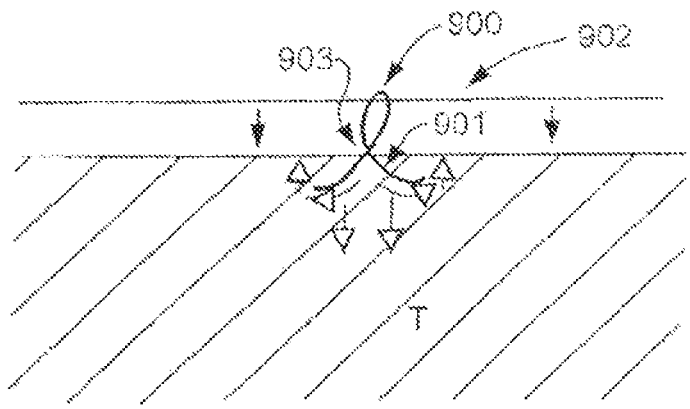
Figure 6C:
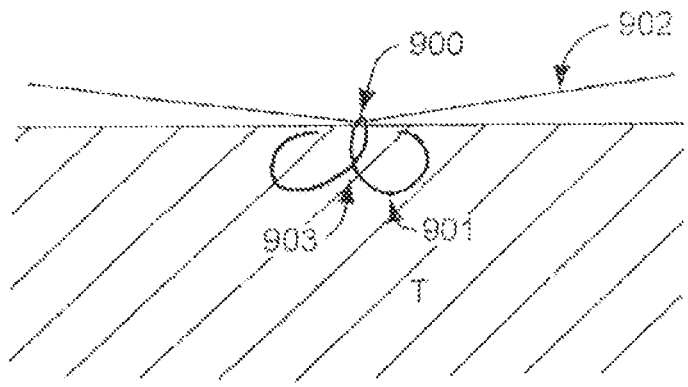
Figure 7D:
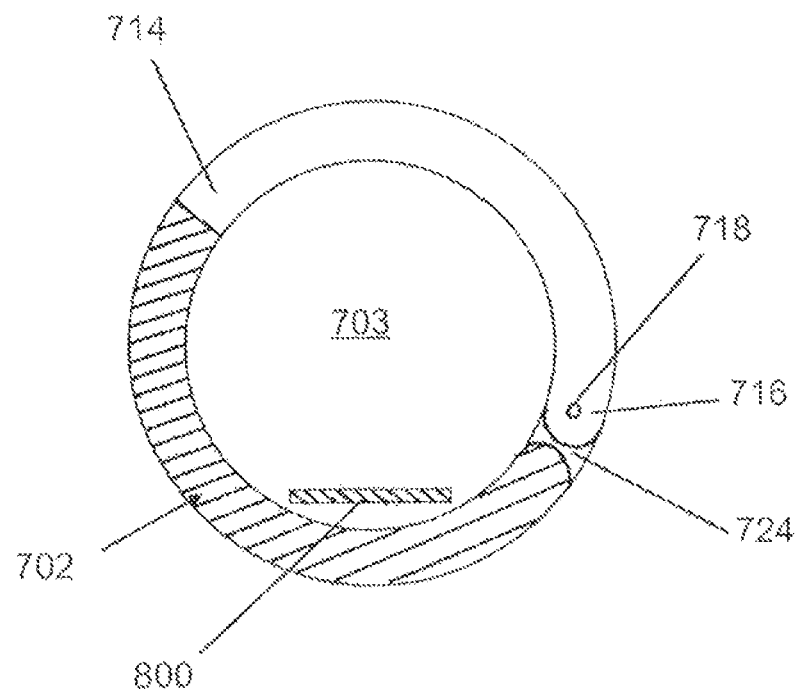
FIGS. 7D and 7E are schematic cross-sectional views of the multi-opening guide tunnel at various locations.
Figure 7E:
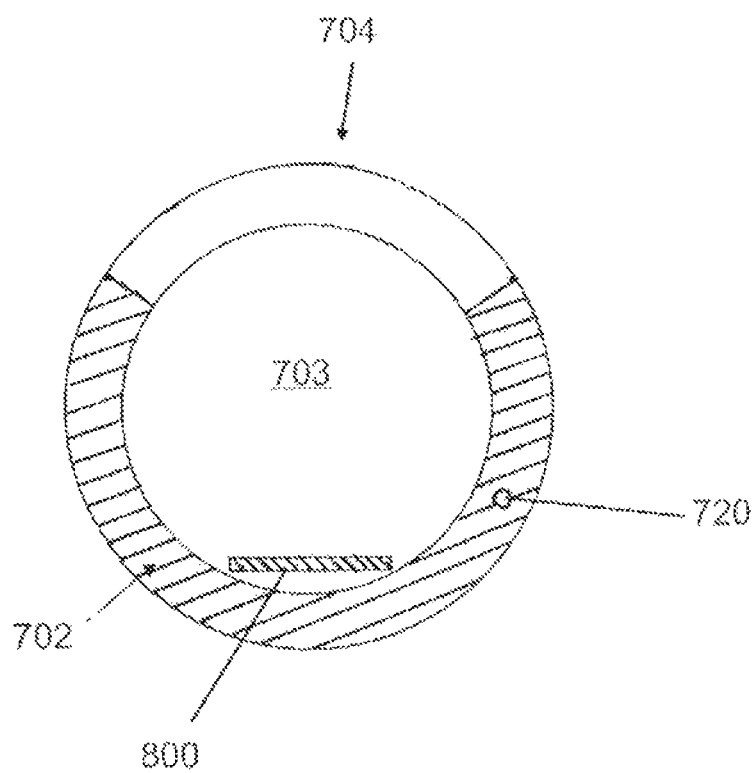

In several embodiments of the invention, one or more self-forming anchors 900 are stored in the delivery device in a straightened configuration, coupled with a tether 902, as shown in FIG. 6A. Anchors 900 are held or restrained in that straightened state, while their deployed configuration is non-linear or curved. Arms 901 meet at a junction section 903, which is slidably coupled to the tether 902. In some embodiments, junction section 903 comprises an open or closed loop configuration and may change in size or configuration when arms 901 are deployed. In this particular embodiment, as arms 901 of anchor 900 are released from the delivery system, arms 901 are permitted to resume their deployed configuration, penetrating the tissue T along a penetration pathway. As the distal portions of arms 901 regain their deployed configurations, arms 901 will separate and reorient toward the tissue surface (as depicted as open-headed arrows). In some embodiments, the penetration pathways are curved so that as anchor 900 further penetrates into tissue T, junctional section 903 of anchor 900 will continue along a similar pathway as the arms 901. This may reduce the degree of tissue compression or stretching as anchor 900 is deployed, which in turn may also reduce any resulting arrythmogenic risk, if any, from anchor deployment. The horizontal and vertical forces generated (depicted as open arrows) by arms 901 may also result in a counterforce which causes junction section 903 to be brought toward the tissue surface (down open arrows) and may even pull portions of junction section 903 into tissue T, as shown in FIG. 6B. Once the anchor is fully deployed, as in FIG. 6C, anchor 900 may be substantially embedded in the tissue T.

Portions of tether 902 coupled to junction section 903 are also brought closer to the surface of tissue T. Bringing tether 902 closer to tissue T may be beneficial because a greater proportion of the cross-sectional blood flow path, as bordered by tether 902, is preserved, which may reduce the risk that any subsequent catheters or implanted components inserted into the heart chamber or valve will snag or damage tether 902. Also, it may reduce the degree of hemolysis compared to a tether that crosses the mitral flow pathway farther from the tissue surface. Various anchor designs and deployment methods are disclosed, for example, in U.S. patent application Ser. Nos. 10/741,130, 10/792,681, 10/900,980, 11/255,400, and 10/901,555, which are herein incorporated by reference in their entirety, as well as U.S. patent application Ser. No. 11/202,474, previously incorporated by reference.

Referring now to FIGS. 7A through 7E, in one embodiment of the invention, the guide tunnel 700 comprises a tubular body 702 with a central passageway 703 and multiple openings 704. Central passageway 703, depicted in FIGS. 7D and 7E, permits the insertion of a delivery catheter and the alignment of one or more retained anchors with one or more of the openings 704 of guide tunnel 700. Typically, openings 704 are grouped in a distal portion 706 of guide tunnel 700, but in other embodiments, openings 704 may be located more proximally. The lengths and configurations of the tubular body 702 and distal portion 706 may vary depending upon a variety of factors, including but not limited to the desired target location, such as the subannular groove region, and the access route, whether it is retrograde, antegrade, or requires a transseptal puncture. In one example, distal portion 706 of guide tunnel 700 comprises a flexible curved configuration. In some embodiments, openings 704 are preferably aligned along the greater curvature 708 of distal portion 706. In other embodiments, openings 704 may be aligned along the superior junction of the curved distal portion. Similarly, guide tunnel 700 may be configured for a cinchable implant inserted via the coronary sinus by aligning openings 704 along the lesser curvature 710 of distal portion 706. Distal portion 706 may optionally comprise an atraumatic tip, such as an inflatable balloon or a tapered tip 709 comprising a material with a low durometer. Guide tunnel 700 may be used in conjunction with a guide catheter to facilitate positioning of a delivery catheter at the desired anchoring sites.

Figure 12A:
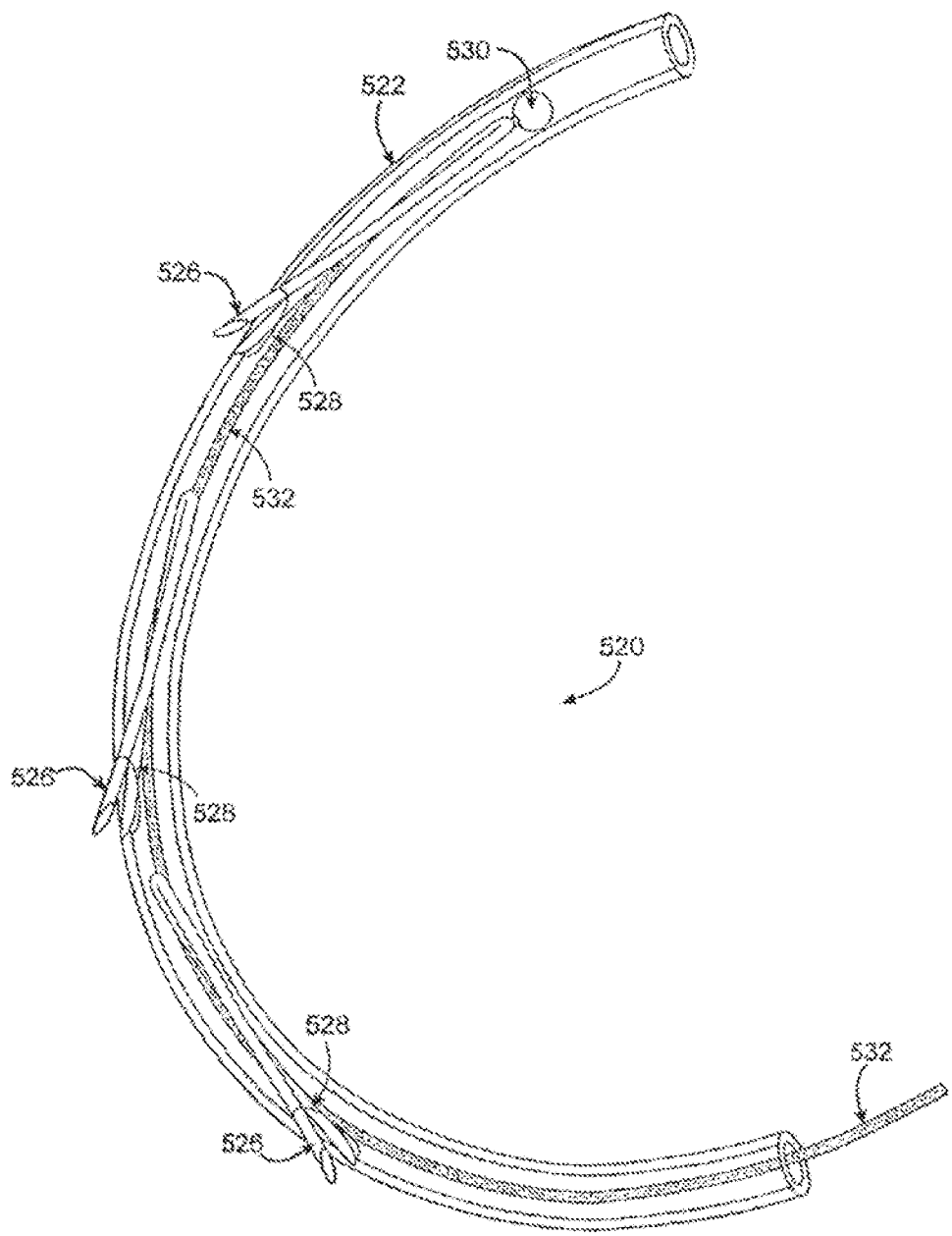
FIGS. 12A and 12B are perspective views of a distal portion of another embodiment of an anchor delivery catheter.
Figure 12B:
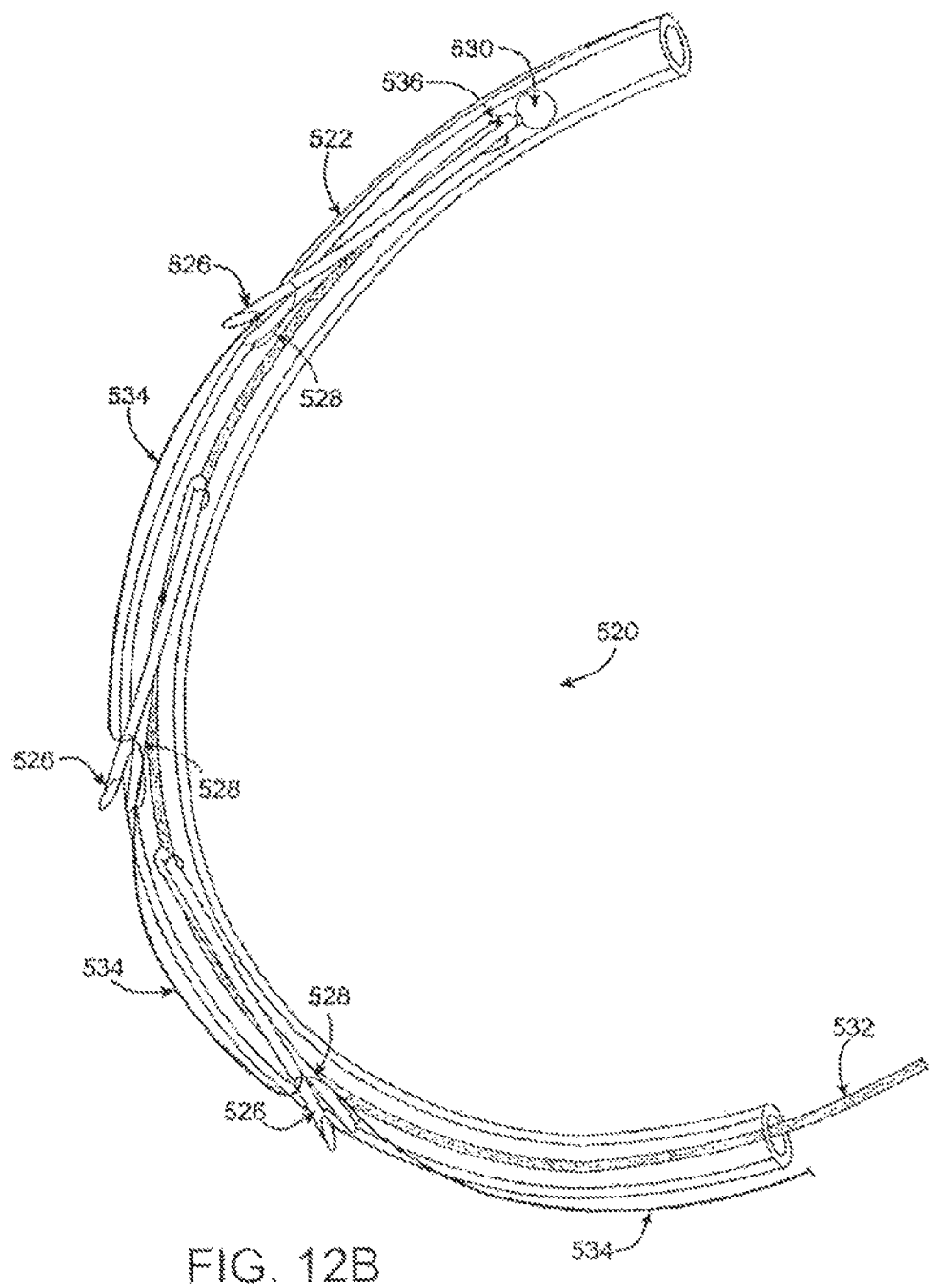

In some embodiments, the openings 704 are arranged in a linear configuration along a longitudinal length of guide tunnel 700. Although openings 704 are depicted in FIG. 7A through 7E as having uniform dimensions, shapes, uniform spacing and angular and linear alignment, these and other features of guide tunnel 700 may be varied as desired. For example, if the cinchable implant comprises anchors of different sizes and anchor spacings, the anchor opening cross-sectional shapes and areas and relativespacing may be designed accordingly. For example, opening 704 of guide tunnel 700 has a generally semi-cylindrical shape (or rect-angular shape when opening 704 is viewed orthogonally), while the aperture 528 of delivery device 520 in FIGS. 12A and 12B are generally oval in shape. In other examples, the openings of the guide tunnel may be squared, circular, semi-circular, triangular, octagonal, rhomboidal, trapezoidal, crescent-shaped, or any other shape. In still other examples, the openings may comprise slits which may deform to allow passage of an anchor or other component. The slits may have any of a variety of configurations, including linear, arcuate, cross or star-shaped configurations, for example.

Figure 24:
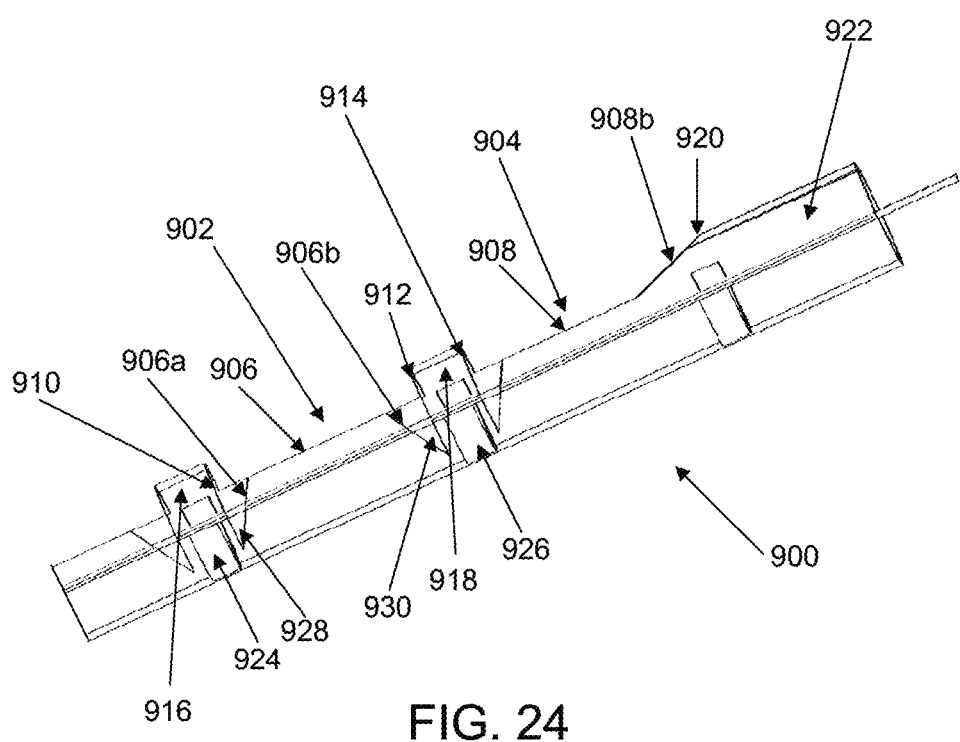
FIG. 24 is a schematic side view of another embodiment of a guide tunnel with openings comprising non-orthogonal edges.

FIG. 24 depicts an example of a guide tunnel 900 comprising multiple apertures 902, 904 with a non-rectangular shapes. The longitudinally origented edges 906 and 908 of each aperture 902 and 904 are configured so that they form a non-perpendicular angle with respect to the transverse edges 910, 912 and 914 of the retention elements 916 and 918, and the transverse edge 920 of the distal section 922 of the guide tunnel 900. As depicted, the longitudinal edge 906 of aperture 902 comprises angled sections 906a and 906b adjacent to the retention elements 916 and 918 which are angled toward the base 924 and 926 of the retention elements 916 and 918, forming acute angles 928 and 930. The angle between the angled sections of the longitudinal edges and the retention elements may be uniform or non-uniform with respect to each other and the edges may comprise straight, curved or other non-linear sections. The angles 928 and 930 may be in the range of about 0 degrees to about 180 degrees, in some configurations about 5 degrees to about 85 degrees, in other configurations about 10 degrees to about 45 degrees, and still other configurations about 20 degrees to about 30 degrees, while some alternate configurations is in the range of about 90 degrees to about 135 degrees, or about 100 degrees to about 120 degrees. The longitudinal edge 908 of aperture 904, for example, comprises a distal segment 908b is at a 110 degree angle with respect to the transverse edge 920 of the distal section 922 of the guide tunnel. In some examples, an obtuse angle between a longitudinal edge and a transverse edge of the guide tunnel may reduce the risk of an edge catching or interfering with adjacent anatomical structures and/or other devices or instruments inserted into the guide tunnel. However, obtuse angles are not limited to the distalmost apertures, or to the distal section of an aperture. The longitudinal dimensions of the non-orthogonal sections 906a, 906b and 908b may each in the range of about 5% to about 50% of the total longitudinal dimension of the generally longitudinal edges, sometimes about 5% to about 25%, and other times about 10% to about 20%.

Guide tunnel 700 may be used in beating heart procedures where it is difficult to control the position of the distal end of a delivery catheter with respect to the target tissue. By providing multiple openings 704, once guide tunnel 700 has been positioned at its desired location, it need not be moved to deploy a plurality of anchors. Instead, the delivery catheter can be manipulated within the non-moving guide tunnel 700 to deploy the anchors through the provided openings 704. Thus, guide tunnel 700 may reduce the risk that during a lengthy procedure with multiple anchoring sites, repositioning of the delivery catheter to a new target location may dislodge the delivery catheter from hard-to-reach target sites that are easily lost. In addition to transluminal procedures, guide tunnel 700 may also be used with open or limited access surgeries. In further embodiments of the invention, guide tunnel 700 may be configured with a shorter longitudinal length and/or a more rigid body for some surgical applications.

During the deployment of a cinchable implant, when the anchors have been secured to their target sites, the coupling members or one or more segments of the tether may still be looped within the delivery catheter or guide tunnel 700. This may be beneficial when implanting anchors in unstable body regions such as a beating heart because with each deployment of an anchor, the retention of a tether segment in guide tunnel 700 further secures guide tunnel 700 to the sites where the anchors have been secured. Once all of the anchors have been deployed, however, the retained tether segments will need to be separated from guide tunnel 700 so that guide tunnel 700 may be withdrawn.

In one embodiment of the invention, the retaining structures between anchor openings 704 may be configured to releasably retain the tether or coupling elements between the anchors. In a further embodiment, depicted in greater detail in FIGS. 14A through 14H, the retaining structures comprise latch structures 712 located between two adjacent openings 704 of guide tunnel 700. Referring back to FIG. 7B, which depicts latches 712 of guide tunnel 700 pulled away from tubular body 702, in some embodiments, latch 712 may comprise a base 714 and a free end 716. In some embodiments, latch 712 comprises a material and/or configuration to permit some deformation or deflection of latch 712 and for a tether or coupling member retained between two adjacent openings 704 to pass out of guide tunnel 700. Thus, in some embodiments, latch 712 comprises a flexible material, but in other embodiments, one or more latches may comprise a rigid material with a hinge joint or other type of joint that permits latch movement. The edges or corners of the latch structures 712 and/or openings 704 may be angled, as depicted in FIG. 14, or may be rounded.

Referring to FIG. 14B, latch 712 may be configured to permit control of the retention and/or release of the tether between deployed anchors. In some embodiments, latch 712 comprises a lumen 718 that is alignable with complementary segments 720 of a lumen located in the wall of the tubular body 702. The complementary lumen segments 720 may be provided in a notched region 724 which is complementary to free end 716 of latch 712. When aligned, each adjacent lumen 718 and segment of the longitudinal lumen 720 permits the insertion of a locking element 722. Locking element 722 can releasably secure the latch 712 in the notched region 724 by maintaining the alignment between the lumen 718 of latch 712 and lumen segment 720 of tubular body 702, thereby restricting the passage of a coupling member. When anchors are deployed through openings 704 adjacent to latch 712, the tether will be retained by latch 712.

In some embodiments, locking element 722 may have an elongate configuration and comprise a wire thread, or ribbon formed from metal, polymer, or combination thereof. Referring back to the embodiment depicted in FIG. 7A, latch 712 comprise transverse through-lumens 718 that complement the lumen segments of the longitudinal lumen 720 of the tubular body 702, but the particular orientations of the lumens or locking elements may vary, depending on the desired orientation of openings 704. Lumen 718 of latch 712 need not be a through-lumen or a transversely oriented lumen with respect to base 714 and free end 716 of latch 712. In some embodiments, latches 712 may comprise radio-opaque material to facilitate the positioning of a delivery catheter with respect to guide tunnel 700. In other embodiments, radio-opaque material may be located in or on tubular body 702 in angular position generally opposite one or more latches 712 or elsewhere.

Figure 8A:
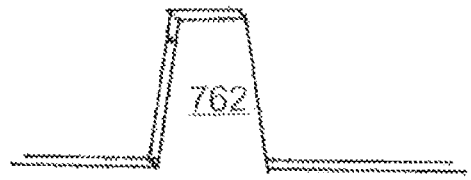
FIGS. 8A to 8D represent various embodiments of a latch.
Figure 8B:
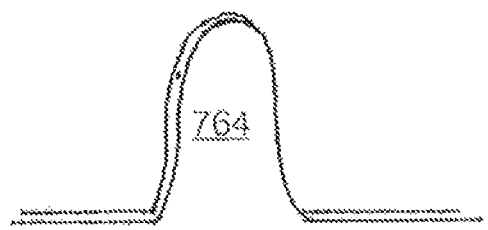
Figure 8C:
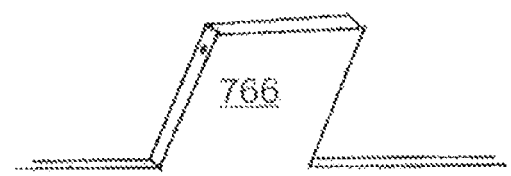
Figure 8D:
Figure 8E:
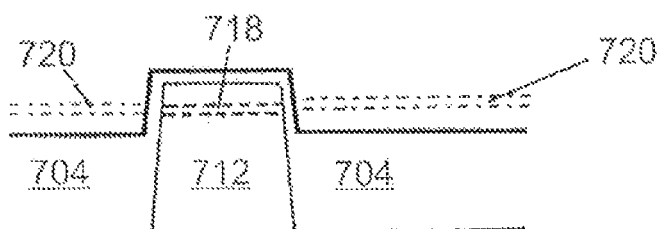
FIGS. 8E and 8F are schematic representations of various locking lumens for a latch.
Figure 8F:

In some embodiments, latch 712 may not maintain the alignment of lumen 718 with its complementary lumens 720 once locking element 722 is removed. In these embodiments, reinsertion or rethreading of locking element 722 back into lumen 718 may not work in situ. In other embodiments, however, guide tunnel 700 may be constructed such that latch 712 is biased to an alignment position and locking element 722 may be reengaged to one or more lumens 718, 720. To facilitate initial insertion or reinsertion of locking element 722 into lumens 718, 720, lumens 718, 720 may be provided with one or more tapered lumen openings 760 as depicted in FIG. 8F.

In some embodiments, a single locking element 722 is provided and is insertable through all lumens 718 of latch 712 and complementary lumens 720 of tubular body 702, and the aggregate lumen path from lumens 718 and complementary lumens 720 is substantially linear or curvilinear. With these particular embodiments, release of latches 712 start with the distalmost latch and finish with the most proximal latch. In other embodiments, the lumens and the locking element, such as the locking element 725 shown in FIG. 9B, may be configured to simultaneously release two or more latches 712. With locking element 725, branched segments 726 of locking element 725 permit parallel release of latches 712.

Figure 22A:
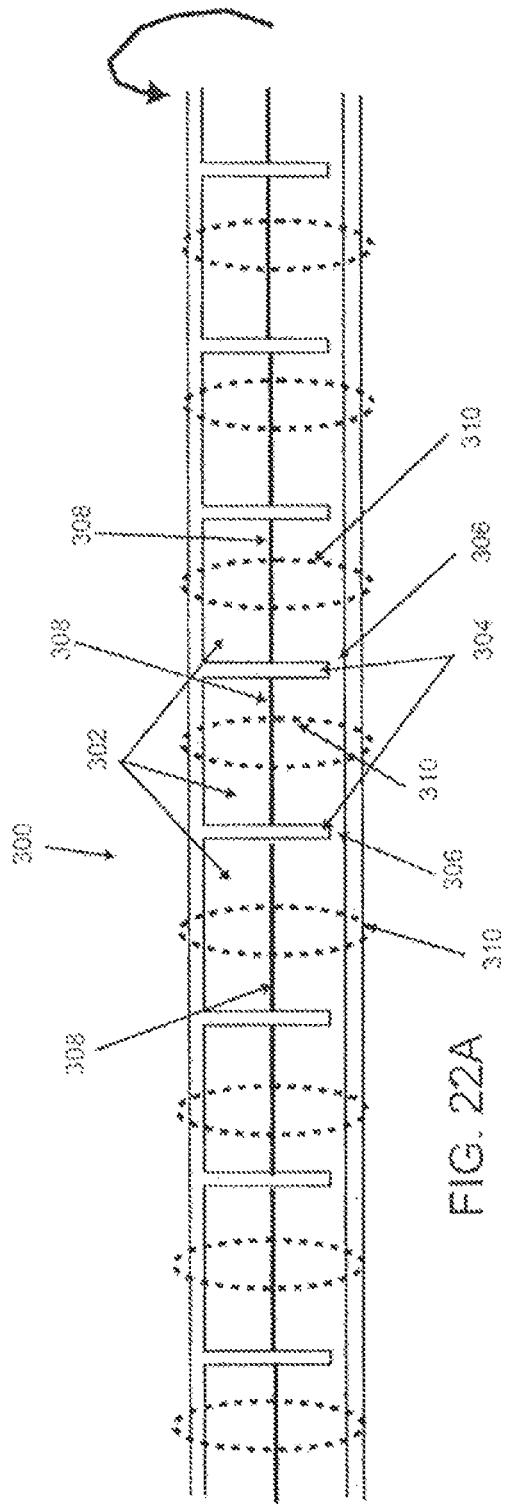
FIGS. 22A and 22B represent another embodiment of a guide tunnel.
Figure 22B:
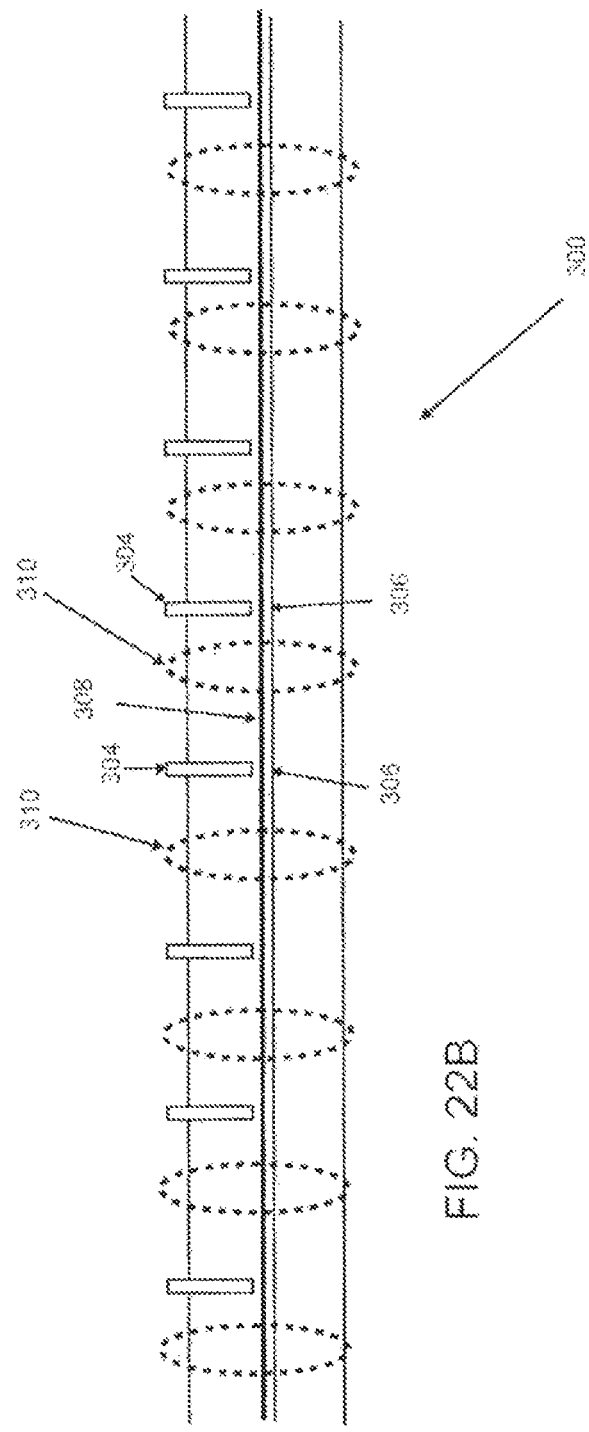

Although FIG. 14B depicts an interlocking fit between locking element 722, lumen 718 and lumen segment 720, other retaining mechanisms may also be used. In FIG. 22A, for example, a guide tunnel 300 with a plurality of delivery catheter apertures 302 is provided. Delivery catheter apertures 302 are separated by retaining members 304 with an open seam or gap 306. As shown schematically in FIG. 22B, after anchor deployment is completed, guide tunnel 300 may be rotated or otherwise moved away from the retained tethers 308 to permit release of tether 308 from guide tunnel 300 through gaps 306. Guide tunnel 300 can then be separated from the tethered anchors 310.

FIG. 23A depicts another embodiment of a guide tunnel 312, comprising an outer guide 314 with one or more openings 316, each configured to deliver a plurality of anchors at along a range a length, and an inner guide within outer guide 314 comprising a tubular body with two or more longitudinally spaced retaining members 316. Retaining members 316 may be configured for release with one or more locking elements, or may be configured for displacement from a retained tether similar to the configuration of retaining members illustrated in FIG. 22A.

FIGS. 7A to 7D illustrate an embodiment comprising latches 712 with a generally symmetrical protruding structure that lacks sharp corners. FIGS. 8A through 8D depict other embodiments of the invention with latches of different configurations. In FIG. 8A, for example, the latch 762 is generally symmetrical with a larger base and squared edges. In FIG. 8B, latch 864 is also generally symmetrical with a larger base but with rounded edges. In FIGS. 8C and 8D, though, latches 866 and 868, respectively are asymmetrical. Asymmetrical configurations may be useful for facilitating separation of an implant from the guide tunnel by angulating any force exerted on the latch edge toward the free end of the latch.

In other embodiments of the invention, locking element 722 may comprise an electrically conductive material that melts upon the application of sufficient electrical current to permit the release of latch 712. In still other embodiments, the releasable retaining mechanism may comprise magnetic controlled locks or electropolymers embedded in latch 712 that may be controlled with application of current to wires embedded in tubular body 702 between latches 712 and the proximal end of guide tunnel 700.

Referring back to FIG. 7A, proximally, guide tunnel 700 may comprise one or more access ports. One or more of the ports 728, for example, may also be configured with a hemostatic seal to reduce blood loss during the procedure, and or with a reversible locking mechanism 730 to maintain the relative position between an inserted component and guide tunnel 700. Port 728 may be used for insertion and removal of the delivery catheter, for example. In some embodiments, one or more ports 732, 734 may be provided to obtain blood samples, for injection of radiographic or therapeutic agents, or for the attachment of a pressure transducer. Another port 736 may be provided for manipulation of locking element 722 which controls the release of latch structures 712.

Figure 25A:
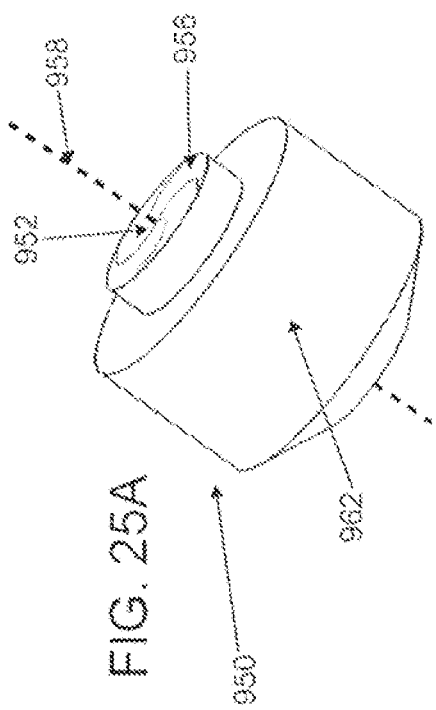
FIG. 25A is a perspective views of one embodiment of a hemostatic seal.
Figure 25B:
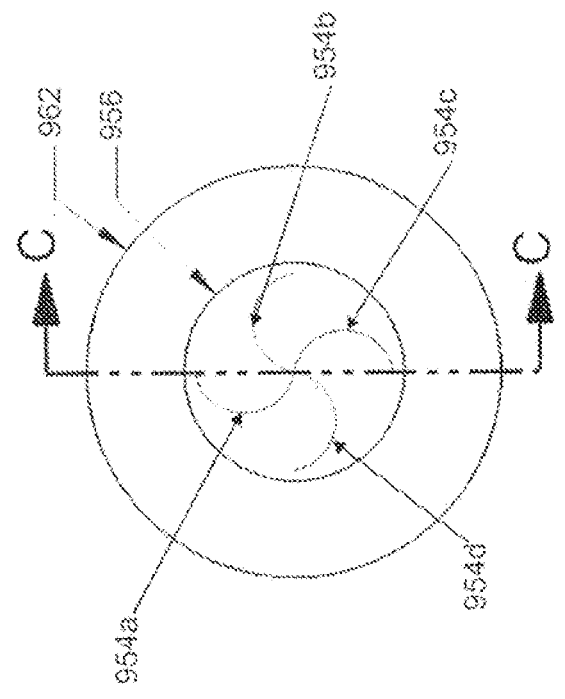
FIG. 25B is an posterior elevational view of the seal of FIG. 25A.
Figure 25C:
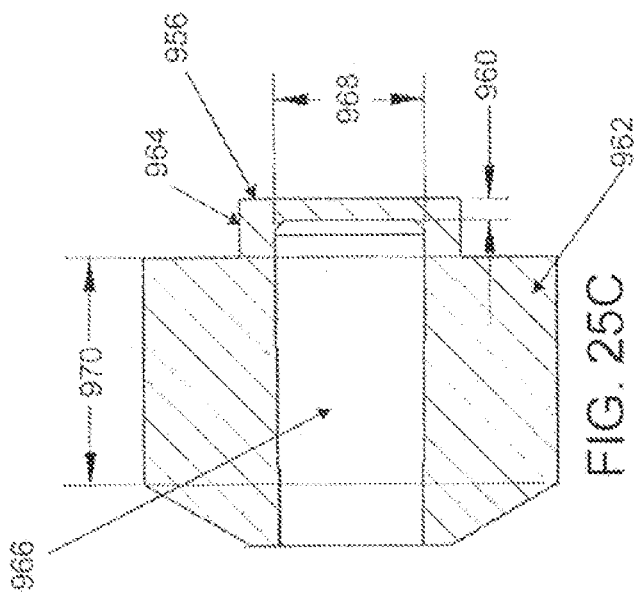
FIG. 25C is a cross-sectional view of the seal in FIG. 25B.
Figure 26:
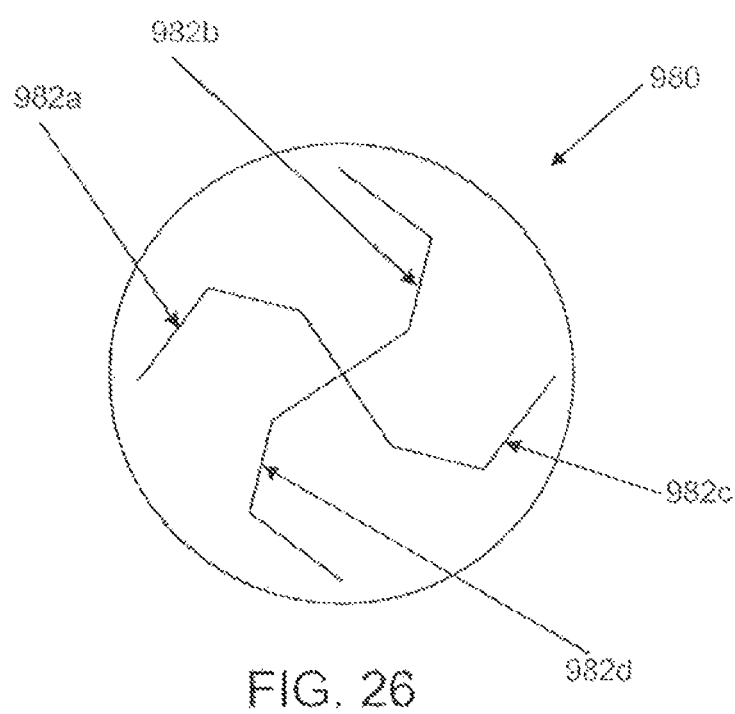
FIG. 26 is a posterior elevational view of an alternate seal configuration.

The hemostatic seal may comprise any of a variety of configurations known in the art. In some examples, the hemostatic seal may comprise one or more slits on a septum or sealing member which forms one or more seal flaps. Upon insertion of an instrument or device through the sealing member, the seal flaps deform or deflect to permit passage of the device while exerting force around a perimeter of the device to substantially resist passage of fluid or gas through the sealing member. Referring to FIGS. 25A to 25C, in some examples, the sealing member 950 has a seal opening 952 comprising at least one non-linear slit 954a-d with respect to the seal face 956 or a transverse plane of the seal axis 958. In the depicted example, the sealing opening 952 comprises four arcuate or spiral-shaped slits 954a-d arranged about the seal axis 958. Each of the slits 954a-d has the same relative shape and size as the other slits 954a-d and uniformly spaced around the axis 958, but in other examples, a different number of slits may be provided, one or more slits may have a different size or shape, the slits may be non-uniformly spaced or non-symmetrically arranged, and/or may intersect at location different from the center of the seal face 956. In FIG. 26, for example, the sealing member 980 comprises a plurality of multi-angled slits 982a-d.

Referring back to FIGS. 25A to 25C, the slits 954a-d may have a generally orthogonal orientation through the seal face 956, or may be angled or skewed. In some examples, the slits 954a-d may be generally angled with respect to the seal face 956 in the range of about 5 degrees to about 85 degrees, in some configurations about 10 degrees to about 60 degrees, and in other configurations about 20 degrees to about 45 degrees. The seal face 956 or seal member 950 may comprise any of a variety of elastic or flexible materials, including any of a variety of silicones such as NuSil Med-4035, Med-4820, and MED50-5338, may have a durometer in the range of about 20 to about 80, in some examples about 15 to about 60, and in other examples about 20 to about 40. The thickness 960 of the seal face 956 may be in the range of about 0.01" to about 0.1", in some examples about 0.02" to about 0.05", and in other examples about 0.025" to about 0.03". As illustrated in FIG. 25B, the seal face 956 may be raised or offset from the body 962 of the sealing member 950. The raised distance 964 of the raised seal face 956 may be in the range of about 0.01" to about 0.2", in some configurations about 0.02" to about 0.1" and in other configurations about 0.04" to about 0.06".

The body 962 comprises a lumen 966 in communication with the sealing opening 952. The lumen 966 may have a uniform or non-uniform diameter, cross-sectional area and/or cross-sectional shape. Lumens with non-uniform diameters may taper toward or away from the seal opening 952, and the taper may be linear or non-linear. In some examples, the lumen 966 may have an average diameter 968 in the range of about 0.05" to about 0.5" or more, in some configurations about 0.1" to about 0.3", and in other configurations about 0.15" to about 0.2". The lumen 966 may have a length 970 anywhere in the range of about 0.1" to about 1" or more, in some configuration about 0.2" to about 0.5", and in other configurations about 0.25" to about 0.4". The body 962 may have any of a variety of shapes, including cylindrical, frustoconical, box-like or other shapes, and may be coupled to the guide tunnel by a frame or housing.

In some embodiments, guide tunnel 700 may be used in conjunction with a delivery catheter comprising multiple anchors with preset spacing, similar to that depicted in FIGS. 12A and 12B. In further embodiments, the spacing of the delivery catheter may match the spacing of openings 704 of guide tunnel 700. This particular combination may permit simultaneous deployment of anchors or reduce the time spent to align the delivery catheter and guide tunnel 700. In a preferred embodiment, a delivery catheter with plural anchors and a guide tunnel with plural openings may be provided in a kit with one or more other components described herein.

In another embodiment, guide tunnel 700 further comprises an inner guide tunnel 750 that is reversibly insertable into passageway 703 of guide tunnel 700. In these and other embodiments comprising inner guide tunnel 750, port 728 that is configured to receive the delivery catheter will be located on the inner guide tunnel 750 while guide tunnel 700 will have a port 752 configured to receive the inner guide tunnel 750. Inner guide tunnel 750 further comprises an inner tubular body 754 with one or more openings 756 located at the distal end 758 of the inner tubular body 754. Opening 756 may be configured with flanking or other configuration of radio-opaque markers that can be used to align opening 756 of inner guide tunnel 750 with the corresponding radio-opaque markers of latches 712. Opening 756 may comprise the same material as inner tubular body 754. In other embodiments, opening 756 is reinforced with a frame 806. In some embodiments, frame 806 may comprise a polymer of higher durometer than material comprising inner tubular body 754. In other embodiments, frame 806 may comprise a metal such as stainless steel, cobalt chromium, platinum-iridium, or Nitinol. In further embodiments, frame 806 may be plated with an additional metal, including but not limited to gold. In some embodiments, frame 806 is plated with additional material to alter its radio-opacity. Inner guide tunnel 750 may also be configured with one or other proximal ports 734 previously mentioned.

In some embodiments of the invention, guide tunnel 700, inner guide tunnel 750 or the delivery catheter may include a position sensor system to detect the relative position of inner guide tunnel 750 and/or the delivery catheter. In one embodiment, the position sensor system comprises a series of electrical contact points along passageway 703 of guide tunnel 700 that can form an electrical circuit with one or more electrical contact points located on inner tubular body 754. Similarly, electrical contact points in the lumen of inner guide tunnel 750 can be used to detect the position of delivery catheters inserted therein. The position sensor system may be used as a substitute or in conjunction with radio-opaque markers to facilitate alignment of various components. Other types of position sensor system are also contemplated, including but not limited to optical and magnetic detection mechanisms.

In some embodiments of the invention, guide tunnel 700 with inner guide tunnel 750 may be used with delivery catheters comprising a single anchor, or delivery catheters with multiple anchors. In these embodiments, inner guide tunnel 750 may be used to simplify positioning of delivery catheters with respect to openings 704 on guide catheter 700. Inner guide tunnel 750 may also be provided with one or more visual markings, detents, servo motor controlled positioning or other mechanisms to facilitate anchor delivery through openings 704. In some embodiments, inner guide tunnel 750 may be configured, for example, to reorient end-firing anchor delivery catheters to deploy anchors through the side openings 705 of guide tunnel 700.

In some embodiments, guide tunnel 700 and inner guide tunnel 750 may be configured to restrict or limit any rotational movement between the two components. Such a feature may be useful when positioning in more difficult target locations in the body that require considerable length, angulation and torque to reach that may result in rotation and/or length misalignment. In one embodiment of the invention, depicted in FIGS. 14C to 14E, passageway 703 of distal section 706 is configured with a rail 800, groove or other alignment structure to resist rotational movement of inner guide tunnel 750. Rail 800 is attached at a distal end 804 and a proximal end (not shown) and permits inner guide tunnel 750 to longitudinally slide along between its two attachment points, where rail 800 passes through slots 802 or slits formed in the tubular body 754 of inner guide tunnel 750. In some embodiments, the rail has a width to thickness ratio of about 5:1 to about 20:1, preferably about 8:1 to about 16:1, and most preferably about 9:1 to about 14:1. In other embodiments, rail 800 is not attached proximally and permits inner guide tunnel 750 to be fully withdrawn from guide tunnel 700 and exchanged for a different inner guide tunnel 750. Rail 800 preferably comprises materials selected to reduce or minimize any friction or cohesion effects between the rail and the material comprising tubular body 754 of inner guide tunnel 750. In some embodiments, rail 800 may comprise a metal such as stainless steel or Nitinol. In other embodiments, rail 800 or other alignment configuration may comprise a lubricious coating such as PTFE to reduce movement resistance of inner guide tunnel 750. In still other embodiments of the invention, rail 800 may have a different cross sectional shape from flat band configuration depicted in FIG. 14C, including but not limited to square, rectangle, circle, oval or other geometric shape.

Figure 10A:
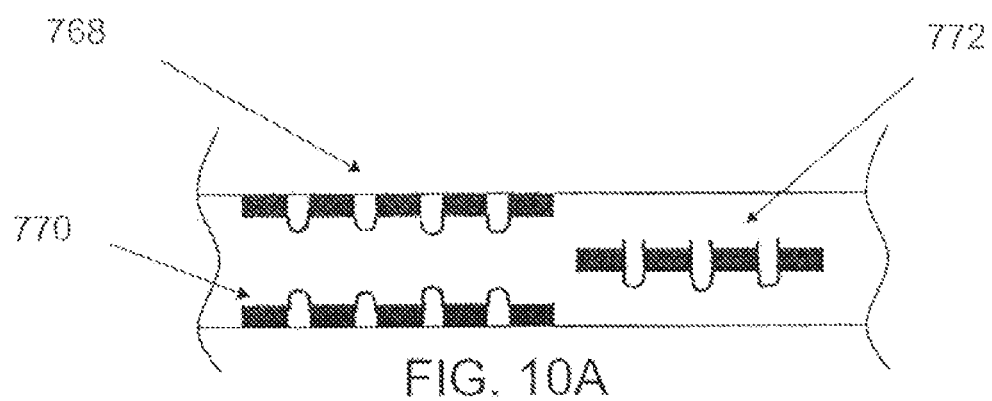
FIGS. 10A and 10B schematically depict various latch and opening configurations for a guide tunnel.
Figure 10B:
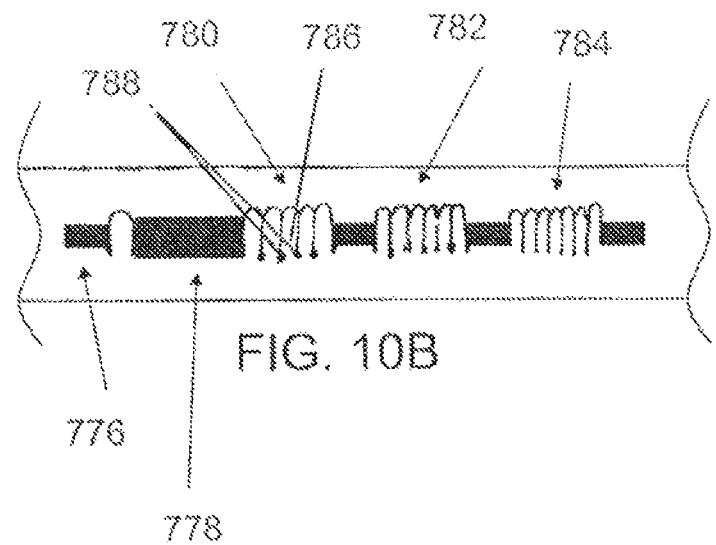

In the embodiments of the cinchable implants described above, several embodiments of guide tunnel 700 or tunnel catheter 148 depict a single, longitudinal arrangement of alternating identical sized openings 154 and identical retaining elements or latches 712, but alternate configurations are also contemplated. These alternate configurations may include, for example, two or more distinct groups, 768, 770, 772 of openings and retaining elements as illustrated in FIG. 10A, that may involve single or multiple locking mechanisms that may be released in parallel, in serial or in a mixed fashion. FIG. 10B is another embodiment of a guide tunnel 774 comprising variable-sized openings 776, 778 or retaining elements 780, 782, 784 and/or non-alternating retaining elements 780, 782, 784. The configuration depicted in FIG. 10B also demonstrates other features that may be incorporated into the tunnel catheter 148. For example, certain materials used to provide adequate column strength and torqueability to tunnel catheter 154 may result in retaining elements that are too stiff or bulky to easily release the tether safely. In some examples, the spacing between openings is such that the width of the retaining element is greater than the length of the retaining element by about 1×, or about 2× or about 3× multiple or more. To reduce the potential of snagging or inability to pass the tether, a series of consecutive retaining elements 780, 782, 784 having a smaller width may be used. FIG. 10B also depicts retaining elements 786 with a tapered base 788 to facilitate bending of retaining elements 786.

Referring again to FIGS. 14A through 14H, a more detailed description of guide tunnel 700 is provided. FIG. 14A illustrates distal section 706 of guide tunnel 700. Distal section 706 is configured with a curvature configured to facilitate the placement of anchors in the subannular groove region. Seven openings 706 are provided along the greater curvature 708 of distal section 706. In other embodiments, the number of openings 706 may vary from about 2 or about 3, to about 30 or more. In preferred embodiments, openings 706 may number from about 5 to about 20, while in most preferred embodiments, openings 706 may number from about 7 to about 10. In some embodiments, openings 706 may have a length of about 3 mm to about 20 mm, preferably about 5 mm to 10 mm and most preferably about 7 mm to about 8 mm. In some embodiments, openings 706 may have a width of about 1 mm to about 10 mm, preferably about 2 mm to about 7 mm, and most preferably about 3 mm to about 5 mm.

Figure 11:
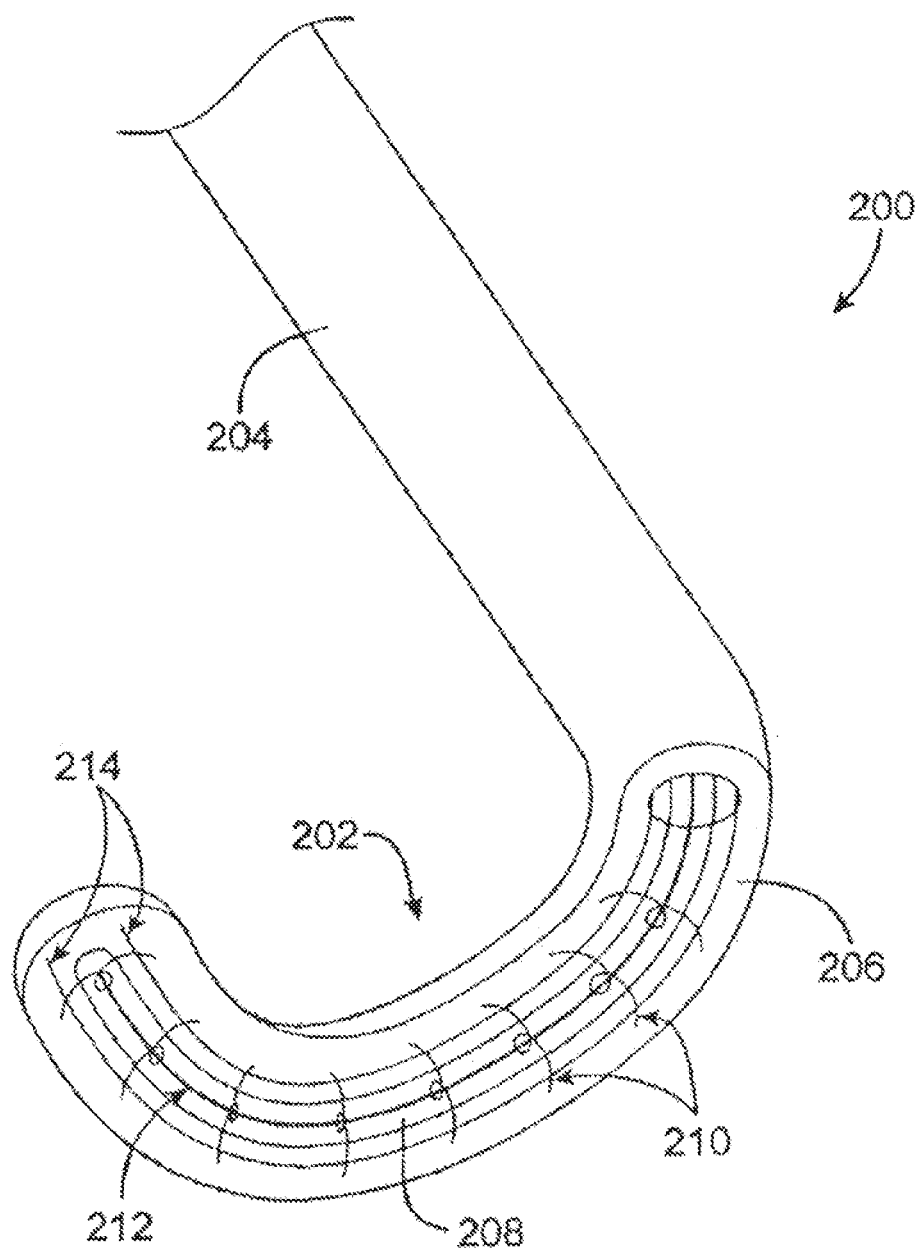
FIG. 11 is a perspective view of a distal portion of one embodiment of an anchor delivery catheter.

With reference now to FIG. 11, one embodiment of the invention comprises an anchor delivery device 200, which suitably includes an elongate shaft 204 having a distal portion 202 configured to deliver a plurality of anchors 210, coupled with a tether 212, and configured for attachment to annular tissue. The tethered anchors 210 are housed within a housing 206 of the distal portion 202, along with one or more anchor retaining mandrels 214 and a delivery opening 208. Many variant embodiments may be made to one or more of these features, and various parts may be added or eliminated. Some of these variations are described further below, but no specific variation(s) should be construed as limiting.

Housing 206 may be flexible or rigid in some variations. In some embodiments, for example, flexible housing 206 may comprise multiple segments configured such that housing 206 is deformable by tensioning a tensioning member coupled to the segments. In some embodiments, housing 206 is formed from an elastic material having a geometry selected to engage and optionally shape or constrict the annular tissue. For example, the rings may be formed from spring stainless steel, super-elastic shape memory alloys such as nickel-titanium alloys (e.g., Nitinol), or the like. In other embodiments, the housing 206 could be formed from an inflatable or other structure that can be selectively rigidified in situ, such as a gooseneck or lockable element shaft, any of the rigidifying structures described above, or any other rigidifying structure.

In some embodiments of the invention, anchors 210 are generally C-shaped or semicircular in their undeployed form, with the ends of the "C" being sufficiently sharpened to penetrate tissue. Between the ends of the C-shaped anchor 210, an eyelet may be formed for allowing slidable passage of the tether 212. To maintain the anchors 210 in their C-shaped, undeployed state, anchors 210 may be retained within housing 206 by two mandrels 214, one mandrel 214 retaining each of the two arms of the C-shape of each anchor 210. Mandrels 214 may be retractable within elongate catheter body 204 to release anchors 210 and allow them to change from their undeployed C-shape to a deployed shape. The deployed shape, for example, may approximate a partial or complete circle, or a circle with overlapping ends, the latter appearing similar to a key ring. Such anchors are described further below, but generally may be advantageous in their ability to secure themselves to annular tissue by changing from their undeployed to their deployed shape. In some variations, anchors 210 are also configured to lie flush with a tissue surface after being deployed. By "flush" it is meant that no significant amount of an anchor protrudes from the surface, although some small portion may protrude.

The retaining mandrels 214 may have any suitable cross-sectional shape, cross-sectional area, length and be made of any suitable material, such as stainless steel, titanium, nickel-titanium alloys (e.g., Nitinol), or the like. Some embodiments may not include a mandrel, or may have one mandrel, two mandrels, or more than two mandrels.

In some embodiments, the anchors 210 may be released from mandrels 214 to contact and secure themselves to annular tissue without any further force applied by the delivery device 200. Some embodiments, however, may also include one or more expandable members 208, which may be expanded to help drive anchors 210 into tissue. Expandable member(s) 208 may have any suitable size and configuration and may be made of any suitable material(s). Any of a variety of mechanical and hydraulic expandable members known in the art may be included in housing 206.

In another embodiment of the invention, shown in FIGS. 12A and 12B, a flexible distal portion of an anchor delivery device 520 includes a housing 522 configured to house multiple coupled anchors 526 and an anchor contacting member 530 coupled with a pull cord 532. Housing 522 may also include multiple apertures 528 for allowing egress of anchors 526. For clarity, delivery device 520 is shown without a tether in FIG. 12A, but FIG. 12B shows that a tether 534 may extend through an eyelet, loop or other portion of each anchor 526, and may exit each aperture 528 to allow for release of the plurality of anchors 526. Anchors 526 may be relatively straight and may lie relatively in parallel with the long axis of delivery device 520. Anchor contacting member 530, which may comprise any suitable device, such as a ball, plate, hook, knot, plunger, piston, or the like, generally has an outer diameter that is nearly equal to or slightly less than the inner diameter of housing 522. Contacting member 530 is disposed within the housing, distal to a distal-most anchor 526, and is retracted relative to housing 522 by pulling pull cord 532. When retracted, anchor contacting member 530 contacts and applies force to a distal-most anchor 526 to cause release of that anchor 526 from housing 522 via one of the apertures 528. Contacting member 530 is then pulled farther proximally to contact and apply force to the next anchor 526 to deploy that anchor 526, and so on.

Retracting contacting member 530 to push anchors 526 out of apertures 528 may help cause anchors 526 to secure themselves to the tissue adjacent the apertures 528. Using anchors 526 that are relatively straighter/flatter configuration when undeployed may allow anchors 526 with relatively large deployed sizes to be disposed in (and delivered from) a relatively small housing 522. In one embodiment, for example, anchors 526 that deploy into a shape approximating two intersecting semi-circles, circles, ovals, helices, or the like, and that have a radius of one of the semi-circles of about 3 mm may be disposed within a housing 522 having a diameter of about 6 French (2.00 mm) and more preferably about 5 French (1.67 mm) or even smaller. Such anchors 526 may measure about 6 mm or more in their widest dimension. In some embodiments, housing 522 may have a diametrical dimension ("d") and anchor 526 may have a diametrical dimension ("D") in the deployed state, and the ratio of D to d may be at least about 3.5. In other embodiments, the ratio of D to d may be at least about 4.4, and more preferably at least about 7, and even more preferably at least about 8.8. These are only examples, however, and other larger or smaller anchors 526 may be disposed within a larger or smaller housing 522. The dimensions of an anchor may vary depending on the particular usage. For example, anchors used for ventriculoplasty may permit the use of larger anchors than those used for annuloplasty due to fewer space constraints in the main compartment of the ventricles than in the subvalvular spaces. Furthermore, any convenient number of anchors 526 may be disposed within housing 522. In one variation, for example, housing 522 may hold about 1 to about 20 anchors 526, and more preferably about 3 to about 10 anchors 526. Other variations may hold more anchors 526.

Anchor contacting member 530 and pull cord 532 may have any suitable configuration and may be manufactured from any material or combination of materials. In alternative embodiments of the invention, contacting member 530 may be pushed by a pusher member to contact and deploy anchors 526. Alternatively, any of the anchor deployment devices and methods previously described may be used.

Tether 534, as shown in FIG. 12B, may comprise any of the tethers 534 or tether-like devices already described above, or any other suitable device. Tether 534 is generally attached to a distal-most anchor 526 at an attachment point 536. The attachment itself may be achieved via a knot, weld, adhesive, or by any other suitable attachment mechanism. Tether 234 then extends through an eyelet, loop or other similar configuration on each of the anchors 526 so as to be slidably coupled with the anchors 526. In the particular embodiment shown, tether 534 exits each aperture 528, then enters the next-most-proximal aperture, passes slidably through a loop on an anchor 526, and exits the same aperture 528. By entering and exiting each aperture 528, tether 534 allows the plurality of anchors 526 to be deployed into tissue and cinched. Alternate embodiments of housing 522, anchors 526 and tether 534 may also be used. For example, housing 522 may include a longitudinal slit through which tether 534 may pass, thus allowing tether 534 to reside wholly within housing before deployment.

Figure 13A:
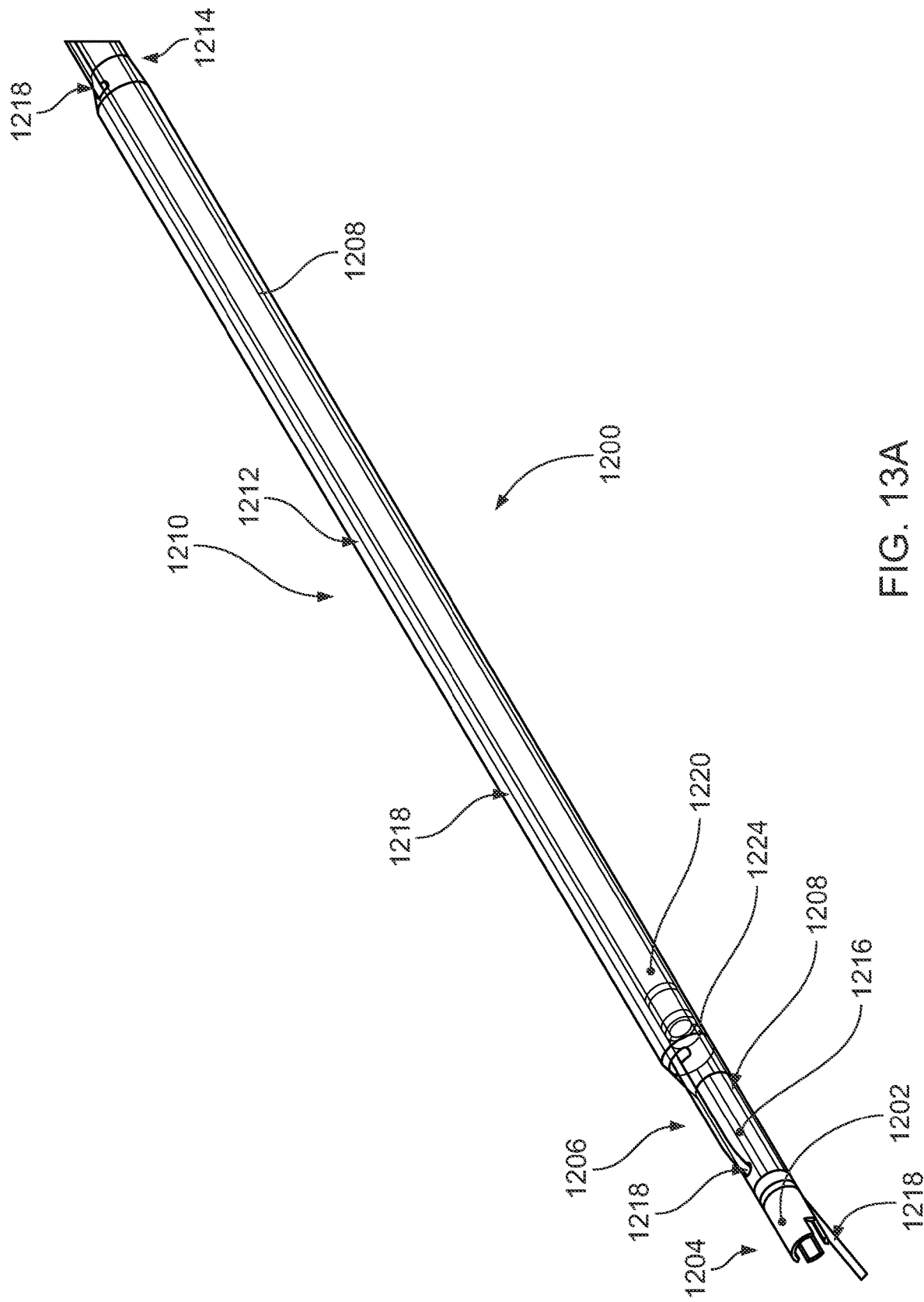
FIG. 13A is a perspective view of another embodiment of a delivery catheter.

FIGS. 13A to 13D represent various views of one embodiment of a delivery catheter 1200 that can be used to deliver one or more anchors to a target site. As shown in FIG. 13A, delivery catheter 1200 has a distal region 1204 including a tip 1202, an anchor-holding region 1206 including a primary lumen 1208, an intermediate region 1210 including both primary lumen 1208 and a secondary lumen 1212, and a proximal region 1214 including primary lumen 1208. An anchor 1216 is disposed within primary lumen 1208, in the anchor-holding region 1206. While only one anchor is shown in the anchor-holding region of this embodiment, in other embodiments of the invention, the delivery catheters may include an anchor-holding region that is adapted to hold multiple anchors. Similarly, while the variation shown in FIGS. 13A to 13D depict anchors adapted to be deployed from distal region 1204 of delivery catheter 1200, it should be understood that the anchors may be deployed from any suitable region of delivery catheter 1200, as desirable. For example, if desirable, the anchor may be delivered out of a side port or hole on the delivery catheter.

As shown in FIGS. 13A to 13D, a tether 1218 may be threaded into a slot 1219 of tip 1202 (shown in FIGS. 13C and 13D), and through an eyelet 1226 of anchor 1216. After extending through eyelet 1226, tether 1218 exits primary lumen 1208, and extends along an exterior surface 1221 of delivery catheter 1200 for the remainder of the length of the anchor-holding region, as shown in FIG. 13C. Tether 1218 then enters secondary lumen 1212, and extends through the length of secondary lumen 1212, exiting secondary lumen 1212 at an end of distal region 1214. An actuator 1220 is slidably disposed within primary lumen 1208, and can be used to push or deploy anchor 1216 out of the primary lumen 1208. Actuator 1220 is in the form of a pushable generally tubular member, although other forms of actuators may be used. For example, in some variations, a solid rod may be used as an actuator. Once a sufficient distal portion of anchor 1216 has been displaced out of primary lumen 1208, the self-expanding properties of anchor 1216 may cause the biased distal ends to expand outwardly and cause the remainder of anchor 1216 to "spring out" or "shoot out" of distal end 1202 and facilitate tissue piercing by anchor 1216. Eyelet 1226 will also engage tether 1218 as anchor 1216 exits delivery catheter 1200. In other embodiments, actuator 1220 may be spring-loaded or biased to facilitate tissue piercing. Additional embodiments of the delivery catheter are described in U.S. patent application Ser. No. 11/202,474, which was previously incorporated by reference.

Delivery catheter 1200 may optionally comprise a retrieval member, such as a retrieval line or filament 1222 that is looped around eyelet 1226 of anchor 1216 and threaded proximally back through delivery catheter 1200. Retrieval filament 1222 is pulled of delivery catheter 1200 by eyelet 1226 when anchor 1216 is deployed. Retrieval filament 1222 may be used to pull back anchor 1216 into delivery catheter 1200 should anchor 1216 misfire and fail to engage body tissue. If anchor 1216 is successfully deployed, one end of retrieval filament 1222 may be pulled out from eyelet 1226 to release anchor 1216 from retrieval filament 1222.

Figure 15A:
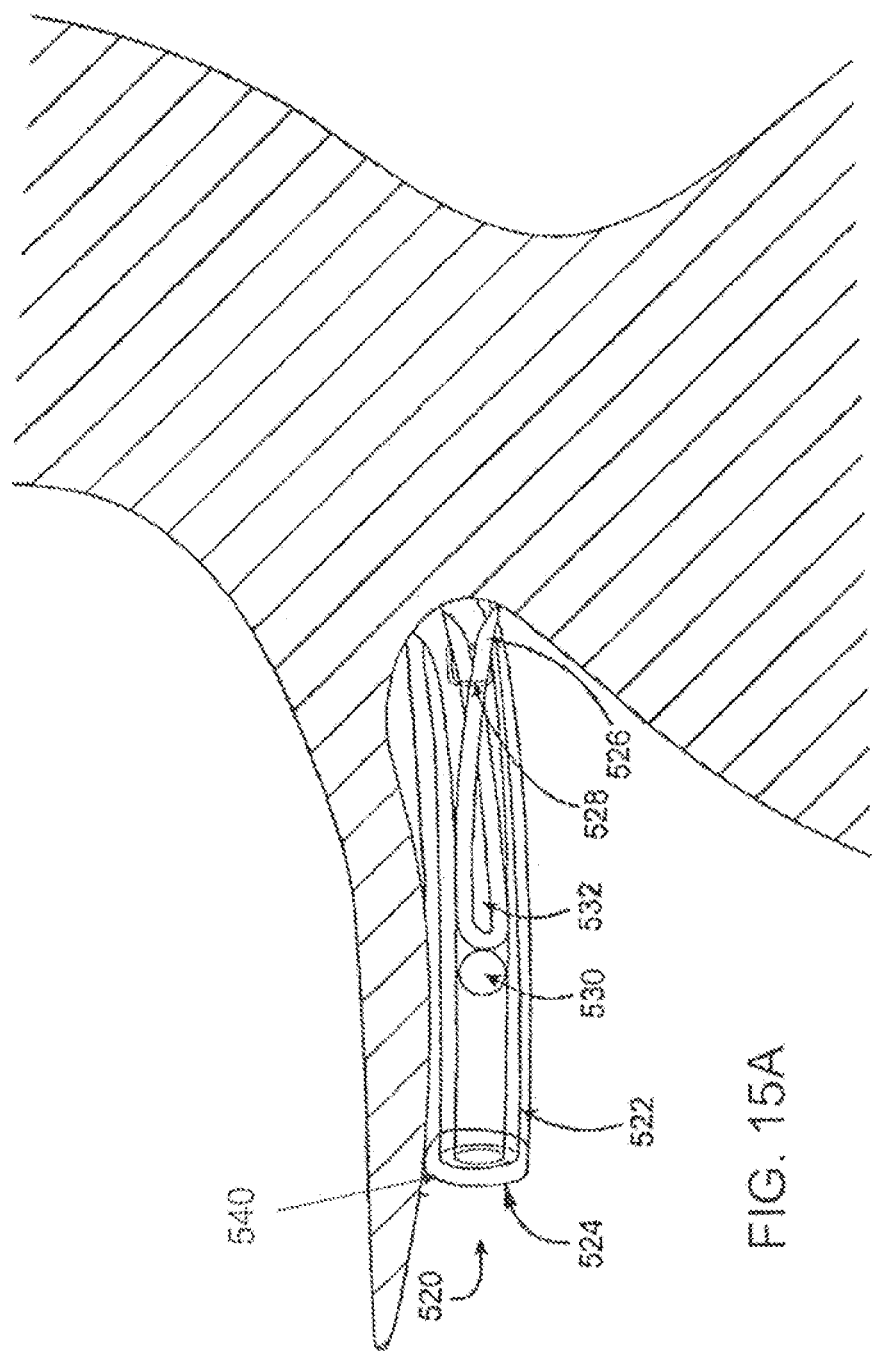

With reference to FIGS. 15A to 15F, one embodiment of the invention comprises a method for applying a plurality of tethered anchors 526 to the annular tissue of a heart. As shown in FIG. 15A, an anchor delivery device 520 is first contacted with the valve annulus VA or annular tissue such that openings 528 are oriented to deploy anchors 526 into the tissue. Such orientation may be achieved by any suitable technique. In one embodiment, for example, a housing 522 having an elliptical cross-sectional shape may be used to orient openings 528. Contact between housing 522 and the annular tissue may be enhanced by expanding expandable member 524 to wedge housing 522 within the deepest portion of the subannular groove region.

Generally, delivery device 520 may be advanced into any suitable location for treating any valve or body tissue by any suitable advancing or device placement method. For example, in one embodiment a guide member is first advanced in a retrograde fashion through an aorta, typically via access from a femoral artery. The guide member is passed into the left ventricle of the heart and thus into the space formed by the mitral valve leaflets, the left ventricular wall and chordae tendineae of the left ventricle. Once in this space, the guide member is advanced along a portion (or all) of the circumference of the mitral valve. A sheath 540 is advanced over the guide member within the space below the valve leaflets, and the guide element is removed through sheath 540. In some embodiments, the guide member may comprise a steerable guide catheter. Anchor delivery device 520 may then be advanced through the sheath to a desired position within the space, and sheath 540 may be removed. In other embodiments, a tunnel catheter 148 (shown in ghost) is passed through the sheath to provide additional stability and to facilitate positioning of the delivery device 520.

Figure 15C:
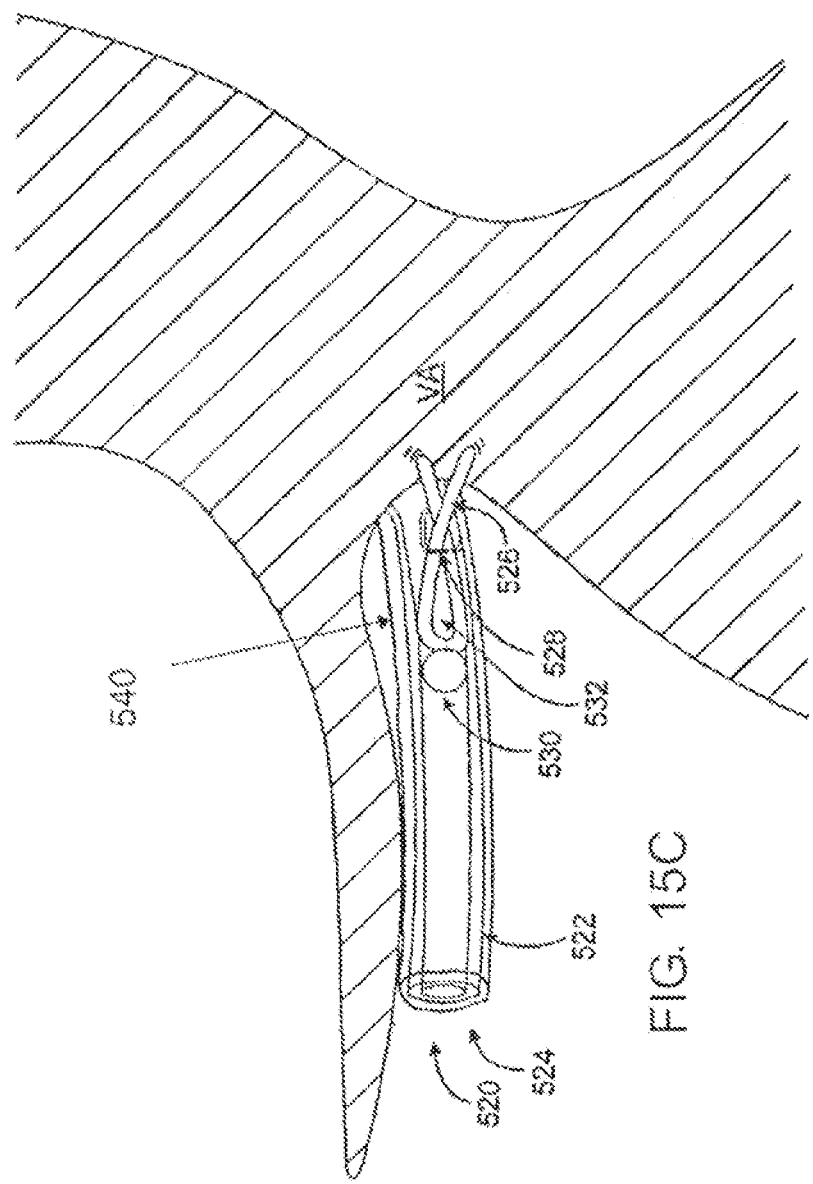

As shown in FIG. 15B, when delivery device 520 is positioned in a desired location for deploying anchors 526, anchor contacting member 530 is retracted to contact and apply force to a most-distal anchor 526 to begin deploying anchor 526 through aperture 528 and into the valve annulus VA or annular tissue. FIG. 15C shows anchor 526 further deployed out of aperture 528 and into valve annulus VA or annular tissue. FIG. 15D shows the valve annulus VA transparently so that further deployment of anchors 526 can be seen. As shown, in one embodiment, anchors 526 include two tips that move in opposite directions upon release from housing 522 and upon contacting the valve annulus VA or annular tissue. Between the two tips, an anchor 526 may be looped or have any other suitable eyelet or other device for allowing slidable coupling with a tether 534.

Referring now to FIG. 15E, anchors 526 are seen in their fully deployed or nearly fully deployed shape, with each tip (or "arm") of each anchor 526 having curved to form a circle or semi-circle. In some variations anchors 526 may have any other suitable deployed and undeployed shapes, as described more fully above. FIG. 15F shows anchors 526 deployed into the valve annulus VA or annular tissue and coupled to tether 534, with the distal-most anchor 526 coupled to tether 524 at attachment point 536. At this stage, tether 534 may be tensioned to tighten the annular tissue, thus reducing valve regurgitation. In some embodiments, valve function may be monitored by means such as echocardiogram and/or fluoroscopy, and tether 534 may be tensioned, loosened, and adjusted to achieve a desired amount of tightening as evident via the employed visualization technique(s). When a desired amount of tightening is achieved, the implant may be fixed using any of a variety of termination devices and methods.

For example, in one embodiment, tensioning tether 534, attaching tether 534 to most-proximal anchor 526, and cutting tether 534 are achieved using a termination device (not shown). The termination device may comprise, for example, a catheter advanceable over tether 534 that includes a cutting member and a nickel-titanium alloy (e.g., Nitinol) knot or other attachment member for attaching tether 534 to most-proximal anchor. The termination catheter may be advanced over tether 534 to a location at or near the proximal end of the tethered anchors 526. It may then be used to apply opposing force to the most-proximal anchor 526 while tether 534 is tensioned. Attachment and cutting members may then be used to attach tether 534 to most-proximal anchor 526 and cut tether 534 just proximal to most-proximal anchor 526. Such a termination device is only one possible way of accomplishing the cinching, attachment and cutting steps, and any other suitable device(s) or technique(s) may be used. Additional devices and methods for terminating (e.g., cinching and fastening) may be found, for example, in U.S. patent application Ser. No. 11/232,190, previously incorporated by reference, and U.S. patent application Ser. No. 11/270,034, and Ser. No. 11/875,774, both of which are herein incorporated by reference in their entirety. In some embodiments, the termination device is located in the same heart chamber as the remaining portions of the implant, which permits the implant to be wholly implanted in a single heart chamber. In other embodiments, however, a portion of the implant passes transmurally through a septal wall or an outer wall of a heart chamber. In these embodiments, the termination member and optionally one or more anchors may be located in a different heart chamber.

In some embodiments, it may be advantageous to deploy a first number of anchors 526 along a first portion of annular tissue, cinch the first anchors to tighten that portion of the annular tissue, move the delivery device 520 to another portion of the annular tissue, and deploy and cinch a second number of anchors 526 along a second portion of the annular tissue. Such a method may be more convenient, in some cases, than extending delivery device 520 around all or most of the circumference of the annular tissue, and may allow a shorter, more maneuverable housing 522 to be used.

Figure 16A:
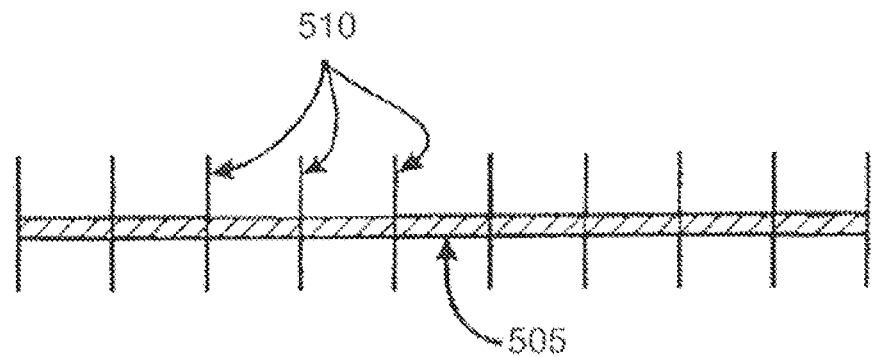
FIGS. 16A and 16B are schematic top-views of a plurality of anchors coupled to a self-deforming coupling member, with the coupling member shown in an undeployed shape and a deployed shape, respectively.
Figure 16B:
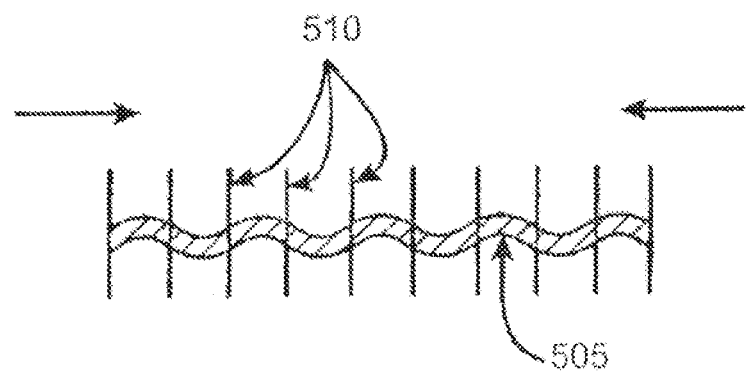

With reference to FIGS. 16A and 16B, a diagrammatic representation of another embodiment of the invention, comprising coupled anchors is shown. Here, anchors 510 are coupled to a self-deforming or deformable coupling member or backbone 505. This backbone 505 is another embodiment of a tether. The backbone 505 may be fabricated, for example, from nickel-titanium alloys (e.g., Nitinol), spring stainless steel, or the like, and may have any suitable size or configuration. In one embodiment, as in FIG. 16A, backbone 505 is shaped as a generally straight line when held in an undeployed state, such as when restrained within a housing of an anchor deliver device. When released from the delivery device, backbone 505 may change to a deployed shape having multiple bends, as shown in FIG. 16B. By bending, backbone 505 shortens the longitudinal distance between anchors, as demonstrated by the solid-tipped arrows in FIG. 16B. This shortening process may act to reshape any tissue or structure into which anchors 510 have been secured. Thus, anchors 510 coupled to backbone 505 may be used to reshape annular tissue or any other tissue without using a separate tether or applying tethering force. In other embodiments, an elastic tether may be used as the backbone 505. In still other embodiments, backbone may also be coupled with a termination member to further cinch the annular tissue. In such an embodiment, the backbone 505 is adapted to be at least partially conformable or cinchable, such that when force is applied to anchors 510 and backbone 505 via a tether, backbone 505 buckles or compresses further to allow further cinching of the annular tissue.

Although the preferred access route to the subannular groove region 104 or subvalvular space 106 is a retrograde route through the aorta A to the heart H, other access routes may also be used. Access to the heart H may also be transthoracic, with a delivery device being introduced into the heart via an incision or port in the heart wall. Even open heart surgical procedures may benefit from the methods and devices described herein. In some embodiments of the invention, hybrid access involving a combination of access methods described herein may be used. In one specific example, dual access to a valve may be achieved with a combination of venous and arterial access sites. User manipulation of both ends of a guidewire placed across a valve may improve positioning and control of the catheter and the implants. In other examples of hybrid access, both minimally invasive and surgical access is used to implant one or more cardiac devices.

Other embodiments of the invention also include treatment of the tricuspid valve annulus, tissue adjacent the tricuspid valve leaflets TVL, or any other cardiac or vascular valve. Thus, although the description herein discloses specific examples of devices and methods of the invention for mitral valve repair, the devices and methods of the invention may be used in any suitable procedure, both cardiac and non-cardiac. For example, in other embodiments of the invention, the mitral valve reshaping devices and procedures may be used with the tricuspid valves also, and certain embodiments may also be adapted for use with the pulmonary and aortic valves. Likewise, the other examples provided below are directed to the left ventricle, but the devices and methods may also be adapted by one of ordinary skill in the art for use in the right ventricle or either atrium. The devices and methods may also be used with the great vessels of the cardiovascular system, for example, to treat aortic root dilatation.

Figure 17:
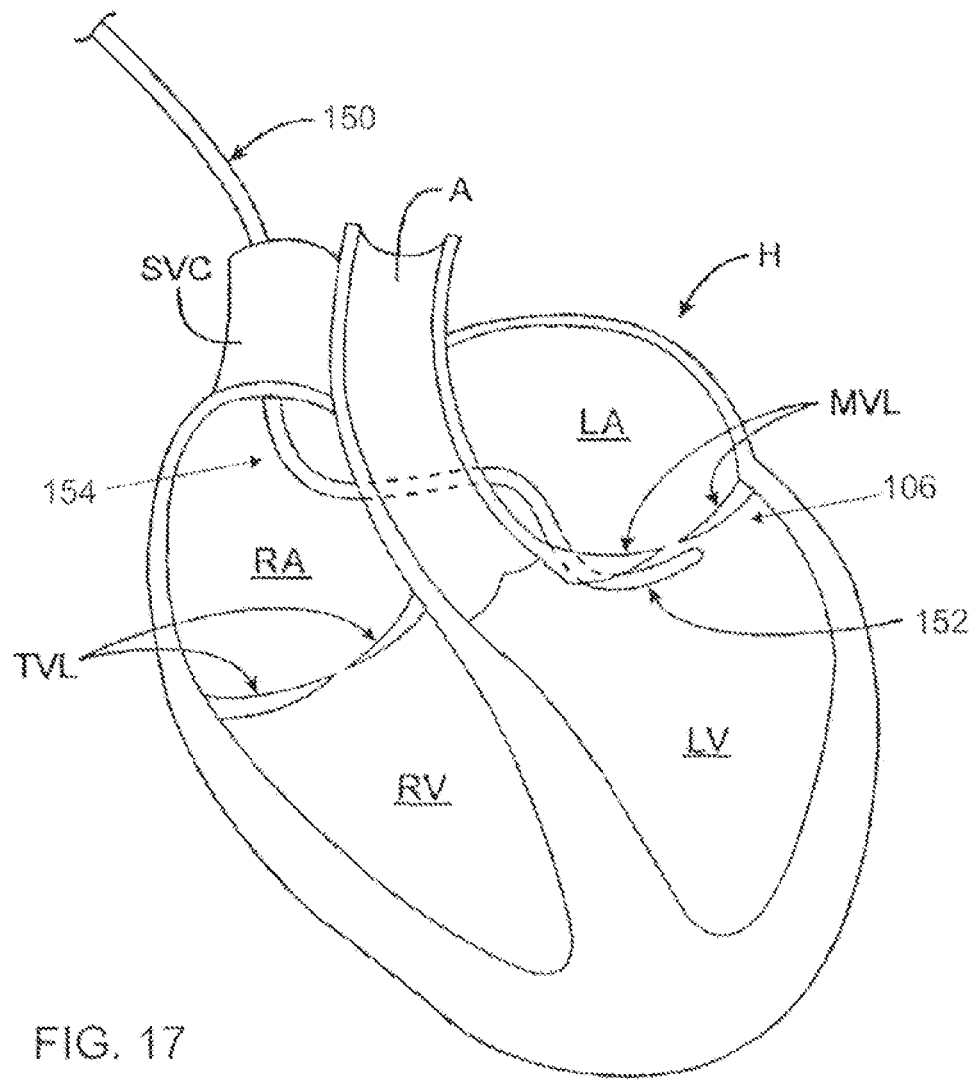
FIG. 17 shows a transseptal approach to the left ventricle.

Access to the other chambers of the heart may be performed through percutaneous or venous cut-down access, including but not limited to transjugular, subclavicular and femoral vein access routes. When venous access is established, access to the right atrium RA, the right ventricle RV, the tricuspid valve TV and other right-sided cardiac structures can occur. Furthermore, access to left-sided heart structures, such as the left atrium LA, left ventricle LV, mitral valve and the aortic valve, may be subsequently achieved by performing a transseptal puncture procedure. Referring to FIG. 17 with a heart H is shown in cross section, transseptal puncture is traditionally performed using a Mullins introducer sheath with a Brockenbrough curved needle through the interatrial septum to access the left atrium LA, but any of a variety of other transseptal puncture devices or kits may also be used. After puncturing through the left atrium LA, supravalvular access to the mitral valve is achieved. Antegrade access to the left ventricle LV can also occur by crossing the mitral valve. Similarly, access from the right ventricle RV to the left ventricle LV may be obtained by transseptal puncture of the ventricular septum. In still other embodiments, a catheter device may access the coronary sinus and a valve procedure may be performed directly from the sinus.

Figure 18:
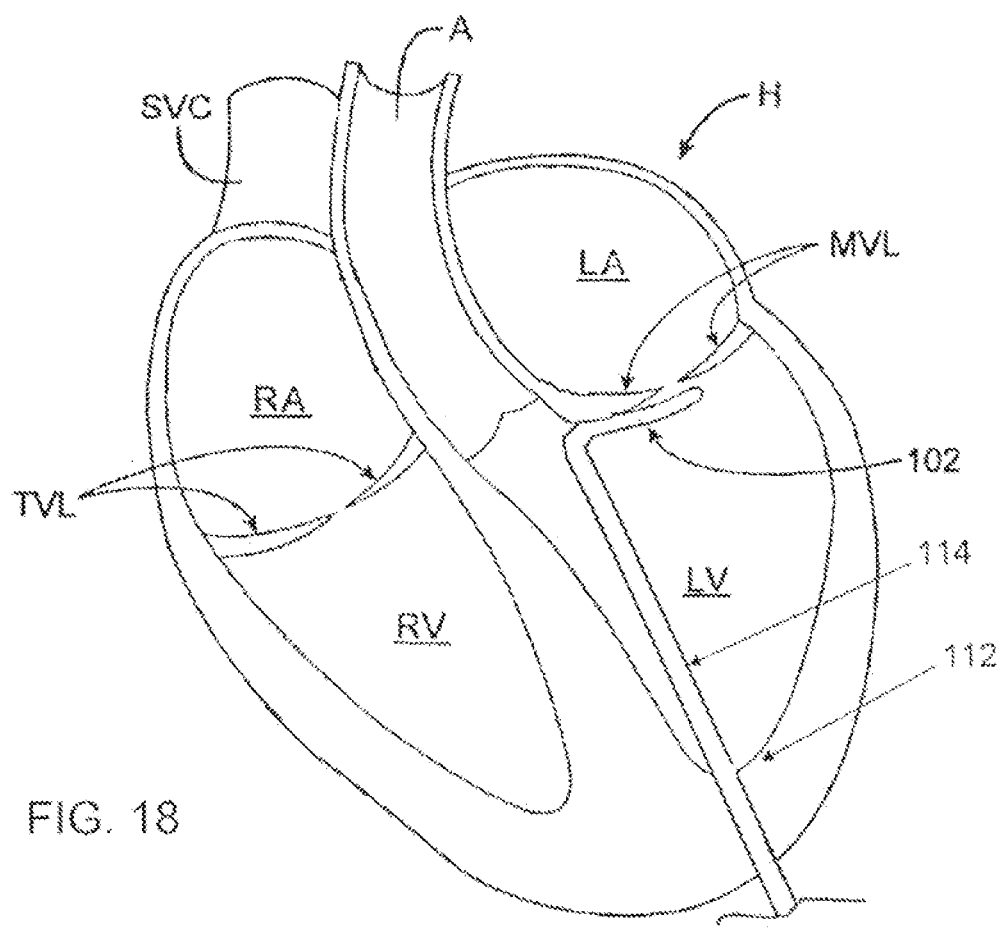
FIG. 18 shows a transapical approach to the left ventricle.

Surgical approaches that may be used have been described above but also include but are not limited to transcatheter procedures made through surgical incisions in the aorta or myocardium. In one particular embodiment, depicted in FIG. 18, a transapical approach with a surgical delivery device 114 is utilized, to provide a more linear route to the subvalvular space 106. The transapical approach also reduces potential effects of a myocardial incision on cardiac output, as the apical wall 112 typically contributes less mechanical effect on left ventricular ejection fraction compared to other sections of the myocardial wall.

In addition to performing valve annuloplasty with the multi-opening guide tunnel, other uses, including cardiac and non-cardiac applications, are contemplated within the scope of the invention. In one embodiment of the invention, reconfiguration of the subvalvular apparatus with a cinchable implant delivered by a multi-opening delivery tool with a releasable tether retaining mechanism is contemplated. For example, a plurality of tethered anchors may be secured to the myocardium adjacent the papillary muscle and then cinched to tension the myocardium and cause repositioning of one or more papillary muscles.

In other embodiments, the reshaping of a ventricle may be performed using a multi-opening guide tunnel with a releasable tether retaining mechanism, along any of a variety of dimensions or vectors. For example, referring to FIG. 19, in some embodiments of the invention, the reshaping of a ventricle or a valve may occur with respect to the diameter B or the circumference C about a valve orifice. In one preferred embodiment, the diameter B and the circumference C with respect to the subannular groove region 104 of a ventricle is reshaped. In addition to the reshaping of to valvular structures, reshaping can also be performed with respect to the non-valvular structures of a heart chamber. For example, one or more of the diameters or circumferences of the ventricle may be reshaped. As shown in FIG. 19, the diameter B' and the circumference C' of the ventricle located generally at or above the papillary muscles may be reshaped. The diameter B" and circumference C" of the ventricle at or below the papillary muscles may also be reshaped. The orientation of the diameter and circumference that is reshaped or assessed can vary, but in some embodiments, the diameter or circumference may be in a generally perpendicular orientation with respect to a longitudinal axis of a ventricle. One of skill in the art will understand that the longitudinal axis may be characterized in a number of ways, including but not limited to a longitudinal axis from a valve orifice to an apex of a heart chamber, or from the apex of a heart chamber to a point that generally splits the ventricular volume in half. Similarly, some of the implantation dimensions or vectors may also be oriented with respect to the anterior-posterior axis or the septo-lateral axis of the heart chamber.

Referring to FIG. 20, in some embodiments, the myocardium along vectors A, D between a papillary muscle and a valve leaflet may be reshaped. Vectors D or A may be between a papillary muscle and its associated valve leaflet, or between a papillary muscle and an unassociated valve leaflet, respectively. Although the vectors A, D depicted in FIG. 20 are shown from the tip of the papillary muscle, these pathways may also be assessed from the base of the papillary muscle. Similarly, myocardial pathways including a valve leaflet may be assessed from the distalmost section, the middle or the base of the valve leaflet. In other embodiments, the reshaping of the heart may occur between the apex of a heart chamber and one or more valves. For example, reshaping may occur along the vector E between the outlet valve and the apex of a heart chamber, and/or along the pathway F between the inlet valve and the apex.

Figure 21:
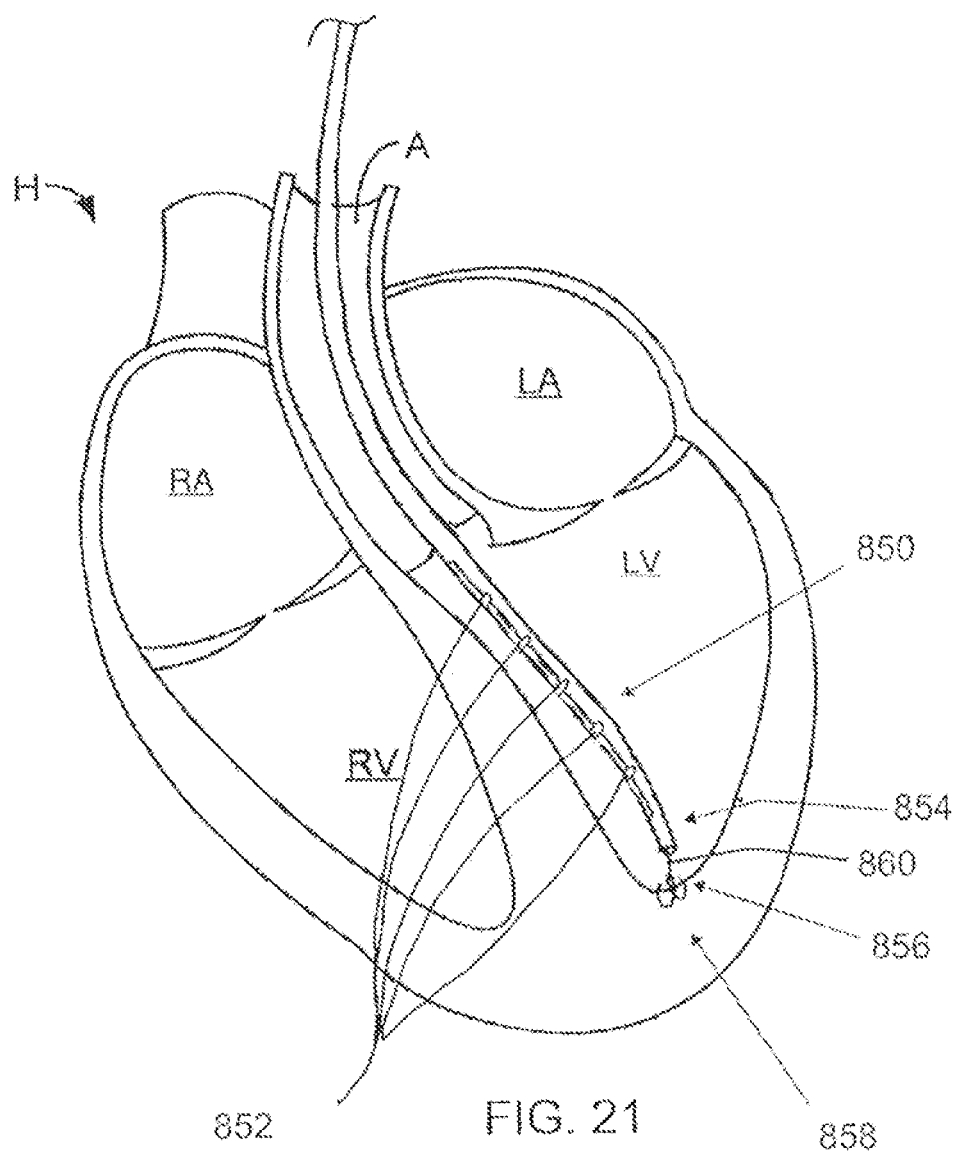
FIG. 21 depicts the use of a multi-opening guide tunnel along a longitudinal portion of the left ventricle.

In FIG. 21, for example, a multi-opening guide tunnel 850 with latches 852 is used to place a cinchable implant 854 along vector E from FIG. 20. To implant a ventricular device in a beating heart, in some embodiments of the invention one end of the implant is preferably first attached to a less mobile portion of the ventricle chamber. The distal end 856 of the implant 854 is first secured to the apical region 858 of the left ventricle LV. Once the distal end 856 of the implant 854 is stabilized, guide tunnel 850 can be stabilized using the secured distal end 854 and provide increased stability during the procedure by releasably retaining portions of the tether 860 as the remaining anchors are deployed.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A method for performing a procedure inside a heart comprising:
   positioning a multi-aperture catheter circumferentially along myocardium located generally at or near papillary muscles, the multi-aperture catheter comprising a lumen at least partially therethrough and a plurality of apertures along a distal portion of the catheter, wherein the plurality of apertures are defined by a plurality of releasable retaining structures;
   advancing a device comprising at least one anchor coupled to a tether at least partially through the lumen;
   temporarily securing the distal portion of the multi-aperture catheter to the myocardium using the device, wherein the tether is retained within the lumen;
   releasing the multi-aperture catheter from the myocardium by releasing the tether from the lumen, wherein the at least one anchor and the tether remain secured to the myocardium at or near the papillary muscles; and
   removing the multi-aperture catheter from the heart.

2. The method of claim 1, further comprising a locking element configured to lock the plurality of releasable retaining structures.

3. The method of claim 2, wherein releasing the multi-aperture catheter from the myocardium comprises withdrawing the locking element to release the tether from the lumen.

4. The method of claim 1, wherein the plurality of apertures are located along a length of the distal portion of the catheter.

5. The method of claim 1, wherein the multi-aperture catheter comprises one or more retention members.

6. The method of claim 1, wherein the device comprises a plurality of anchors coupled to the tether.

7. The method of claim 1, wherein the multi-aperture catheter is positioned adjacent to the myocardium at or near the papillary muscles using an intravascular approach.

8. The method of claim 1, wherein the multi-aperture catheter is positioned adjacent to the myocardium at or near the papillary muscles using a surgical technique.

9. The method of claim 1, wherein the multi-aperture catheter is positioned adjacent to the myocardium at or near the papillary muscles using port access to the heart.

10. The method of claim 1, wherein the multi-aperture catheter comprises a plurality of retention members and wherein the multi-aperture catheter is released from the myocardium at or near the papillary muscles by moving the retention members.

11. The method of claim 1, wherein the multi-aperture catheter comprises at least a first aperture and a second aperture, both apertures positioned along a length of the distal portion of the multi-aperture catheter.

12. The method of claim 11, wherein the device comprises at least a first anchor and a second anchor, at least one of the first or second anchors is fixedly coupled to the tether.

13. The method of claim 12, wherein the first anchor is deployed through the first aperture and the second anchor is deployed through the second aperture.

14. The method of claim 13, wherein at least one of the first or second anchors is slidably coupled to the tether.

15. The method of claim 14, further comprising tensioning the tether.

16. The method of claim 15, further comprising securing the tether in its tensioned state.

17. The method of claim 16, further comprising cutting the tether.

18. The method of claim 15, wherein tensioning the tether causes tensioning of the myocardium at or near the papillary muscles and thus causes repositioning of one or more of the papillary muscles.

19. The method of claim 1, wherein the papillary muscles are anterior-lateral papillary muscles.

20. The method of claim 1, wherein the papillary muscles are posterior-medial papillary muscles.

* * * * *